United States Patent
Abarghaz et al.

(10) Patent No.: US 7,410,963 B2
(45) Date of Patent: Aug. 12, 2008

(54) BENZO-1,4-DIAZEPIN-2-ONE DERIVATIVES AS PHOSPHODIESTERASE PDE2 INHIBITORS, PREPARATION AND THERAPEUTIC USE THEREOF

(75) Inventors: Mustapha Abarghaz, Wittenheim (FR); Stefano Biondi, Verona (IT); Jérôme Duranton, Strasbourg (FR); Emmanuelle Limanton, Hochstatt (FR); Cesare Mondadori, Reinach (CH); Patrick Wagner, Brumath (FR)

(73) Assignee: VIA Pharmaceuticals, Inc., San Francisco, CA (US)

( * ) Notice: Subject to any disclaimer, the term of this patent is extended or adjusted under 35 U.S.C. 154(b) by 19 days.

(21) Appl. No.: 10/582,131

(22) PCT Filed: Dec. 23, 2004

(86) PCT No.: PCT/IB2004/004362

§ 371 (c)(1), (2), (4) Date: Jun. 8, 2006

(87) PCT Pub. No.: WO2005/063723

PCT Pub. Date: Jul. 14, 2005

(65) Prior Publication Data

US 2007/0123519 A1    May 31, 2007

(30) Foreign Application Priority Data

Dec. 23, 2003    (EP) .................... 03293309

(51) Int. Cl.
C07D 243/24 (2006.01)
C07D 413/04 (2006.01)
A61K 31/5513 (2006.01)

(52) U.S. Cl. ...................... 514/221; 540/504
(58) Field of Classification Search .......... 540/504; 514/221
See application file for complete search history.

(56) References Cited

FOREIGN PATENT DOCUMENTS

WO    02/088096 A    11/2002
WO    02/098865 A    12/2002

OTHER PUBLICATIONS

International Search Report of PCT/IB2004/004362, mailed May 4, 2005.

*Primary Examiner*—Bruck Kifle

(57) ABSTRACT

The invention relates to compounds having PDE2 inhibitory activities, as well as therapeutic methods by administering said compounds, in particular for treating various diseases of the central or peripheral nervous system. It further deals with pharmaceutical compositions comprising said compounds and methods for preparing said compounds.

20 Claims, 5 Drawing Sheets

Figure 1:
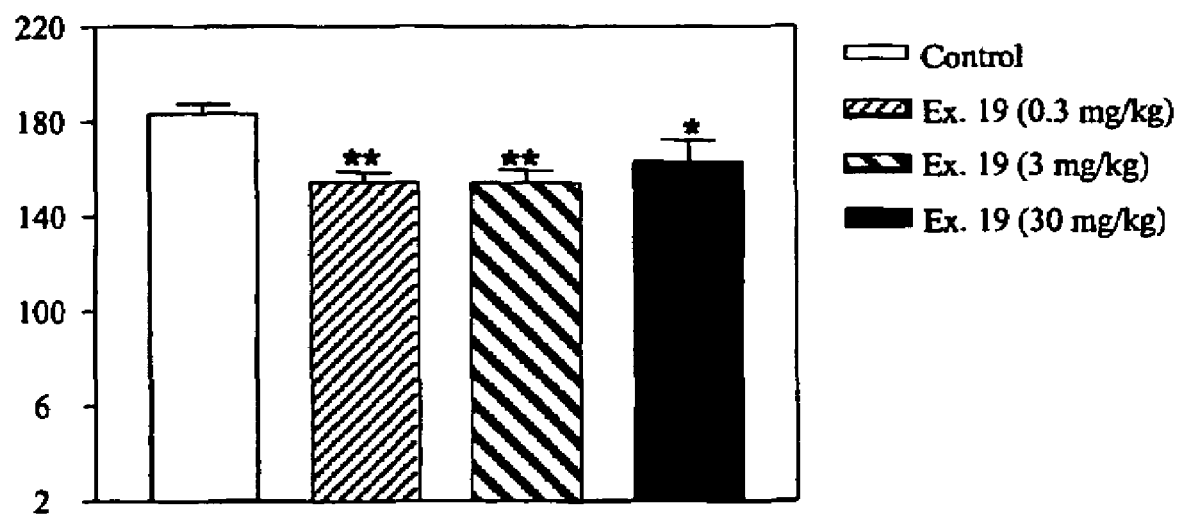

BENZO-1,4-DIAZEPIN-2-ONE DERIVATIVES AS PHOSPHODIESTERASE PDE2 INHIBITORS, PREPARATION AND THERAPEUTIC USE THEREOF

This application is the US national phase of international application PCT/IB2004/004362, filed 23 Dec. 2004, which designated the U.S. and claims priority of EP 03293309.5, filed 23 Dec. 2003, the entire contents of each of which are hereby incorporated by reference.

The invention relates to compounds and their uses, particularly in the pharmaceutical industry. The invention discloses compounds having PDE2 inhibitory activities, as well as therapeutic methods by administering said compounds, in particular for treating various diseases of the central or peripheral nervous system. It further deals with pharmaceutical compositions comprising said compounds and methods for preparing said compounds.

The compounds of the present invention present a very interesting pharmacological profile, since they are inhibitors of cyclic nucleotide phosphodiesterases and in particular cGS-PDE (cGMP-Stimulated PDEs, type 2-phosphodiesterase, or PDE2).

The intracellular second messenger cAMP or cGMP is broken down and deactivated by phosphodiesterase (PDE), which is classified into at least types I to XI. PDE is widely distributed in the tissue and organs of the body. Among these, type II phosphodiesterase breaks down both cAMP and cGMP and can be activated by cGMP. This type II phosphodiesterase is found in numerous tissues (adipocytes, brain, heart, lungs, kidneys, blood vessels, etc.). PDE2 inhibitors are able to increase or maintain intracellular cAMP and cGMP rates and thereby find therapeutic interests in various pathologies.

The present invention provides compounds having a high inhibiting activity on PDE2, and preferably a selectivity profile with respect to other PDE isoforms, including a low action on PDE3. This selectivity profile may extend to other types of enzymes, such as adenosine deaminase. Moreover, compounds of the invention present an interesting effect on the central nervous system (anticonvulsants, anxiolytics, sedative, antidepressants) or the peripheral nervous system (against rheumatism, autoinflammatory diseases, against dysfunction of liver due to ageing). They also avantageously present no perturbating effect on memory.

The present invention discloses therefore compounds having the following general formula (I):

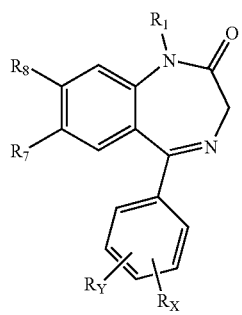

(I)

wherein:
$R_1$ represents an hydrogen atom, $(C_1-C_6)$alkyl, aryl, $(C_1-C_6)$alkylaryl, aryl$(C_1-C_6)$alkyl group, $(C_3-C_6)$alkenyl, or $(C_3-C_6)$alkenylaryl, $R_7$ represents a, substituted or not substituted, aryl or heteroaryl group, when $R_7$ is a substituted aryl, it is preferably mono or bis substituted by the following groups: a $(C_1-C_6)$alkyl, $(C_3-C_6)$cycloalkyl, $(C_3-C_6)$cycloalkyloxy, $(C_1-C_6)$alkyloxy, $(C_3-C_6)$alkenyloxy, aryloxy, acyl, halogen, trifluoromethyl, difluoromethyl, cyano, nitro, hydroxy, carboxamide, amino, $(C_1-C_6)$aminoalkyl, $(C_1-C_6)$aminodialkyl, NHCOR$_{12}$ where $R_{12}$ is a $(C_1-C_6)$alkyl, $(C_1-C_6)$alkylaryl, aryl, or —CONR$_{13}$R$_{14}$ wherein $R_{13}$ and $R_{14}$, independently from each other, are selected from the group consisting of a hydrogen atom, an $(C_1-C_6)$alkyl group, $(C_3-C_6)$alkenyl group, an alkylaryl, an alkenylaryl, and an aryl group, $R_8$ represents a hydrogen atom or a OR$_{10}$ group, wherein $R_{10}$ is a hydrogen atom, an $(C_1-C_6)$alkyl, $(C_3-C_6)$cycloalkyl, $(C_3-C_6)$alkenyl, trifluoromethyl, difluoromethyl, an $(C_3-C_6)$alkenylaryl, aryl, or heterocyclic group, aromatic or not, having 1 to 3 heteroatoms chosen between O, N, S, when $R_{10}$ is an aryl, it is preferably mono or bis substituted by the following groups: an hydrogen, $(C_1-C_6)$alkyl, $(C_3-C_6)$cycloalkyl, $(C_3-C_6)$cycloalkyloxy, $(C_1-C_6)$alkyloxy, $(C_3-C_6)$alkenyloxy, halogen, trifluoromethyl, difluoromethyl, cyano, nitro, hydroxy, carboxamide, amino, $(C_1-C_6)$aminoalkyl, $(C_1-C_6)$aminodialkyl, NCOR$_{12}$ where $R_{12}$ is a $(C_1-C_6)$alkyl, $(C_1-C_6)$alkylaryl, aryl, and —CONR$_{13}$R$_{14}$ wherein $R_{13}$ and $R_{14}$, independently from each other, are selected from the group consisting of a hydrogen atom, an $(C_1-C_6)$alkyl group, $(C_3-C_6)$alkenyl group, an alkylaryl, an alkenylaryl, and an aryl group, $R_X$ represents an hydrogen atom, an halogen atom, a methyl, a methoxy, an acetyl, a trifluoromethyl, CN, COH or CONH$_2$ group, $R_Y$ represents an hydrogen, halogen atom, $(C_1-C_6)$alkyl, $(C_3-C_6)$cycloalkyl, aryl, arylalkyl, $(C_3-C_6)$cycloalkyloxy, COH, $(C_1-C_6)$alkyloxy, alkenyl, $(C_3-C_8)$alkenyloxy, alkynyl, alkynyloxy, acyl, halogen, trifluoromethyl, difluoromethyl, trifluoromethoxy, difluoromethoxy, cyano, nitro, hydroxy, carboxamide, amino, $(C_1-C_6)$aminoalkyl, $(C_1-C_6)$aminodialkyl, NHCOR$_{12}$ where $R_{12}$ is a $(C_1-C_6)$alkyl, $(C_1-C_6)$alkyloxy, hydroxy, $(C_1-C_6)$alkylaryl, aryl, or —CONR$_{13}$R$_{14}$ wherein $R_{13}$ and $R_{14}$, independently from each other, are selected from the group consisting of a hydrogen atom, an $(C_1-C_6)$alkyl group, an $(C_2-C_6)$alkenyl group, an alkynyl, an alkylaryl, an alkenylaryl, an alkynylaryl, and an aryl group, with the proviso that when $R_8$ is an hydrogen atom, then $R_X$ or $R_Y$ is different from hydrogen, or a pharmaceutically acceptable salt thereof.

The present invention also relates to pharmaceutical compositions comprising at least one compound as defined above in a pharmaceutically acceptable vehicle or support, optionally in association with another active agent.

The pharmaceutical composition is more particularly intended to treat diseases associated with abnormal regulation of intracellular cAMP and/or cGMP rate.

The present invention also relates to the use of a compound as defined above, for the preparation of a pharmaceutical composition for the treatment of diseases associated with abnormal regulation of intracellular cAMP and/or cGMP rate.

The present invention also includes methods of treating diseases associated with dysregulation of intracellular cAMP and/or cGMP rate, comprising the administration to a subject in need thereof of an effective amount of a compound as defined above.

Within the context of the present application, the alkyl groups may be linear or branched saturated groups containing from 1 to 10 carbon atoms. Examples of alkyl groups having from 1 to 10 carbon atoms inclusive are methyl, ethyl, propyl, isopropyl, t-butyl, n-butyl, pentyl, hexyl, heptyl, octyl, nonyl, decyl, 2-ethylhexyl, 2-methylbutyl, 2-methylpentyl, 1-methylhexyl, 3-methylheptyl and the other isomeric forms thereof. Preferably, the alkyl groups have from 1 to 6 carbon atoms. The alkyl groups can be susbstituted as described below, for instance by aryl or alkoxy group.

The term alkoxy denotes an alkyl group as defined above attached to the rest of the molecule by an oxygen atom.

The term alkenyl denotes linear or branched groups containing from 2 to 6 carbon atoms and presenting at least one C=C double bond. Examples of alkenyl groups include in particular the allyl group.

The term alkynyl denotes linear or branched groups containing from 2 to 8 carbon atoms and presenting at least one C=C triple bond. Examples of alkynyl groups include in particular the ethynyl, propynyl, butynyl, pentynyl, hexynyl group. Such group may be substituted as described below, in particular by alkoxy, NHCOR' or aryl as defined below.

The term aryl includes any aromatic group comprising from 6 to 18 carbon atoms, preferably from 6 to 14 carbon atoms. Most preferred aryl groups are mono- or bi-cyclic and comprises from 6 to 10 carbon atoms, such as phenyl, α-naphtyl, β-naphtyl.

Another most preferred aryl group is tricyclic and includes antracenyl, or fluorenyl group. When $R_7$ is an aryl group, it is preferably phenyl, 1-naphtyl, or 2-naphtyl groups.

The term heteroaryl includes any aromatic group comprising from 4 to 18 carbon atoms, preferably from 4 to 14 carbon atoms, and interrupted by one or several heteroatoms selected from N, O, S. Most preferred heteroaryl groups are thienyl, benzothienyl, benzofuryl, pyridyl, pyrimidinyl, pyridazinyl, isoquinolyl, quinolyl, thiazolyl, furyl, pyranyl, pyrrolyl, 2H-pyrrolyl, imidazolyl, benzymidazolyl, pyrazolyl, isothiazolyl, isoxazolyl and indolyl groups.

The term arylalkyl (or aryl($C_1$-$C_6$)alkyl) group generally stands for an aryl group attached to the molecule by an alkyl group as defined above, such as benzyl or phenethyl. The term ($C_1$-$C_6$)alkylaryl group generally stands for an alkyl group attached to the molecule by an aryl group as defined above.

The term <<cycloalkyl>> denotes a cyclic saturated hydrocarbonated system, having preferably from 3-6 carbon atoms, mono- or poly-cyclic. Typical examples of such groups are cyclopropyl, cyclobutyl, cyclopentyl or cyclohexyl group.

The term <<heterocycle>> includes any hydrocarbonated cycle, aromatic or not, having one or more cyclic heteroatoms. In particular, an heterocycle presents from 4 to 18 carbon atoms and one or more cyclic heteroatoms, such as N, O, or S. They include heteroaryl groups, such as thienyl, benzothienyl, benzofuryl, pyridyl, pyrimidinyl, pyridazinyl, isoquinolyl, quinolyl, thiazolyl, furyl, pyranyl, pyrrolyl, 2H-pyrrolyl, imidazolyl, benzimidazolyl, pyrazolyl, isothiazolyl, isoxazolyl, and indolyl groups. They also include non-aromatic heterocycles, such as morpholine, piperidine, piperazine, tetrahydrofuryl and pyrrolidine groups.

Halogen is understood to refer to fluorine, chlorine, bromine or iodine.

Heteroatom is understood to refer to O, N et S.

The term "acyl" denotes a radical of general formula RCO, wherein R represents an alkyl, alkenyl, aryl, heteroaryl, cycloalkyl, or heterocycle groups as defined above. In particular, the acyl group is an acetyl group.

The groups identified above may be substituted with at least one substituent, identical or different, preferably selected in the group consisting of an halogen atom, alkyl, halogenoalkyl, cycloalkyl, alkenyl, alkynyl, aralkyl, aryl, heterocycle, heterocycloalkyl, OH, =O, $NO_2$, CN, $CF_3$, COR', COOR', ($C_1$-$C_6$)alkoxy, —NR'R", —NHCOR' and —CONR'R" groups, wherein R' and R" represent, independently from each other, are selected from the group consisting of a hydrogen atom, an alkyl group having from 1 to 10 carbon atoms, an alkoxy having from 1 to 10 carbon atoms, an aryl, an aralkyl group, ($C_3$-$C_6$)alkenyl, an alkylaryl and an ($C_3$-$C_6$)alkenylaryl.

According to a particular embodiment, the compounds according to the invention correspond to general formula (I) and when $R_X$ or $R_Y$ is halogen, it is not on position 2 of the phenyl.

According to a preferred embodiment, the compounds according to the invention correspond to general formula (I) wherein $R_8$ is an hydrogen atom, alkoxy, preferably a methoxy or ethoxy, or aryloxy, preferably phenoxy group.

According to another preferred embodiment, the compounds according to the invention correspond to general formula (I), wherein at least one of $R_X$ and $R_Y$ is different from hydrogen.

According to a more particular aspect of the invention, the compounds according to the invention correspond to general formula (I), wherein both $R_X$ and $R_Y$ are different from hydrogen. According to this particular embodiment, Rx or Ry is selected in the group consisting of: halogen, alkyl, preferably methyl, and alkoxy, preferably methoxy, and the other Ry or Rx is selected in the group consisting of: halogen, NO2, and alkoxy, preferably methoxy.

According to another particular aspect of the invention, the compounds according to the invention correspond to general formula (I) wherein one of $R_X$ and $R_Y$ is an hydrogen atom and the other one is different from hydrogen. More particularly, $R_Y$ is an hydrogen atom and $R_X$ is different from hydrogen.

According to another aspect of the invention, the compounds according to the invention correspond to general formula (I) wherein one of $R_X$ and $R_Y$, different from hydrogen, is on position 3 of the phenyl group represented in formula (I). In that respect, Rx or Ry is preferably selected in the group consisting of: CN, NO2, NH2, COH, COCH3 (or acetyl), halogen (Br, Cl, F), CF3, OCH3, substituted or not alkynyl, arylalkyl, and alkoxyalkyl.

According to another aspect of the invention, the compounds according to the invention correspond to general formula (I) wherein one of $R_X$ and $R_Y$, different from hydrogen, is on position 4 of the phenyl group represented in formula (I). In that respect, Rx or Ry is preferably selected in the group consisting of: halogen atom (Br, Cl, F), substituted or not alkyl, preferably methyl, substituted or not alkynyl, trifluoromethoxy, and alkoxy, preferably methoxy. According to a particular embodiment, Ry represents methoxy on position 4 of the phenyl group represented in formula (I).

According to another aspect of the invention, the compounds according to the invention correspond to general formula (I) wherein $R_X$, different from hydrogen, is on position 3 of the phenyl group represented in formula (I).

According to another aspect of the invention, the compounds according to the invention correspond to general formula (I) wherein $R_X$ represents $CONH_2$, CN group, COCH3, preferably on position 3 or 4 of the phenyl group represented in formula (I).

According to another embodiment, the compounds according to the invention correspond to formula (I) wherein $R_Y$ represents H, an halogen atom, $CF_3$, ($C_1$-$C_6$)aminoalkyl, ($C_1$-$C_6$)aminodialkyl, —$NHCOR_{12}$, —$CONH_2$, a ($C_1$-$C_6$)alkyloxy group or a ($C_1$-$C_6$)alkyl group, preferably hydrogen.

According to another particular embodiment, when Ry represents an alkynyl group, the triple bond thereof is attached directly to the phenyl group, as illustrated by compounds of examples 66, 67, 95, 96, 97, 98 and 105.

According to a preferred embodiment, the compounds according to the invention correspond to general formula (I) wherein $R_1$ represents an hydrogen atom, an alkyl group, preferably methyl, ethyl, or propyl, an alkenyl group, preferably propenyl, or arylalkyl group. According to the most preferred embodiment, $R_1$ represents an hydrogen atom or a methyl group.

According to a preferred embodiment, when the compounds according to the invention correspond to general formula (I) wherein $R_7$ is a furan group, said group is preferably a furan-2-yl. When $R_7$ is a furan group, said group is preferably not substituted.

According to another preferred embodiment, the compounds according to the invention correspond to general formula (I) wherein $R_7$ is an unsubstituted aryl group, preferably unsubstituted phenyl group.

According to another aspect, the compounds according to the invention correspond to general formula (I) wherein $R_7$ is a substituted aryl or heteroaryl group, preferably a substituted phenyl group. In particular, said substituted aryl or heteroaryl group is substituted with one or two, identical or different, substituents. Said substituents are preferably selected in the group consisting of halogen, amino, aminoacyl (or $NHCOR_{12}$ as defined above), $CONH_2$, $(C_1-C_6)$alkyl, aryloxy, and $(C_1-C_6)$alkyloxy. The alkoxy group is preferably a methoxy or ethoxy group. In particular, the substituted phenyl group $R_7$ is at least substituted by one group on position ortho, which is preferably an alkoxy group.

In particular, the substituted phenyl group $R_7$ is selected in the group consisting of 4-methoxy-phenyl, 4-fluoro-phenyl, 2-methoxy-phenyl, 2-chloro-phenyl, 4-chloro-phenyl, 3-chloro-phenyl, 3-methoxy-phenyl, 2,5-dimethoxy-phenyl, 2,6-dimethoxy-phenyl, 4-benzamide, 4-cyanophenyl, 2,4-dimethoxy-phenyl, 4-carboxamide-phenyl, 4-acetyl-phenyl, 2-isopropoxy-phenyl, 2-phenoxy-phenyl, and 3,4-dimethoxy-phenyl groups.

When the compounds according to the invention are in the forms of salts, they are preferably pharmaceutically acceptable salts. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, perchloric, boric, nitric acids, and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, and in Handbook of Pharmaceutical Salts: Properties, Selection, and Use edited by P. Heinrich Stahl and Camille G. Wermuth 2002, which are incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamineoline and the like.

Specific examples of compounds of formula (I) which fall within the scope of the present invention include the following compounds:

3-(8-Methoxy-1-methyl-2-oxo-7-phenyl-2,3-dihydro-1H-benzo[e][1,4]diazepin-5-yl)-benzonitrile
3-[7-(4-Fluoro-phenyl)-8-methoxy-1-methyl-2-oxo-2,3-dihydro-1H-benzo[e][1,4]diazepin-5-yl]-benzonitrile
3-[8-Methoxy-7-(2-methoxy-phenyl)-1-methyl-2-oxo-2,3-dihydro-1H-benzo[e][1,4]diazepin-5-yl]-benzonitrile
3-[8-Methoxy-7-(4-methoxy-phenyl)-1-methyl-2-oxo-2,3-dihydro-1H-benzo[e][1,4]diazepin-5-yl]-benzonitrile
3-[7-(2-Chloro-phenyl)-8-methoxy-1-methyl-2-oxo-2,3-dihydro-1H-benzo[e][1,4]diazepin-5-yl]-benzonitrile
3-[7-(3-Chloro-phenyl)-8-methoxy-1-methyl-2-oxo-2,3-dihydro-1H-benzo[e][1,4]diazepin-5-yl]-benzonitrile
3-[7-(4-Chloro-phenyl)-8-methoxy-1-methyl-2-oxo-2,3-dihydro-1H-benzo[e][1,4]diazepin-5-yl]-benzonitrile
3-(7-Furan-2-yl-8-methoxy-1-methyl-2-oxo-2,3-dihydro-1H-benzo[e][1,4]diazepin-5-yl)-benzonitrile
3-(1-Methyl-2-oxo-7-phenyl-2,3-dihydro-1H-benzo[e][1,4]diazepin-5-yl)-benzonitrile
3-[8-Methoxy-7-(2-methoxy-phenyl)-2-oxo-2,3-dihydro-1H-benzo[e][1,4]diazepin-5-yl]-benzonitrile
3-(1-Methyl-2-oxo-7-phenyl-2,3-dihydro-1H-benzo[e][1,4]diazepin-5-yl)-benzonitrile
3-[7-(2-Methoxy-phenyl)-1-methyl-2-oxo-2,3-dihydro-1H-benzo[e][1,4]diazepin-5-yl]-benzonitrile
3-[7-(3-Methoxy-phenyl)-1-methyl-2-oxo-2,3-dihydro-1H-benzo[e][1,4]diazepin-5-yl]-benzonitrile
3-[7-(4-Methoxy-phenyl)-1-methyl-2-oxo-2,3-dihydro-1H-benzo[e][1,4]diazepin-5-yl]-benzonitrile
3-[7-(2,5-Dimethoxy-phenyl)-1-methyl-2-oxo-2,3-dihydro-1H-benzo[e][1,4]diazepin-5-yl]-benzonitrile
3-[7-(2,6-Dimethoxy-phenyl)-1-methyl-2-oxo-2,3-dihydro-1H-benzo[e][1,4]diazepin-5-yl]-benzonitrile
3-[7-(2,4-Dimethoxy-phenyl)-1-methyl-2-oxo-2,3-dihydro-1H-benzo[e][1,4]diazepin-5-yl]-benzonitrile
8-Ethoxy-1-ethyl-5,7-diphenyl-1,3-dihydro-benzo[e][1,4]diazepin-2-one
3-(8-Methoxy-1-methyl-2-oxo-7-phenyl-2,3-dihydro-1H-benzo[e][1,4]diazepin-5-yl)-benzamide
3-[7-(4-Fluoro-phenyl)-8-methoxy-1-methyl-2-oxo-2,3-dihydro-1H-benzo[e][1,4]diazepin-5-yl]-benzamide
3-[8-Methoxy-7-(2-methoxy-phenyl)-1-methyl-2-oxo-2,3-dihydro-1H-benzo[e][1,4]diazepin-5-yl]-benzamide
3-[8-Methoxy-7-(4-methoxy-phenyl)-1-methyl-2-oxo-2,3-dihydro-1H-benzo[e][1,4]diazepin-5-yl]-benzamide
3-[7-(2-Chloro-phenyl)-8-methoxy-1-methyl-2-oxo-2,3-dihydro-1H-benzo[e][1,4]diazepin-5-yl]-benzamide
3-[7-(3-Chloro-phenyl)-8-methoxy-1-methyl-2-oxo-2,3-dihydro-1H-benzo[e][1,4]diazepin-5-yl]-benzamide
3-[7-(4-Chloro-phenyl)-8-methoxy-1-methyl-2-oxo-2,3-dihydro-1H-benzo[e][1,4]diazepin-5-yl]-benzamide
3-(7-Furan-2-yl-8-methoxy-1-methyl-2-oxo-2,3-dihydro-1H-benzo[e][1,4]diazepin-5-yl)-benzamide
3-(1-methyl-2-oxo-7-phenyl-2,3-dihydro-1H-benzo[e][1,4]diazepin-5-yl)-benzamide
3-[7-(2-methoxy-phenyl)-1-methyl-2-oxo-2,3-dihydro-1H-benzo[e][1,4]diazepin-5-yl]-benzamide
3-[7-(3-methoxy-phenyl)-1-methyl-2-oxo-2,3-dihydro-1H-benzo[e][1,4]diazepin-5-yl]-benzamide 3-[7-(4-methoxy-phenyl)-1-methyl-2-oxo-2,3-dihydro-1H-benzo[e][1,4]diazepin-5-yl]-benzamide
3-[7-(2,5-Dimethoxy-phenyl)-1-methyl-2-oxo-2,3-dihydro-1H-benzo[e][1,4]diazepin-5-yl]-benzamide
3-[7-(2,6-Dimethoxy-phenyl)-1-methyl-2-oxo-2,3-dihydro-1H-benzo[e][1,4]diazepin-5-yl]-benzamide
3-[7-(2,4-Dimethoxy-phenyl)-1-methyl-2-oxo-2,3-dihydro-1H-benzo[e][1,4]diazepin-5-yl]-benzamide
3-(8-Methoxy-7-(4-benzamide)-1-methyl-2-oxo-2,3-dihydro-1H-benzo[e][1,4]diazepin-5-yl)-benzamide
3-[1-Hexyl-8-methoxy-7-(2-methoxy-phenyl)-2-oxo-2,3-dihydro-1H-benzo[e][1,4]diazepin-5-yl]-benzonitrile
3-[8-Methoxy-7-(2-methoxy-phenyl)-2-oxo-2,3-dihydro-1H-benzo[e][1,4]diazepin-5-yl]-benzamide
3-[8-Methoxy-7-(2-methoxy-phenyl)-2-oxo-1-propyl-2,3-dihydro-1H-benzo[e][1,4]diazepin-5-yl]-benzonitrile
3-[8-Methoxy-7-(2-methoxy-phenyl)-2-oxo-1-phenethyl-2,3-dihydro-1H-benzo[e][1,4]diazepin-5-yl]-benzonitrile
3-[1-Benzyl-8-methoxy-7-(2-methoxy-phenyl)-2-oxo-2,3-dihydro-1H-benzo[e][1,4]diazepin-5-yl]-benzonitrile
5-(3-Chloro-phenyl)-1-methyl-7-phenyl-1,3-dihydro-benzo[e][1,4]diazepin-2-one
5-(2-Chloro-phenyl)-1-methyl-7-phenyl-1,3-dihydro-benzo[e][1,4]diazepin-2-one
5-(4-Chloro-phenyl)-1-methyl-7-phenyl-1,3-dihydro-benzo[e][1,4]diazepin-2-one
3-(8-Methoxy-1-methyl-2-oxo-7-(4-cyanophenyl)-2,3-dihydro-1H-benzo[e][1,4]diazepin-5-yl)-benzonitrile.
3-[1-Benzyl-8-methoxy-7-(2-methoxy-phenyl)-2-oxo-2,3-dihydro-1H-benzo[e][1,4]diazepin-5-yl]-benzamide
3-[8-Methoxy-7-(2-methoxy-phenyl)-2-oxo-1-propyl-2,3-dihydro-1H-benzo[e][1,4]diazepin-5-yl]-benzamide
3-[8-Methoxy-7-(2-methoxy-phenyl)-2-oxo-1-phenethyl-2,3-dihydro-1H-benzo[e][1,4]diazepin-5-yl]-benzamide
3-[1-Hexyl-8-methoxy-7-(2-methoxy-phenyl)-2-oxo-2,3-dihydro-1H-benzo[e][1,4]diazepin-5-yl]-benzamide
3-[7-(4-Acetyl-phenyl)-8-methoxy-1-methyl-2-oxo-2,3-dihydro-1H-benzo[e][1,4]diazepin-5-yl]-benzonitrile
3-[7-(4-Acetyl-phenyl)-8-methoxy-1-methyl-2-oxo-2,3-dihydro-1H-benzo[e][1,4]diazepin-5-yl]-benzamide
5-(4-Methoxy-phenyl)-1-methyl-7-phenyl-1,3-dihydro-benzo[e][1,4]diazepin-2-one
5-(2-Methoxy-phenyl)-1-methyl-7-phenyl-1,3-dihydro-benzo[e][1,4]diazepin-2-one
3-(7-Furan-2-yl-1-methyl-2-oxo-2,3-dihydro-1H-benzo[e][1,4]diazepin-5-yl)-benzonitrile
3-[7-(3,4-Dimethoxy-phenyl)-1-methyl-2-oxo-2,3-dihydro-1H-benzo[e][1,4]diazepin-5-yl]-benzonitrile
3-[7-(3,4-Dimethoxy-phenyl)-1-methyl-2-oxo-2,3-dihydro-1H-benzo[e][1,4]diazepin-5-yl]-benzamide
5-(3,5-Dichloro-phenyl)-1-methyl-7-phenyl-1,3-dihydro-benzo[e][1,4]diazepin-2-one
5-(3,4-Dichloro-phenyl)-1-methyl-7-phenyl-1,3-dihydro-benzo[e][1,4]diazepin-2-one
5-(4-Fluoro-phenyl)-1-methyl-7-phenyl-1,3-dihydro-benzo[e][1,4]diazepin-2-one
5-(3-Acetyl-phenyl)-1-methyl-7-phenyl-1,3-dihydro-benzo[e][1,4]diazepin-2-one
1-Methyl-7-phenyl-5-(3-trifluoromethyl-phenyl)-1,3-dihydro-benzo[e][1,4]diazepin-2-one
1-Methyl-5-(4-methyl-3-nitro-phenyl)-7-phenyl-1,3-dihydro-benzo[e][1,4]diazepin-2-one
1-Methyl-7-phenyl-5-(4-trifluoromethoxy-phenyl)-1,3-dihydro-benzo[e][1,4]diazepin-2-one
5-(3-Bromo-phenyl)-8-methoxy-1-methyl-7-phenyl-1,3-dihydro-benzo[e][1,4]diazepin-2-one
3-[7-(2-Isopropoxy-phenyl)-8-methoxy-1-methyl-2-oxo-2,3-dihydro-1H-benzo[e][1,4]diazepin-5-yl]-benzonitrile
5-(3,4-Dimethoxy-phenyl)-1-methyl-7-phenyl-1,3-dihydro-benzo[e][1,4]diazepin-2-one
1-Methyl-5-(3-nitro-phenyl)-7-phenyl-1,3-dihydro-benzo[e][1,4]diazepin-2-one
5-(3-Hex-1-ynyl-phenyl)-8-methoxy-1-methyl-7-phenyl-1,3-dihydro-benzo[e][1,4]diazepin-2-one
{3-[3-(8-Methoxy-1-methyl-2-oxo-7-phenyl-2,3-dihydro-1H-benzo[e][1,4]diazepin-5-yl)-phenyl]-prop-2-ynyl}-carbamic acid tert-butyl ester
5-(3-Amino-phenyl)-1-methyl-7-phenyl-1,3-dihydro-benzo[e][1,4]diazepin-2-one
3-(1-Methyl-2-oxo-8-phenoxy-7-phenyl-2,3-dihydro-1H-benzo[e][1,4]diazepin-5-yl)-benzonitrile
3-[7-(2-Methoxy-phenyl)-1-methyl-2-oxo-8-phenoxy-2,3-dihydro-1H-benzo[e][1,4]diazepin-5-yl]-benzonitrile
3-[7-(2-Chloro-phenyl)-1-methyl-2-oxo-8-phenoxy-2,3-dihydro-1H-benzo[e][1,4]diazepin-5-yl]-benzonitrile
3-(1-Methyl-2-oxo-8-phenoxy-7-phenyl-2,3-dihydro-1H-benzo[e][1,4]diazepin-5-yl)-benzamide
3-[7-(2-Chloro-phenyl)-1-methyl-2-oxo-8-phenoxy-2,3-dihydro-1H-benzo[e][1,4]diazepin-5-yl]-benzamide
3-[7-(2-Methoxy-phenyl)-1-methyl-2-oxo-8-phenoxy-2,3-dihydro-1H-benzo[e][1,4]diazepin-5-yl]-benzamide
7-(2,6-Dimethoxy-phenyl)-5-(4-methoxy-phenyl)-1-methyl-1,3-dihydro-benzo[e][1,4]diazepin-2-one
8-Methoxy-5-(4-methoxy-phenyl)-7-phenyl-1,3-dihydro-benzo[e][1,4]diazepin-2-one
7-(2,6-Dimethoxy-phenyl)-1-methyl-5-(4-methyl-3-nitro-phenyl)-1,3-dihydro-benzo[e][1,4]diazepin-2-one
3-[7-(2-Isopropoxy-phenyl)-8-methoxy-1-methyl-2-oxo-2,3-dihydro-1H-benzo[e][1,4]diazepin-5-yl]-benzamide
5-(3-Methoxy-phenyl)-1-methyl-7-phenyl-1,3-dihydro-benzo[e][1,4]diazepin-2-one
5-(3-Bromo-phenyl)-8-methoxy-7-phenyl-1,3-dihydro-benzo[e][1,4]diazepin-2-one
3-[7-(2-Chloro-6-methoxy-phenyl)-1-methyl-2-oxo-2,3-dihydro-1H-benzo[e][1,4]diazepin-5-yl]-benzonitrile
3-[7-(5-Chloro-2-methoxy-phenyl)-1-methyl-2-oxo-2,3-dihydro-1H-benzo[e][1,4]diazepin-5-yl]-benzonitrile
3-[7-(2-Chloro-6-methoxy-phenyl)-1-methyl-2-oxo-2,3-dihydro-1H-benzo[e][1,4]diazepin-5-yl]-benzamide
3-[7-(5-Chloro-2-methoxy-phenyl)-1-methyl-2-oxo-2,3-dihydro-1H-benzo[e][1,4]diazepin-5-yl]-benzamide
3-(2-Oxo-7-phenyl-8-trifluoromethoxy-2,3-dihydro-1H-benzo[e][1,4]diazepin-5-yl)-benzonitrile
3-(1-Methyl-2-oxo-7-phenyl-8-trifluoromethoxy-2,3-dihydro-1H-benzo[e][1,4]diazepin-5-yl)-benzonitrile
3-(1-Methyl-2-oxo-7-phenyl-8-trifluoromethoxy-2,3-dihydro-1H-benzo[e][1,4]diazepin-5-yl)-benzamide
3-[1-Methyl-2-oxo-7-(2-phenoxy-phenyl)-2,3-dihydro-1H-benzo[e][1,4]diazepin-5-yl]-benzonitrile
3-[7-(2,6-Dimethoxy-phenyl)-8-methoxy-1-methyl-2-oxo-2,3-dihydro-1H-benzo[e][1,4]diazepin-5-yl]-benzonitrile
3-[8-Methoxy-1-methyl-2-oxo-7-(2-phenoxy-phenyl)-2,3-dihydro-1H-benzo[e][1,4]diazepin-5-yl]-benzonitrile
3-[1-Methyl-2-oxo-7-(2-phenoxy-phenyl)-2,3-dihydro-1H-benzo[e][1,4]diazepin-5-yl]-benzamide
3-[7-(2,6-Dimethoxy-phenyl)-8-methoxy-1-methyl-2-oxo-2,3-dihydro-1H-benzo[e][1,4]diazepin-5-yl]-benzamide
3-[8-Methoxy-1-methyl-2-oxo-7-(2-phenoxy-phenyl)-2,3-dihydro-1H-benzo[e][1,4]diazepin-5-yl]-benzamide
8-Methoxy-1-methyl-7-phenyl-5-[3-(4-phenyl-butyl)-phenyl]-1,3-dihydro-benzo[e][1,4]diazepin-2-one
8-Methoxy-5-[3-(3-methoxy-prop-1-ynyl)-phenyl]-1-methyl-7-phenyl-1,3-dihydro-benzo[e][1,4]diazepin-2-one {3-[4-(8-Methoxy-1-methyl-2-oxo-7-phenyl-2,3-dihydro-1H-benzo[e][1,4]diazepin-5-yl)-phenyl]-prop-2-ynyl}-carbamic acid tert-butyl ester 8-Methoxy-1-methyl-7-phenyl-5-(4-phenylethynyl-phenyl)-1,3-dihydro-benzo[e][1,4]diazepin-2-one 8-Methoxy-5-[4-(3-methoxy-prop-1-ynyl)-phenyl]-1-methyl-7-phenyl-1,3-dihydro-benzo[e][1,4]diazepin-2-one 5-(3,4-Dichloro-phenyl)-7-(2,6-dimethoxy-phenyl)-1-methyl-1,3-dihydro-benzo[e][1,4]diazepin-2-one 7-(2,6-Dimethoxy-phenyl)-5-(4-fluoro-phenyl)-1-methyl-1,3-dihydro-benzo[e][1,4]diazepin-2-one 5-(3,4-Dimethoxy-phenyl)-7-(2,6-dimethoxy-phenyl)-1-methyl-1,3-dihydro-benzo[e][1,4]diazepin-2-one 5-(2-Bromo-phenyl)-8-methoxy-7-phenyl-1,3-dihydro-benzo[e][1,4]diazepin-2-one 8-Methoxy-5-[3-(3-methoxy-propyl)-phenyl]-1-methyl-7-phenyl-1,3-dihydro-benzo[e][1,4]diazepin-2-one 5-(2-Bromo-phenyl)-8-methoxy-1-methyl-7-phenyl-1,3-dihydro-benzo[e][1,4]diazepin-2-one 5-(4-Hex-1-ynyl-phenyl)-8-methoxy-1-methyl-7-phenyl-1,3-dihydro-benzo[e][1,4]diazepin-2-one 8-Methoxy-5-[4-(3-methoxy-propyl)-phenyl]-1-methyl-7-phenyl-1,3-dihydro-benzo[e][1,4]diazepin-2-one {3-[4-(8-Methoxy-1-methyl-2-oxo-7-phenyl-2,3-dihydro-1H-benzo[e][1,4]diazepin-5-yl)-phenyl]-propyl}-carbamic acid tert-butyl ester 8-Methoxy-5-(4-methoxy-phenyl)-7-(2-methoxy-phenyl)-1-methyl-1,3-dihydro-benzo[e][1,4]diazepin-2-one 7-(2,6-Dimethoxy-phenyl)-8-methoxy-5-(4-methoxy-phenyl)-1-methyl-1,3-dihydro-benzo[e][1,4]diazepin-2-one 7-(2,5-Dimethoxy-phenyl)-8-methoxy-5-(4-methoxy-phenyl)-1-methyl-1,3-dihydro-benzo[e][1,4]diazepin-2-one 7-(2-Fluoro-6-methoxy-phenyl)-8-methoxy-5-(4-methoxy-phenyl)-1-methyl-1,3-dihydro-benzo[e][1,4]diazepin-2-one 8-Methoxy-5-(4-methoxy-phenyl)-1-methyl-7-(2-phenoxy-phenyl)-1,3-dihydro-benzo[e][1,4]diazepin-2-one 5-(4-Bromo-phenyl)-8-methoxy-1-methyl-7-phenyl-1,3-dihydro-benzo[e][1,4]diazepin-2-one 5-(4-Bromo-phenyl)-8-methoxy-7-phenyl-1,3-dihydro-benzo[e][1,4]diazepin-2-one 7-(2,6-Dimethoxy-phenyl)-1-methyl-5-m-tolyl-1,3-dihydro-benzo[e][1,4]diazepin-2-one.

Particularly preferred compounds are 3-[7-(2,6-dimethoxy-phenyl)-1-methyl-2-oxo-2,3-dihydro-1H-benzo[e][1,4]diazepin-5-yl]-benzamide, 3-[7-(2,5-dimethoxy-phenyl)-1-methyl-2-oxo-2,3-dihydro-1H-benzo[e][1,4]diazepin-5-yl]-benzamide, 3-[8-methoxy-7-(4-methoxy-phenyl)-1-methyl-2-oxo-2,3-dihydro-1H-benzo[e][1,4]diazepin-5-yl]-benzamide, 3-[8-methoxy-7-(2-methoxy-phenyl)-1-methyl-2-oxo-2,3-dihydro-1H-benzo[e][1,4]diazepin-5-yl]-benzamide, 3-[7-(2-chloro-phenyl)-8-methoxy-1-methyl-2-oxo-2,3-dihydro-1H-benzo[e][1,4]diazepin-5-yl]-benzamide, 3-(8-methoxy-1-methyl-2-oxo-7-phenyl-2,3-dihydro-1H-benzo[e][1,4]diazepin-5-yl)-benzamide, 7-(2,6-Dimethoxy-phenyl)-5-(4-methoxy-phenyl)-1-methyl-1,3-dihydro-benzo[e][1,4]diazepin-2-one, 3-[7-(2-Chloro-6-methoxy-phenyl)-1-methyl-2-oxo-2,3-dihydro-1H-benzo[e][1,4]diazepin-5-yl]-benzamide, 3-[7-(2,6-Dimethoxy-phenyl)-8-methoxy-1-methyl-2-oxo-2,3-dihydro-1H-benzo[e][1,4]diazepin-5-yl]-benzamide, 3-[8-Methoxy-1-methyl-2-oxo-7-(2-phenoxy-phenyl)-2,3-dihydro-1H-benzo[e][1,4]diazepin-5-yl]-benzamide, 5-(3,4-Dichloro-phenyl)-7-(2,6-dimethoxy-phenyl)-1-methyl-1,3-dihydro-benzo[e][1,4]diazepin-2-one,7-(2,6-Dimethoxy-phenyl)-1-methyl-5-m-tolyl-1,3-dihydro-benzo[e][1,4]diazepin-2-one and 7-(2,6-Dimethoxy-phenyl)-8-methoxy-5-(4-methoxy-phenyl)-1-methyl-1,3-dihydro-benzo[e][1,4]diazepin-2-one.

Particularly most preferred compounds are 3-[7-(2,5-Dimethoxy-phenyl)-1-methyl-2-oxo-2,3-dihydro-1H-benzo[e][1,4]diazepin-5-yl]-benzamide, 3-[7-(2,6-Dimethoxy-phenyl)-1-methyl-2-oxo-2,3-dihydro-1H-benzo[e][1,4]diazepin-5-yl]-benzamide, 3-[7-(2,6-Dimethoxy-phenyl)-8-methoxy-1-methyl-2-oxo-2,3-dihydro-1H-benzo[e][1,4]diazepin-5-yl]-benzamide, 7-(2,6-Dimethoxy-phenyl)-5-(4-methoxy-phenyl)-1-methyl-1,3-dihydro-benzo[e][1,4]diazepin-2-one, 7-(2,6-Dimethoxy-phenyl)-5-(4-fluoro-phenyl)-1-methyl-1,3-dihydro-benzo[e][1,4]diazepin-2-one, and 7-(2,6-Dimethoxy-phenyl)-8-methoxy-5-(4-methoxy-phenyl)-1-methyl-1,3-dihydro-benzo[e][1,4]diazepin-2-one.

The compounds according to the present invention may be prepared by various methods known to those skilled in the art. Different chemical routes have been carried out and are described below.

Intermediates of general formula II, in which $R_8$ is $OCH_3$ or a OPh can be prepared using a method analogous to that reported in J. Med. Chem. 1989, Vol. 32, N°8, 1936-1942.

When $R_8$ is an ethoxy or an other alkoxy group, the synthesis of II could be performed starting from alkylation of 3-nitrophenol followed by reduction of the nitro group and then using the reference above.

When X is an aryl group and R8 is a methoxy group, the synthesis of II could be performed by a Suzuki coupling between 2-bromo-5-nitroanisole and a suitable boronic acid followed by reduction of the nitro group and then using the reference cited above.

Scheme 1

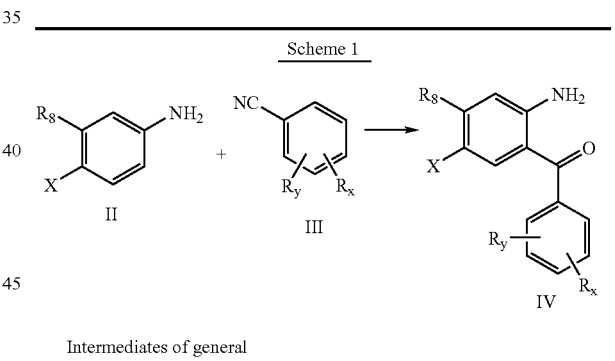

| Intermediates of general formula IV | X | $R_8$ | $R_x$ | $R_y$ |
|---|---|---|---|---|
| 1 | Br | $OCH_3$ | 3-CN | H |
| 2 | Br | H | 3-CN | H |
| 3 | I | H | 3-CN | H |
| 4 | Br | $OC_2H_5$ | H | H |
| 13 | Br | OPh | 3-CN | H |
| 16 | Ph | $OCH_3$ | 3-Br | H |
| 19 | Ph | $OCH_3$ | H | 4-$OCH_3$ |
| 20 | Ph | $OCF_3$ | 3-CN | H |
| 21 | Br | $OCH_3$ | 4-$OCH_3$ | H |

For $R_8$=H, the compounds II are commercially available.

The key intermediates of general formula IV can be obtained by a Sugasawa reaction (Scheme 1) from intermediates of general formula II, in which $R_8$ is as described above, and X is halogen and intermediates of general formula III, in which $R_X$ and $R_Y$ are as described above, in a suitable halogenated or aromatic solvent such as dichloromethane, trichloroethylenelorobenzene, toluene, xylene and most preferably 1,2-dichloroethane with a mixture of Lewis acid such as GaCl$_3$/BCl$_3$, InCl$_3$/BCl$_3$, FeCl$_3$/BCl$_3$, SbCl$_5$/BCl$_3$, AgOTf/BCl$_3$ and most preferably AlCl$_3$/BCl$_3$, followed by hydrolysis in HCl.

Scheme 2

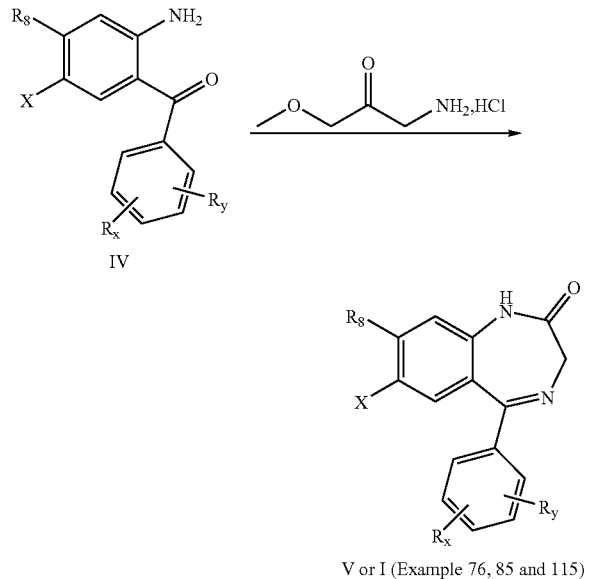

IV

V or I (Example 76, 85 and 115)

| | X | R$_8$ | R$_X$ | R$_Y$ |
|---|---|---|---|---|
| Intermediates of general formula V | | | | |
| 5 | Br | OCH$_3$ | 3-CN | H |
| 6 | Br | OC$_2$H$_5$ | H | H |
| 7 | I | H | 3-CN | H |
| 14 | Br | OPh | 3-CN | H |
| 22 | Br | OCH$_3$ | 4-OCH$_3$ | H |
| Example of general formula I | | | | |
| 76 | Ph | OCH$_3$ | H | 4-OCH$_3$ |
| 85 | Ph | OCF$_3$ | 3-CN | H |
| 115 | Ph | OCH$_3$ | 4-Br | H |

Intermediates of general formula V in which R$_8$, X and R$_X$ and R$_Y$ have the same meaning as above can be prepared by heating intermediates of general formula IV and ethyl glycinate hydrochloride in Pyridine (Scheme 2).

For Example 76, the meaning of X is the same as R$_7$.

Scheme 3

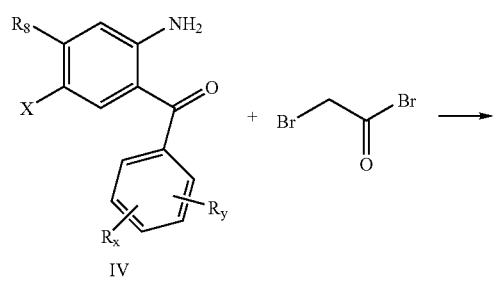

IV

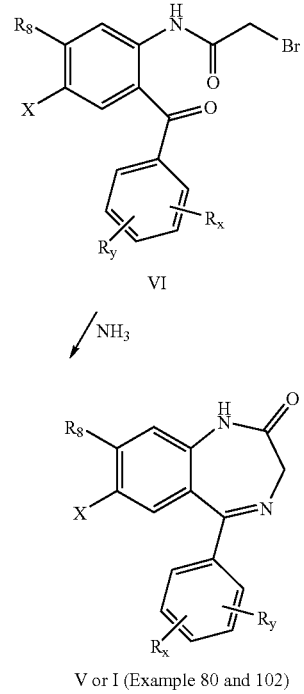

VI

V or I (Example 80 and 102)

| | X | R$_8$ | R$_X$ | R$_Y$ |
|---|---|---|---|---|
| Intermediates of general formula V | | | | |
| 8 | Br | H | 3-CN | H |
| Example of general formula I | | | | |
| 80 | Ph | OCH$_3$ | 3-Br | H |
| 102 | Ph | OCH3 | 2-Br | H |

An alternative synthesis of intermediates of general formula V in which R$_8$ and R'$_3$ have the same meaning as above can also be performed in two steps by treating intermediates of general formula IV with bromoacetyl bromide (Scheme 3), followed by ammonia.

For Example 80, the meaning of X is the same as R$_7$.

Scheme 4

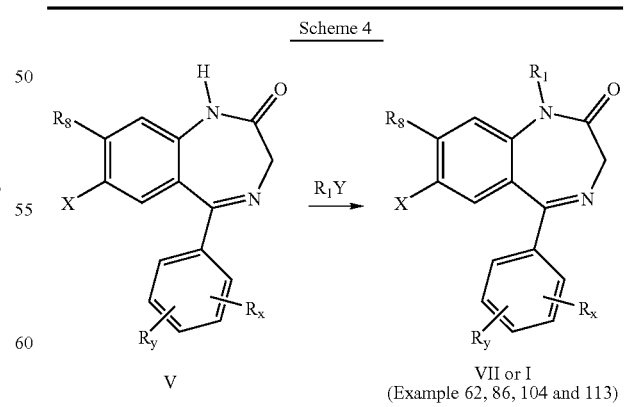

V

VII or I
(Example 62, 86, 104 and 113)

| Intermediates of general formula VII | X | R$_8$ | R$_X$ | R$_Y$ | R$_1$ |
|---|---|---|---|---|---|
| 9 | Br | OCH$_3$ | 3-CN | H | CH$_3$ |
| 10 | Br | H | 3-CN | H | CH$_3$ |

| | | | -continued | | |
|---|---|---|---|---|---|
| 11 | I | H | 3-CN | H | $CH_3$ |
| 12 | Br | $OC_2H_5$ | H | H | $C_2H_5$ |
| 15 | Br | $OC_2H_5$ | H | H | $C_2H_5$ |
| 23 | Br | $OCH_3$ | 4-$OCH_3$ | H | $CH_3$ |

| Example of general formula I | X | $R_8$ | RX | RY | $R_1$ |
|---|---|---|---|---|---|
| 62 | Ph | $OCH_3$ | 3-Br | H | $CH_3$ |
| 86 | Ph | $OCF_3$ | 3-CN | H | $CH_3$ |
| 104 | Ph | OMe | 2-Br | H | $CH_3$ |
| 113 | Ph | OMe | 4-Br | H | $CH_3$ |

Compounds of general formula VII, in which $R_8$ and $R_X$ are as described above can be obtained by using an alkylating agent of general formula $R_1Y$, in which $R_1$ is as described above, and Y can be a suitable leaving group such as a chlorine, bromine, iodine, mesylate and tosylate, in phase transfer conditions. The reaction can be carried out in a suitable solvent such as halogenated hydrocarbons, toluene at room temperature or at boiling point.

For Example 62, the meaning of X is the same as $R_7$.

Scheme 5

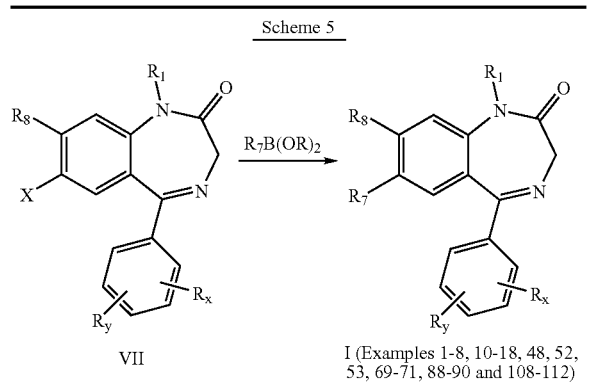

VII → I (Examples 1-8, 10-18, 48, 52, 53, 69-71, 88-90 and 108-112)

| Examples of general formula I | $R_8$ | $R_X$ | $R_1$ | $R_7$ | RY |
|---|---|---|---|---|---|
| 1 | $OCH_3$ | 3-CN | $CH_3$ | Ph | H |
| 2 | $OCH_3$ | 3-CN | $CH_3$ | 4-FPh | H |
| 3 | $OCH_3$ | 3-CN | $CH_3$ | 2-MeOPh | H |
| 4 | $OCH_3$ | 3-CN | $CH_3$ | 4-MeOPh | H |
| 5 | $OCH_3$ | 3-CN | $CH_3$ | 2-ClPh | H |
| 6 | $OCH_3$ | 3-CN | $CH_3$ | 3-ClPh | H |
| 7 | $OCH_3$ | 3-CN | $CH_3$ | 4-ClPh | H |
| 8 | $OCH_3$ | 3-CN | $CH_3$ | Furo-2-yl | H |
| 10 | $OCH_3$ | 3-CN | H | 2-MeOPh | H |
| 11 | H | 3-CN | $CH_3$ | Ph | H |
| 12 | H | 3-CN | $CH_3$ | 2-MeOPh | H |
| 13 | H | 3-CN | $CH_3$ | 3-MeOPh | H |
| 14 | H | 3-CN | $CH_3$ | 4-MeOPh | H |
| 15 | H | 3-CN | $CH_3$ | 2,5-DiMeOPh | H |
| 16 | H | 3-CN | $CH_3$ | 2,6-DiMeOPh | H |
| 17 | H | 3-CN | $CH_3$ | 2,4-DiMeOPh | H |
| 18 | $OC_2H_5$ | H | $C_2H_5$ | Ph | H |
| 43 | $OCH_3$ | 3-CN | $CH_3$ | 4-CNPh | H |
| 48 | $OCH_3$ | 3-CN | $CH_3$ | 4-$CH_3$COPh | H |
| 52 | H | 3-CN | $CH_3$ | Furo-2-yl | H |
| 53 | H | 3-CN | $CH_3$ | 3,4-DiMeOPh | H |
| 63 | $OCH_3$ | 3-CN | $CH_3$ | 2-$(CH_3)_2$CHOPh | H |
| 69 | OPh | 3-CN | $CH_3$ | Ph | H |
| 70 | Ph | 3-CN | $CH_3$ | O-(2-MeO)Ph | H |
| 71 | Ph | 3-CN | $CH_3$ | O-(2-Cl)Ph | H |
| 81 | H | 3-CN | $CH_3$ | (2-Cl,6-MeO)Ph | H |
| 82 | H | 3-CN | $CH_3$ | (5-Cl,2-MeO)Ph | H |
| 88 | H | 3-CN | $CH_3$ | (2-PhO)Ph | H |
| 89 | $OCH_3$ | 3-CN | $CH_3$ | 2,6-DiMeOPh | H |
| 90 | $OCH_3$ | 3-CN | $CH_3$ | (2-PhO)Ph | H |
| 108 | $OCH_3$ | 4-$OCH_3$ | $CH_3$ | (2-$OCH_3$)Ph | H |
| 109 | $OCH_3$ | 4-$OCH_3$ | $CH_3$ | (2,6-DiMeO)Ph | H |
| 110 | $OCH_3$ | 4-$OCH_3$ | $CH_3$ | (2,5-DiMeO)Ph | H |
| 111 | $OCH_3$ | 4-$OCH_3$ | $CH_3$ | (2-F,6-OMe)Ph | H |
| 112 | $OCH_3$ | 4-$OCH_3$ | $CH_3$ | (2-PhO)Ph | H |

Compounds of general formula I can be prepared by using a Palladium catalysed cross-coupling between compounds VII, in which $R_8$ and $R_X$ are as described above, (scheme 5) and boronic acids or esters $R_7B(OR)_2$, in which $R_7$ has the meaning as described above and R represents H, alkoxy or both R form with the boron atom and oxygen atoms a 6-membered ring.

X is an halogen atom, preferably bromine or iodine.

Scheme 6

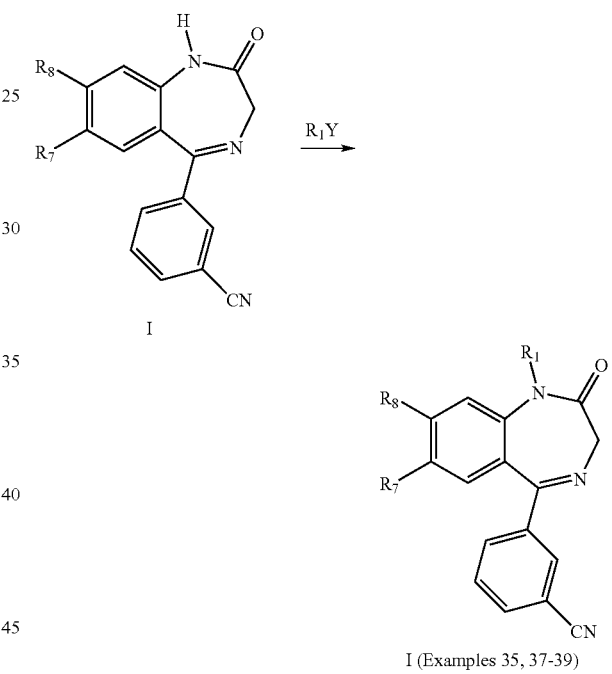

I (Examples 35, 37-39)

When $R_1$ is an hydrogen, compounds of general formula (I) can be converted in another series of general formula (I) by using an alkylating agent of general formula $R_1Y$, in which $R_1$ is as described above, and Y can be a suitable leaving group such as a chlorine, bromine, iodine, mesylate and tosylate, in phase transfer conditions. The reaction can be carried out in a suitable solvent such as halogenated hydrocarbons, toluene at room temperature or at boiling point.

| Examples of general formula I | $R_8$ | $R_1$ | $R_7$ |
|---|---|---|---|
| 35 | $OCH_3$ | hexyl | 2-MeOPh |
| 37 | $OCH_3$ | propyl | 2-MeOPh |
| 38 | $OCH_3$ | $(CH_2)_2$Ph | 2-MeOPh |
| 39 | $OCH_3$ | $CH_2$Ph | 2-MeOPh |

Scheme 7

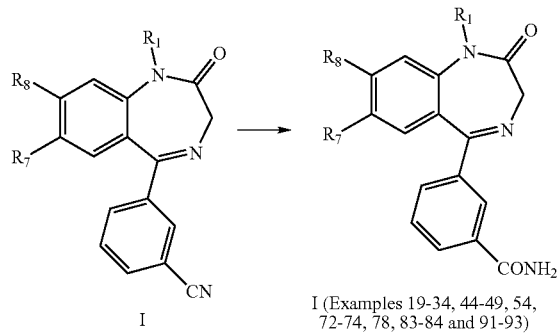

I (Examples 19-34, 44-49, 54, 72-74, 78, 83-84 and 91-93)

Examples of general formula I

| | $R_8$ | $R_1$ | $R_7$ |
|---|---|---|---|
| 19 | $OCH_3$ | $CH_3$ | Ph |
| 20 | $OCH_3$ | $CH_3$ | 4-FPh |
| 21 | $OCH_3$ | $CH_3$ | 2-MeOPh |
| 22 | $OCH_3$ | $CH_3$ | 4-MeOPh |
| 23 | $OCH_3$ | $CH_3$ | 2-ClPh |
| 24 | $OCH_3$ | $CH_3$ | 3-ClPh |
| 25 | $OCH_3$ | $CH_3$ | 4-ClPh |
| 26 | $OCH_3$ | $CH_3$ | Furo-2-yl |
| 27 | H | $CH_3$ | Ph |
| 28 | H | $CH_3$ | 2-MeOPh |
| 29 | H | $CH_3$ | 3-MeOPh |
| 30 | H | $CH_3$ | 4-MeOPh |
| 31 | H | $CH_3$ | 2,5-DiMeOPh |
| 32 | H | $CH_3$ | 2,6-DiMeOPh |
| 33 | H | $CH_3$ | 2,4-DiMeOPh |
| 34 | $OCH_3$ | $CH_3$ | 4-$CONH_2$Ph |
| 36 | $OCH_3$ | H | 2-$OCH_3$Ph |
| 44 | $OCH_3$ | $PhCH_2$ | 2-MeOPh |
| 45 | $OCH_3$ | $CH3(CH_2)_2$ | 2-MeOPh |
| 46 | $OCH_3$ | $Ph(CH_2)_2$ | 2-MeOPh |
| 47 | $OCH_3$ | $CH_3(CH_2)_5$ | 2-MeOPh |
| 49 | $OCH_3$ | $CH_3$ | 4-$COCH_3$Ph |
| 54 | H | $CH_3$ | 3,4-DiMeOPh |
| 72 | PhO | $CH_3$ | Ph |
| 73 | PhO | $CH_3$ | 2-ClPh |
| 74 | PhO | $CH_3$ | 2-MeOPh |
| 78 | $OCH_3$ | $CH_3$ | 2-$(CH_3)_2$CHOPh |
| 83 | H | $CH_3$ | (2-Cl,6-MeO)Ph |
| 84 | H | $CH_3$ | (5-Cl,2-MeO)Ph |
| 87 | $OCF_3$ | $CH_3$ | Ph |
| 91 | H | $CH_3$ | (2-PhO)Ph |
| 92 | $OCH_3$ | $CH_3$ | 2,6-DiMeOPh |
| 93 | $OCH_3$ | $CH_3$ | (2-PhO)Ph |

Compounds of general formula I (examples 19-34 and 36), in which $R_8$, $R_1$ have the same meaning as above and $R_X$ is an amide can be prepared by oxidation with hydrogen peroxide and sodium hydroxide (0.5 M) in ethanol at room temperature or 60° C. from compounds of general formula I in which $R'_3$ is a cyano.

Alternatively compounds I (examples 19-34 and 36) in which $R_8$, $R_1$ have the same meaning as above and $R_X$ is an amide could also be prepared using sulphuric acid at a temperature between 20° C. and 100° C. from compounds of general formula I in which $R_X$ is a cyano.

Scheme 8

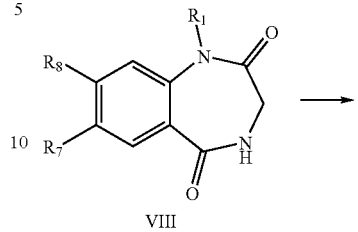

VIII

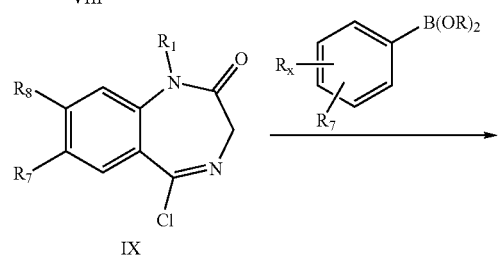

IX

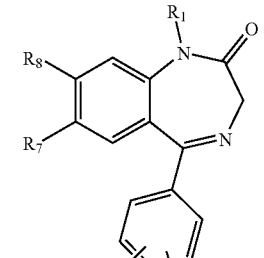

I (Examples 9, 40-42, 50-61, 64-65, 68, 75, 77, 79 and 99-101, 115)

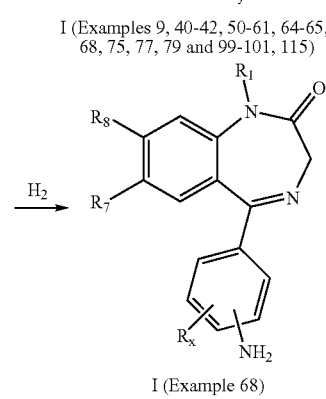

I (Example 68)

Examples of general formula I

| | $R_8$ | $R_7$ | $R_X$ | $R_Y$ | $R_1$ |
|---|---|---|---|---|---|
| 9 | H | Ph | 3-CHO | H | $CH_3$ |
| 40 | H | Ph | 3-Cl | H | $CH_3$ |
| 41 | H | Ph | 2-Cl | H | $CH_3$ |
| 42 | H | Ph | 4-Cl | H | $CH_3$ |
| 50 | H | Ph | H | 4-$OCH_3$ | $CH_3$ |
| 51 | H | Ph | H | 2-$OCH_3$ | $CH_3$ |
| 55 | H | Ph | 3-Cl | 5-Cl | $CH_3$ |
| 56 | H | Ph | 3-Cl | 4-Cl | $CH_3$ |
| 57 | H | Ph | 4-F | H | $CH_3$ |
| 58 | H | Ph | H | 3-$COCH_3$ | $CH_3$ |
| 59 | H | Ph | 3-$CF_3$ | H | $CH_3$ |
| 60 | H | Ph | 4-$CH_3$ | 3-$NO_2$ | $CH_3$ |
| 61 | H | Ph | H | 3-$OCF_3$ | $CH_3$ |
| 64 | H | Ph | 3-$OCH_3$ | 4-$OCH_3$ | $CH_3$ |
| 65 | H | Ph | H | $NO_2$ | $CH_3$ |
| 68 | H | Ph | H | $NH_2$ | $CH_3$ |
| 75 | H | (2,6-DiMeO)Ph | H | 4-$OCH_3$ | $CH_3$ |

-continued

| | | | | | |
|---|---|---|---|---|---|
| 77 | H | (2,6-DiMeO)Ph | 4-CH$_3$ | 3-NO$_2$ | CH$_3$ |
| 79 | H | Ph | 3-OCH$_3$ | H | CH$_3$ |
| 99 | H | (2,6-DiMeO)Ph | 3-Cl | 4-Cl | CH$_3$ |
| 100 | H | (2,6-DiMeO)Ph | 4-F | H | CH$_3$ |
| 101 | H | (2,6-DiMeO)Ph | 4-OCH$_3$ | 3-OCH$_3$ | CH$_3$ |
| 115 | H | (2,6-DiMeO)Ph | 3-CH$_3$ | H | CH$_3$ |

Compounds of general formula VIII, in which R$_8$ and R$_1$ are as described above can be obtained using the procedure describe in J. Med. Chem. 42, 5241-5253 (1999).

Compounds of general formula IX, in which R$_8$ and R$_1$ are as described above can be obtained by reacting compound of general formula VIII with POCl$_3$ and dimethylaniline in an halogenate solvent such as dichloromethane, 1,2-dichloroethane chlorobenzene and most preferably chloroform in a sealed tube at a temperature between 80° C. to 130° C.

Compounds of general formula I can be prepared by using a Palladium catalysed cross-coupling between compounds IX, in which R$_8$ and R$_1$ are as described above, (scheme 7) and boronics acids or esters R$_X$R$_Y$PhB(OR)$_2$, in which R$_X$ and R$_Y$ have the meaning as described above and R represents H, alkoxy or both R form with the boron atom and oxygen atoms a 6-membered ring, X is an halogen atom, preferably chlorine.

Nitro compounds of general formula I was reduced by Palladium catalysed hydrogenation to provide amino group (Example 68).

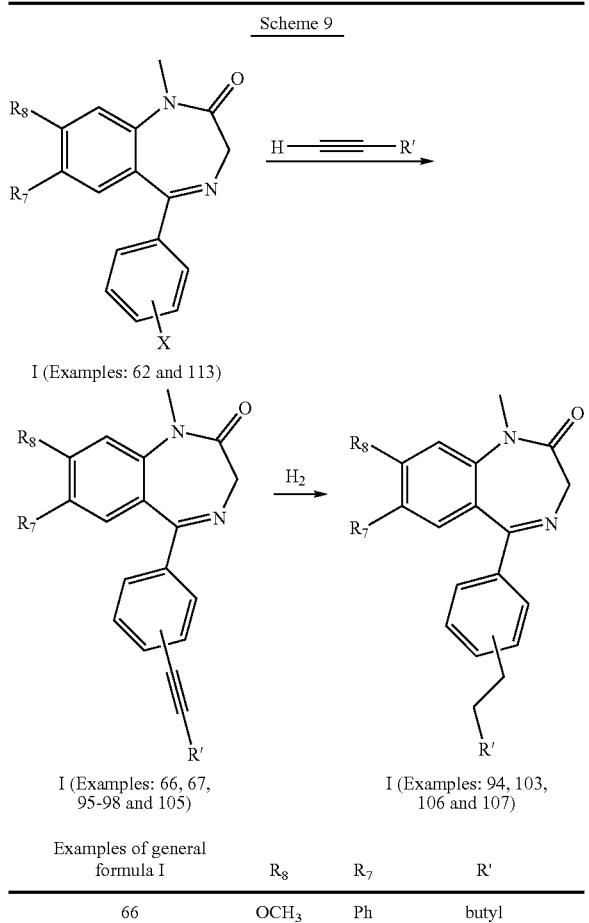

Scheme 9

I (Examples: 62 and 113)

I (Examples: 66, 67, 95-98 and 105)

I (Examples: 94, 103, 106 and 107)

Examples of general formula I

| | R$_8$ | R$_7$ | R' |
|---|---|---|---|
| 66 | OCH$_3$ | Ph | butyl |
| 67 | OCH$_3$ | Ph | CH$_2$NHBoc |

-continued

| | | | |
|---|---|---|---|
| 94 | OCH$_3$ | Ph | 3-(CH$_2$)$_2$Ph |
| 95 | OCH$_3$ | Ph | 3-CH$_2$OCH$_3$ |
| 96 | OCH$_3$ | Ph | 4-CH$_2$NHBoc |
| 97 | OCH$_3$ | Ph | 4-Ph |
| 98 | OCH$_3$ | Ph | 4-CH$_2$OCH$_3$ |
| 103 | OCH$_3$ | Ph | 3-CH$_2$OCH$_3$ |
| 105 | OCH$_3$ | Ph | 4-CH$_2$CH$_3$ |
| 106 | OCH$_3$ | Ph | 4-CH$_2$OCH$_3$ |
| 107 | OCH$_3$ | Ph | 4-CH$_2$NHBoc |

Compounds of general formula (I) can be converted in another series of compounds of general formula (I) by using a Sonogashira Palladium catalysed cross-coupling (scheme 9), in which R$_8$ and R$_7$ are as described above, with substituted alkynes in which R' is an alkyl, arylalkyl, hydroxyalkyl, alkoxyalkyl, aminoalkyl, amidoalkyl and carbamoylalkyl. X is an halogen atom, preferably bromine or iodine.

It should be understood that other methods of producing these compounds may be designed by the skilled person, based on common general knowledge and following guidance contained in this application.

As indicated above, a further object of this invention relates to a pharmaceutical composition comprising at least one compound of formula (I), as defined above, and a pharmaceutically acceptable vehicle or support.

The compounds may be formulated in various forms, including solid and liquid forms, such as tablets, gel, syrup, powder, aerosol, etc.

The compositions of this invention may contain physiologically acceptable diluents, fillers, lubricants, excipients, solvents, binders, stabilizers, and the like. Diluents that may be used in the compositions include but are not limited to dicalcium phosphate, calcium sulphate, lactose, cellulose, kaolin, mannitol, sodium chloride, dry starch, powdered sugar and for prolonged release tablet-hydroxy propyl methyl cellulose (HPMC). The binders that may be used in the compositions include but are not limited to starch, gelatin and fillers such as sucrose, glucose, dextrose and lactose.

Natural and synthetic gums that may be used in the compositions include but are not limited to sodium alginate, ghatti gum, carboxymethyl cellulose, methyl cellulose, polyvinyl pyrrolidone and veegum. Excipients that may be used in the compositions include but are not limited to microcrystalline cellulose, calcium sulfate, dicalcium phosphate, starch, magnesium stearate, lactose, and sucrose. Stabilizers that may be used include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that may be used include but are not limited to Ringers solution, water, distilled water, dimethyl sulfoxide to 50% in water, propylene glycol (neat or in water), phosphate buffered saline, balanced salt solution, glycol and other conventional fluids.

The dosages and dosage regimen in which the compounds of formula (I) are administered will vary according to the dosage form, mode of administration, the condition being treated and particulars of the patient being treated. Accordingly, optimal therapeutic concentrations will be best determined at the time and place through experimentation.

The compounds according to the invention can also be used enterally. Orally, the compounds according to the invention are suitable administered at the rate of 100 μg to 100 mg per day per kg of body weight. The required dose can be administered in one or more portions. For oral administration, suitable forms are, for example, tablets, gel, aerosols, pills, dragees, syrups, suspensions, emulsions, solutions, powders and granules; a preferred method of administration consists in using a suitable form containing from 1 mg to about 500 mg of active substance.

The compounds according to the invention can also be administered parenterally in the form of solutions or suspensions for intravenous or intramuscular perfusions or injections. In that case, the compounds according to the invention are generally administered at the rate of about 10 μg to 10 mg per day per kg of body weight; a preferred method of administration consists of using solutions or suspensions containing approximately from 0.01 mg to 1 mg of active substance per ml.

For the compounds of this invention, the dose to be administered, whether a single dose, multiple dose, or a daily dose, will of course vary with the particular compound employed because of the varying potency of the compound, the chosen route of administration, the size of the recipient, the type of disease and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. A doctor skilled in the art for treating the disease will be able to ascertain, without undue experimentation, appropriate protocols for the effective administration of the compounds of this present invention, such as by referring to the earlier published studies on compounds found to have effect on the disease to be treated.

According to another aspect, the present invention relates to a method for the treatment of a disease associated with abnormal regulation of intracellular cAMP and/or cGMP rate, comprising administering to a patient in need of such treatment an effective amount of at least one compound of general formula (I) as described above.

Preferred compounds for use according to the invention include any sub-group or compound as defined above.

Compounds according to the invention may act advantageously on PDE2. Compounds of the invention are preferably selective inhibitors of PDE2, i.e. they present an inhibiting effect on other phosphodiesterases, including for instance PDE3 and PDE4 to a lesser extent. Some compounds present also a specific inhibiting profile for PDE2, including with respect to adenosine deaminase, and present to this respect advantageous therapeutic properties.

Compounds of formula (I) are more particularly useful to treat diseases of the central nervous system, especially connected with an abnormal regulation of neurotransmitter effect or a release deficiency of one of the neurotransmitters (e.g. dopamine, noradrenaline, acetylcholine, . . . ). In particular, they can be used to treat a disease selected in the group consisting of depression, schizophrenia, autism, anxiety, bipolar disorder, attention deficit hyperactivity disorder (ADHD), sleeping disorders, obsessive compulsive disorders (OCD), Post Traumatic Stress Disorder (PTSD) fibromyalgia, Tourette's syndrome, drug or alcohol dependence, epilepsia, Alzheimer's disease, Parkinson's disease, amyotrophic lateral sclerosis, multiple sclerosis, obesity, and Lewy body dementia.

According to another aspect, compounds of formula (I) are more particularly useful to treat diseases of the peripheral nervous system or peripheral organs, including reduced natriuria pathologies, acute renal or liver failure, liverdysfunction, and pathologies due to or involving prolactin release dysfunction, such as restless leg syndrome, rheumatic, allergic or autoinflammatory disorders, such as rheumatoid arthritis, rhinitis, and asthma.

The present invention deals also with the use of compounds of the invention, or compositions comprising the same, as anxiolytics, anti-convulsants, sedative or to treat memory deficiency or cognitive disorders.

The present invention deals also with the use of compounds of the invention, or compositions comprising the same, to treat neuro-degenerative diseases.

The present invention concerns furthermore the use of such compounds for the treatment to treat obesity.

According to the invention, the term treatment denotes curative, symptomatic, and preventive treatment. Such compounds, compositions comprising the same, or treatment can be implemented alone or in combination with other active ingredients, compositions or treatments. Moreover, it can correspond to treatment of chronic or acute disorders.

FIGURES

FIG. 1: Swim test results expressed as mean duration of phases of immobility (s) (mean±sem) with different concentrations of a compound according to the invention.

Figure 2A:
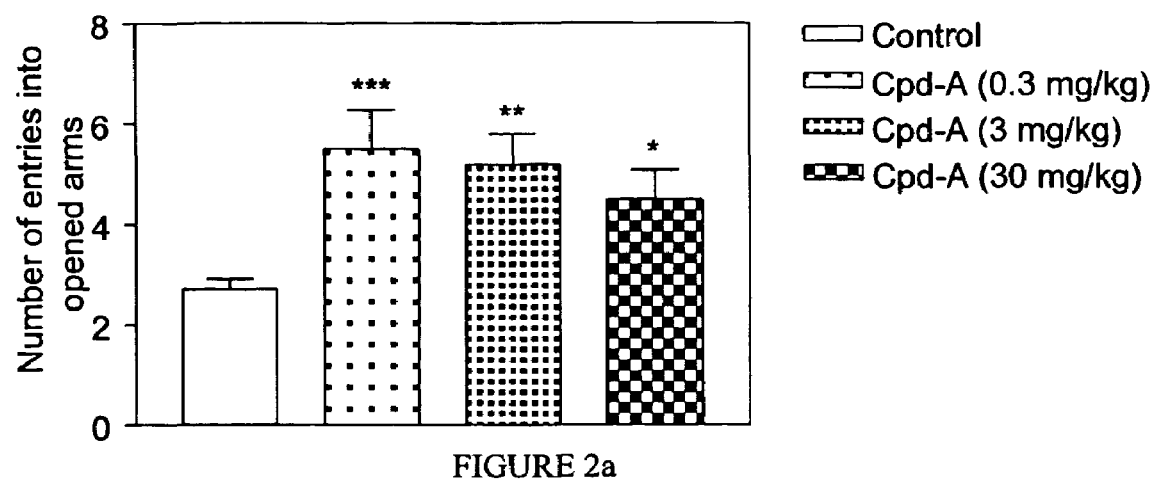
Figure 2B:
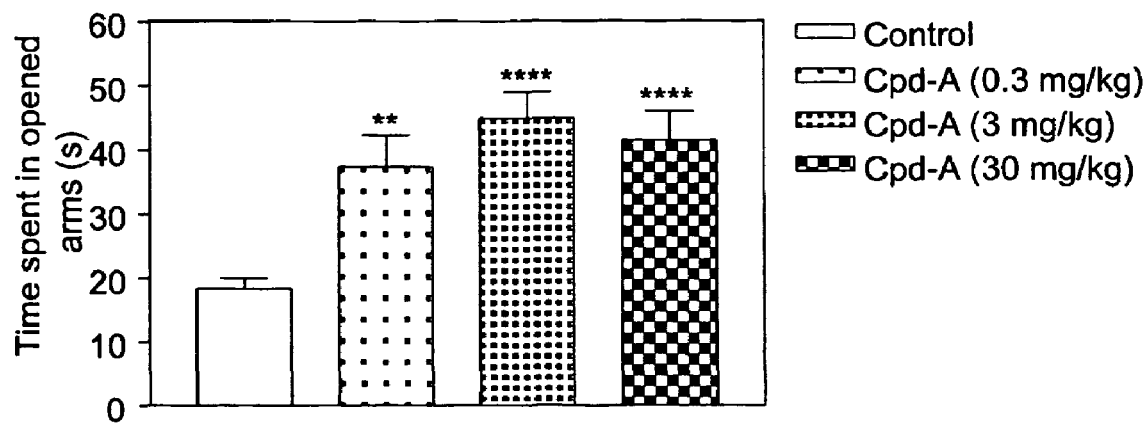

FIGS. 2a and 2b: Light dark test results expressed respectively as number of entries into open arms (mean±sem) and total time spent in open arms (s) (mean±sem) with different doses of a compound according to the invention.

Figure 3A:
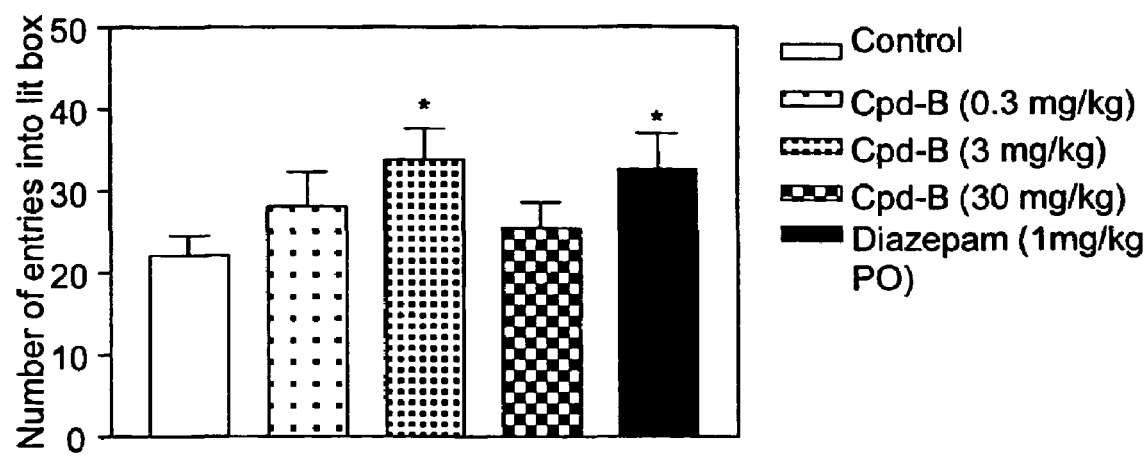
Figure 3B:
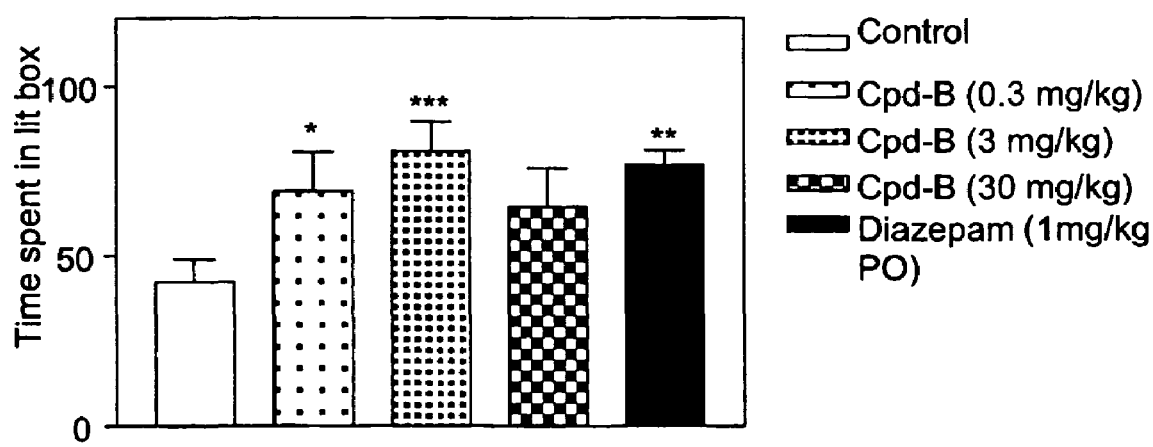

FIGS. 3a and 3b: Light dark test results expressed respectively as number of entries into open arms (mean±sem) and total time spent in open arms (s) (mean±sem) with different doses of another compound according to the invention.

Figure 4:
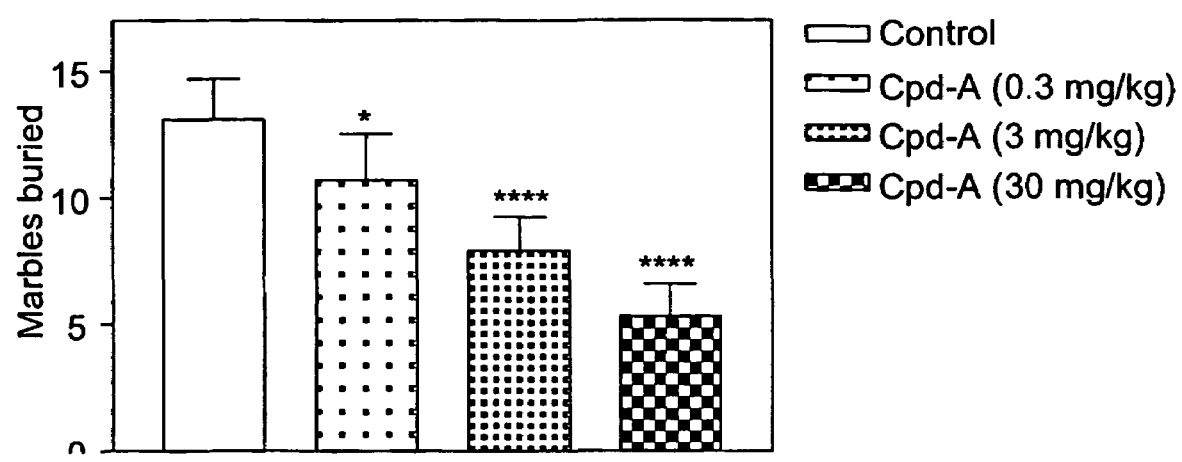

FIG. 4: Marble burying test expressed as number of buried marbles (mean±sem) with different doses of a compound according to the invention.

Figure 5:
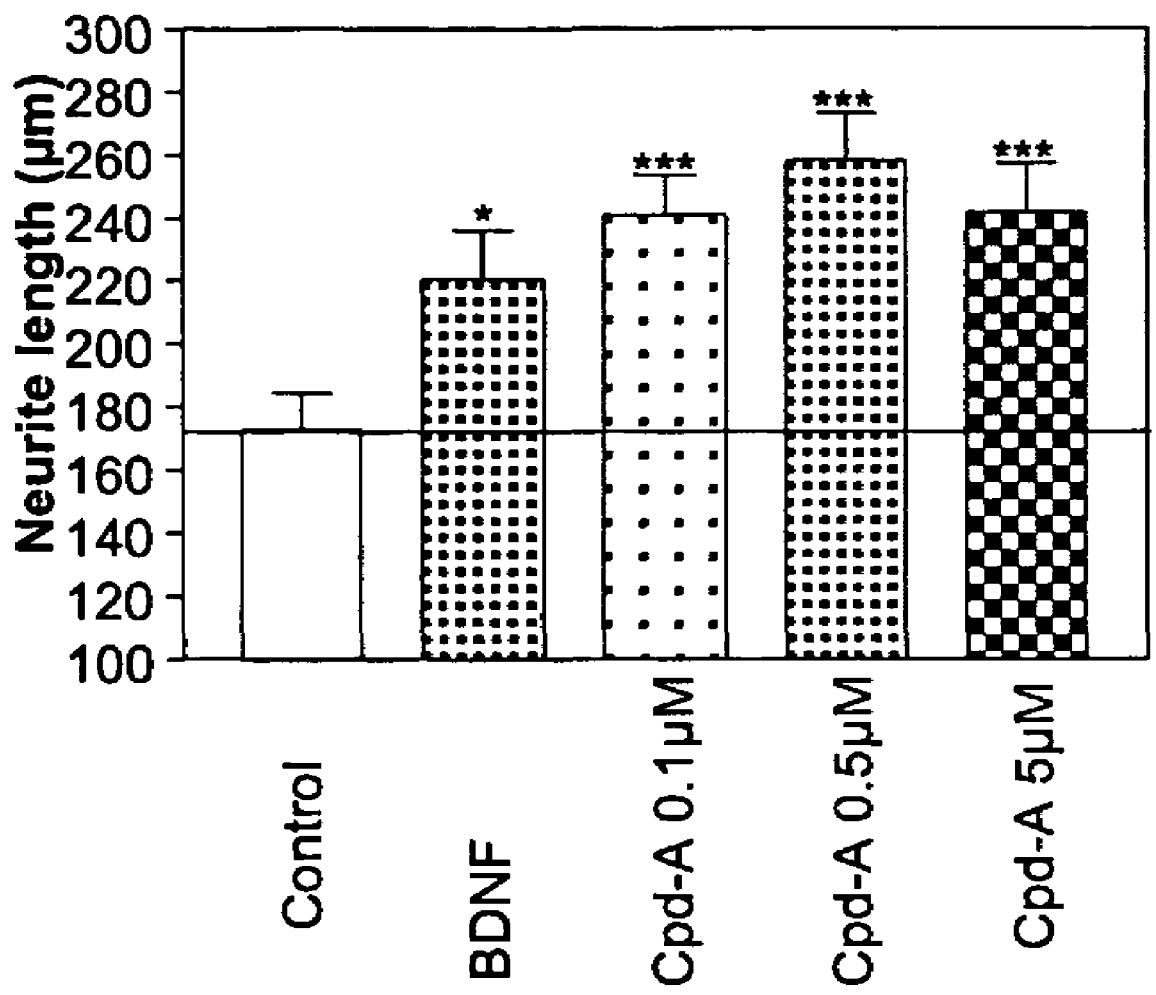

FIG. 5: Sprouting test expressed as neurite length (μm) (mean±sem) with different concentrations of a compound according to the invention.

The invention is illustrated by the following examples. However, they are representative only and should not be construed as being limiting in any respect.

In the Preparations and Examples, unless otherwise stated:

Proton Magnetic Resonance ($^1$H-NMR) spectra were recorded on Bruker Avance DRX 200 and 300 MHz. Chemical shifts are reported in ppm downfield (d) from Me$_4$Si, used as internal standard, and are assigned as singlets (s), doublets (d), doublets of doublets (dd), triplets (t), quartets (q) or multiplets (m).

The chromatographic analysis conditions were: column Waters XTerra MS C18 (4.6×30 mm, 5 μm); flow rate 1.0 mL/min; mobil phase: aqueous solution of 0.05% TFA (B) and acetonitrile.

The melting point has been performed using a capillary melting point apparatus ref: 7SMP3-0 Bibby.

EXAMPLES

Example A

Preparation of Intermediates of General Formula IV (Scheme 1)

Intermediate 1

3-(2-Amino-5-bromo-4-methoxy-benzoyl)-benzonitrile

A solution of 4-bromo-3-methoxy-phenylamine (3 g, 14.85 mmol), in dichloroethane (15 mL) was added dropwise to an ice-cold stirred solution of BCl$_3$ (1.0 M in CH$_2$Cl$_2$, 16.3 mL, 16.3 mmoles) under argon atmosphere.

Then were added isophtalonitrile (3.8 g, 29.70 mmoles) and anhydrous AlCl$_3$ (2.17 g, 16.30 mmoles) and the mixture was stirred at room temperature for 30 min. The mixture was then slowly heated to 60° C. and CH$_2$Cl$_2$ removed by distillation. Then the solution was refluxed at 78° C. for 16 hours. The reaction was allowed to cool to room temperature, treated with aqueous 2N HCl (28 mL) and heated at 78° C. for 3 hours. Extraction of the mixture with CH$_2$Cl$_2$ (2*50 mL) and removal of the solvent afforded the intermediate 1 as a crude mixture. The crude material was chromatographed through silica gel (eluant: CH$_2$Cl$_2$ 100% then AcOEt/Hexane: 1/1). The title compound (3 g) was obtained as a white solid in 61% yield.

TLC: (AcOEt/hexane: 1/1): Rf: 0.7 $^1$H NMR (CDCl$_3$, 300 MHz): δ 7.87-7.77 (m, 3H), 7.63-7.58 (m, 1H), 7.46 (s, 1H), 6.48 (s-broad, 2H), 6.20 (s, 1H), 3.93 (s, 3H).

Intermediate 2

3-(2-Amino-5-bromo-benzoyl)-benzonitrile

Prepared from 4-bromo-phenylamine, using the same method described for Intermediate 1. The title compound (2.7 g) was obtained as a yellow solid in 40% yield.

TLC: (AcOEt/CH$_2$Cl$_2$/hexane: 1/2/4): Rf: 0.5. $^1$H NMR (CDCl$_3$, 200 MHz): δ 7.96-7.81 (m, 3H), 7.70-7.62 (m, 1H), 7.41-7.38 (m, 1H), 7.46 (m, 1H), 6.70-6.66 (m, 1H), 6.22 (s-broad, 2H).

Intermediate 3

3-(2-Amino-5-iodo-benzoyl)-benzonitrile

Prepared from 4-iodo-phenylamine, using the same method described for Intermediate 1. The title compound (3.4 g) was obtained as a yellow solid in 37% yield.

TLC: (AcOEt/CH$_2$Cl$_2$: 1/4): Rf: 0.6. $^1$H NMR (CDCl$_3$, 300 MHz): δ 7.96-7.81 (m, 3H), 7.64-7.52 (m, 1H), 6.59-6.56 (m, 1H), 6.22 (s-broad, 2H).

Intermediate 4

(2-Amino-5-bromo-4-ethoxy-phenyl)-phenyl-methanone

A solution of 4-bromo-3-ethoxy-phenylamine (1.4 g, 6.48 mmol), in dichloroethane (8 mL) was added dropwise to an ice-cold stirred solution of BCl$_3$ (1.0 M in CH$_2$Cl$_2$, 6.87 mL, 9.72 mmoles) under argon atmosphere.

Then benzonitrile (1 mL, 9.72 mmoles) and anhydrous AlCl$_3$ (0.950 g, 7.12 mmoles) were added and the mixture was stirred at room temperature for 30 min. The mixture was then slowly heated to 60° C. and CH$_2$Cl$_2$ removed by distillation. Then the solution was refluxed at 78° C. for 16 hours. The reaction was allowed to cool to room temperature, treated with aqueous 2N HCl (14 mL) and heated at 78° C. for 3 hours. Extraction of the mixture with CH$_2$Cl$_2$ (2*25 mL) and removal of the solvent afforded the Intermediate 4 as a crude mixture. The crude material was chromatographied: eluant: AcOEt/Hexane: 2/1 then 1/1. The title compound (1.1 g) was obtained as a pale yellow solid in 53% yield.

TLC: (AcOEt/hexane: 1/1): Rf: 0.7 $^1$H RMN (CDCl$_3$, 200 MHz): δ 7.9-7.4 (m, 6H), 6.41 (s-broad, 2H), 6.20 (s, 1H), 4.20-4.10 (m, 2H), 1.06-1.49 (m, 3H).

Intermediate 13

3-(2-Amino-5-bromo-4-phenoxy-benzoyl)-benzonitrile

Prepared from 4-bromo-3-phenoxy-phenylamine, using the same method described for Intermediate 1. The title compound (3.1 g) was obtained as a yellow solid, (yield=39%).

Rf(Hex/CH$_2$Cl$_2$: 1/3): 0.4 $^1$H NMR (CDCl$_3$, 200 MHz): δ 7.80-7.77 (m, 3H arom), 7.62-7.37 (m, 4H arom), 7.27-7.23 (m, 1H arom), 7.10-7.06 (m, 2H arom), 6.22 (large s, 2H, NH$_2$), 5.99 (s, 1H arom).

Intermediate 16

3-(2-Amino-5-phenyl-benzoyl)-(3-bromo)phenyl-methanone

A solution of 2-phenyl-5-aminoanisole (1.77 g, 8.89 mmol), in dichloroethane (35 mL) was added dropwise to an ice-cold stirred solution of BCl$_3$ (1.0 M in CH$_2$Cl$_2$, 9.42 mL, 9.42 mmoles) under argon atmosphere.

Then 3-bromobenzonitrile (2.427 g, 13.334 mmoles) and anhydrous AlCl$_3$ (1.3 g, 9.777 mmoles) were added and the mixture was stirred at room temperature for 30 min. The mixture was then slowly heated to 60° C. and CH$_2$Cl$_2$ removed by distillation. Then the solution was refluxed at 78° C. for 16 hours. The reaction was allowed to cool to room temperature, treated with aqueous 2N HCl (30 mL) and heated at 78° C. for 3 hours. Extraction of the mixture with CH$_2$Cl$_2$ (2×35 mL) and removal of the solvent afforded the Intermediate 16 as a crude mixture. The crude material was purified by flash chromatography (eluant: AcOEt/Hexane: 2/1). The title compound (1.81 g) was obtained as a pale yellow solid in 53% yield.

TLC: (AcOEt/hexane: 1/2): Rf: 0.4 $^1$H RMN (CDCl$_3$, 200 MHz): δ 7.81-7.74 (m, 1H), 7.62-7.48 (2H), 7.37-7.27 (m, 7H), 3.85 (s, 1H)

Intermediate 19

3-(2-Amino-5-phenyl-benzoyl)-(4-methoxy)phenyl-methanone

A solution of 2-phenyl-5-aminoanisole (1.0 g, 5.02 mmoles), in 1,2-dichloroethane (8 mL) was added dropwise to an ice-cold stirred solution of BCl$_3$ (1.0 M in CH$_2$Cl$_2$, 5.31 mL, 5.31 mmoles) under argon atmosphere.

Then p-methoxybenzonitrile (1.0 g, 7.53 mmoles) and anhydrous AlCl$_3$ (0.74 g, 5.52 mmoles) were added and the mixture was stirred at room temperature for 30 min. The mixture was then slowly heated at 60° C. and CH$_2$Cl$_2$ removed by distillation. Then the solution was refluxed at 78° C. for 16 hours. The reaction was allowed to cool to room temperature, treated with aqueous 2N HCl (20 mL) and heated at 78° C. for 3 hours. Extraction of the mixture with CH$_2$Cl$_2$ (2×20 mL) and removal of the solvent afforded the Intermediate 19 as a crude mixture. The crude material was purified by flash chromatography (eluant: AcOEt/Hexane: 2/1). The title compound (1.14 g) was obtained as a pale yellow solid in 68% yield.

$^1$H RMN (CDCl$_3$, 300 MHz): δ 7.76-7.65 (m, 2H), 7.49 (s, 1H), 7.43-7.25 (m, 5H), 6.97-6.93 (m, 2H), 6.40-6.20 (m, 2H), 3.87 (s, 6H).

Intermediate 20

3-(4-Amino-6-trifluoromethoxy-biphenyl-3-carbonyl)-benzonitrile

Prepared from 2-trifluoromethoxy-biphenyl-4-ylamine, using the same method described for Intermediate 1. The title compound (500 mg) was obtained as a yellow solid, (yield=36%).

Rf(Hex/$CH_2Cl_2$: 1/4): 0.4 $^1$H NMR ($CDCl_3$, 200 MHz): δ 7.94-7.79 (m, 5H arom), 7.70-7.59 (m, 2H arom), 7.40-7.29 (m, 3H arom), 6.73 (s, 1H arom), 6.38 (large s, 2H, $NH_2$).

Intermediate 21

(2-Amino-5-bromo-4-methoxy-phenyl)-(4-methoxy-phenyl)-methanone

Prepared from 4-bromo-3-methoxy-phenylamine using the same method described for Intermediate 1. The title compound (4.51 g) was obtained as a yellow solid in 67% yield.

TLC: (AcOEt/hexane: 1/2): Rf: 0.41 $^1$H NMR ($CDCl_3$, 400 MHz): 7.65-7.60 (m, 3H), 6.98-6.96 (m, 2H), 6.20 (s board, 3H), 3.91 (s, 3H), 3.89 (s, 3H).

Preparation of Intermediates of General Formula V (Scheme 2)

Intermediate 5

3-(7-Bromo-8-methoxy-2-oxo-2,3-dihydro-1H-benzo[e][1,4]diazepin-5-yl)-benzonitrile A mixture of glycine ethyl ester hydrochloride (2.26 g, 16.20 mmol) and Intermediate 1 (2.68 g, 8.10 mmol) in dry pyridine (30 mL) was refluxed with stirring for 16 hours. One equivalent of glycine ethyl ester hydrochloride was added after 4 h, 8 h and 24 h. Removal of the pyridine under vacuum distillation afforded a crude which was partitioned between ethyl acetate (100 mL)/$H_2O$ (100 mL). The aqueous phase was extracted one time with 100 mL of ethyl acetate; the combined organic phases were dried over $Na_2SO_4$, filtered and evaporated until dryness. The crude material was chromatographied: eluant: AcOEt/Hexane: 1/1. The title compound (2 g) was obtained as a white solid (yield=54%).

TLC: (AcOEt/Hexane: 1/1): Rf: 0.1 $^1$H NMR ($CDCl_3$, 200 MHz): δ 9.41 (s-broad, 1H), 7.91 (m, 1H), 7.79-7.75 (m, 2H), 7.58-7.50 (m, 1H), 7.41 (s, 1H), 6.67 (s, 1H), 4.36 (s-broad, 2H), 4.00 (s, 3H).

Intermediate 6

7-bromo-8-ethoxy-5-phenyl-1,3-dihydro-benzo[e][1,4]diazepin-2-one

Prepared from (2-amino-5-bromo-4-ethoxy-phenyl)-phenylmethanone Intermediate 4 using the same conditions used to prepareIntermediate 5. The title compound was obtained as a beige solid (yield=24%).

TLC: (AcOEt/Hexane: 1/1): Rf: 0.28 1H NMR ($CDCl_3$, 300 MHz): δ 10.00 (s-broad, 1H), 7.58-7.51 (m, 2H), 7.49-7.44 (m, 2H), 7.43-7.36 (m, 2H), 6.65 (s, 1H), 4.6-4.3 (m, 2H), 4.2-3.9 (m, 2H), 1.57-1.46 (m, 3H).

Intermediate 7

3-(7-Iodo-2-oxo-2,3-dihydro-1H-benzo[e][1,4]diazepin-5-yl)-benzonitrile

Prepared from 3-(2-amino-5-iodo-benzoyl)-benzonitrile Intermediate 3 using the same conditions used to prepareIntermediate 5. The title compound (1.85 g) was obtained as a beige solid, (yield=55%).

TLC: (AcOEt/$CH_2Cl_2$: 9/1): Rf: 0.6 $^1$H NMR (DMSO-$d_6$, 200 MHz): δ 10.69 (s-broad, 1H), 8.01-7.88 (m, 3H), 7.78-7.67 (m, 2H), 7.53 (s, 1H), 7.11-7.06 (m, 1H), 4.20 (s-broad, 2H).

Intermediate 14

3-(7-Bromo-2-oxo-8-phenoxy-2,3-dihydro-1H-benzo[e][1,4]diazepin-5-yl)-benzonitrile Prepared from 3-(2-amino-5-bromo-4-phenoxy-benzoyl)-benzonitrile Intermediate 13 using the same conditions used to prepare Intermediate 5. The title compound (1.7 g) was obtained as a beige solid, (yield=60%).

Rf(AcOEt/$CH_2Cl_2$: 1/2): 0.4 $^1$H NMR ($CDCl_3$, 300 MHz): δ 8.53 (s, 1H, NH), 7.90 (s, 1H arom), 7.81-7.76 (m, 2H arom), 7.58-7.44 (m, 4H arom), 7.31-7.27 (m, 1H arom), 7.14-7.11 (m, 2H arom), 6.50 (s, 1H arom), 4.29 (s large, 2H, $CH_2$).

Intermediate 22:

7-Bromo-8-methoxy-5-(4-methoxy-phenyl)-1,3-dihydro-benzo[e][1,4]diazepin-2-one Prepared from (2-amino-5-bromo-4-methoxy-phenyl)-(4-methoxy-phenyl)-methanone Intermediate 21 using the same conditions used to prepare Intermediate 5 The crude material was chromatographied: eluant: AcOEt/Hexane: 1/1. The title compound (2.79 g) was obtained as a beige solid (yield=56%).

TLC: (AcOEt/Hexane: 1/1): Rf: 0.10 $^1$H NMR ($CDCl_3$, 400 MHz): 9.39 (s, 1H), 7.51-7.47 (m, 3H), 6.92-6.90 (m, 2H), 6.62 (s, 1H), 4.28 (s board, 2H), 3.96 (s, 3H), 3.85 (s, 3H).

Example 76

5-(4-Methoxy-phenyl)-8-methoxy-7-phenyl-1,3-dihydro-benzo[e][1,4]diazepin-2-one Prepared from 3-(2-amino-5-phenyl-benzoyl)-(4-methoxy)phenyl-methanone Intermediate 19 using the same conditions used to prepareIntermediate 5. The title compound (0.36 g) was obtained as a beige solid, (yield=28%).

1H NMR (CDCl3, 300 MHz): δ 7.56-7.53 (m, =2H), 7.45-7.28 (s, 6H), 6.90-6.87 (s, 2H), 6.68 (s, 1H), 4.35 (broad s, 2H), 3.90 (s, 3H), 3.84 (s, 3H).

Example 85

3-(2-Oxo-7-phenyl-8-trifluoromethoxy-2,3-dihydro-1H-benzo[e][1,4]diazepin-5-yl)-benzonitrile Prepared from 3-(4-amino-6-trifluoromethoxy-biphenyl-3-carbonyl)-benzonitrile 20 using the same conditions used to prepare Intermediate 5. The title compound (110 mg) was obtained as a beige solid, (yield=40%).

1H NMR (CDCl3, 300 MHz): δ 8.20 (s, 1H), 7.85-7.50 (m, 3H), 7.41-7.31 (s, 6H), 7.24-7.14 (m, 2H), 4.45 (broad s, 2H).

Example 114

5-(4-Bromo-phenyl)-8-methoxy-7-phenyl-1,3-dihydro-benzo[e][1,4]diazepin-2-one

Prepared from (4-Amino-6-methoxy-biphenyl-3-yl)-(4-bromo-phenyl)-methanone The title compound (785 mg) was obtained as a yellowish solid, (yield=28%).
TLC: (H/AcOEt: 1/1): Rf: 0.3 1H NMR (CDCl3, 300 MHz): δ 9.29 (s board, 1H), 7.54-7.22 (m, 11), 6.70 (s, 1H), 4.38 (s board, 2H), 3.91 (s, 3H).

Preparation of Intermediates of General Formula V (Scheme 3)

Intermediate 8

3-(7-Bromo-2-oxo-2,3-dihydro-1H-benzo[e][1,4]diazepin-5-yl)-benzonitrile

To a solution of 3-(2-Amino-5-bromo-benzoyl)-benzonitrile Intermediate 2 (10 mmoles) in methylene chloride (20 mL) at 0-5° C., were added bromoacetyl bromide (1.05 mL, 12 mmoles) and dropwise a solution of $Na_2CO_3$ 10% aq. (11.70 mL). The solution was stirred at this temperature for 30 min. The two layers were separated; the organic layer was washed with water (20 mL), dried over $Na_2SO_4$, filtered and evaporated under reduced pressure to a crude which was stirred in $NH_3$ (7N)/MeOH (30 mL) at 0° C. for 2-4 hours and then refluxed for 16 hours. The working solution was evaporated in vacuum, then triturated in water (100 mL) and filtered. The title compound (320 mg) was obtained as a brown solid in 62% yield.
TLC: (AcOEt/$CH_2Cl_2$: 1/2): Rf: 0.4 $^1$H NMR (CDCl$_3$, 200 MHz): δ 9.35 (s-broad, 1H), 7.91 (s, 1H), 7.89-7.75 (m, 3H), 7.51-7.50 (m, 1H), 7.37 (s, 1H), 7.14-7.09 (m, 1H), 4.36 (s-broad, 2H).

Example 80

5-(3-Bromo-phenyl)-8-methoxy-7-phenyl-1,3-dihydro-benzo[e][1,4]diazepin-2-one

Prepared from 3-(2-Amino-5-phenyl-benzoyl)-(3-bromo)phenyl-methanone Intermediate 19 using the same conditions used to prepareIntermediate 16. The title compound (1.98 g) was obtained as a pale yellow solid, (yield=90%).
Rf (Hexane/EtAOc: 1/1)=0.2 RMN (CDCl3), (200 Hz): d 9.49 (s broad, 1H), 7.86 (s, 1H), 7.66-7.21 (m, 9H), 6.89 (s, 1H), 4.35 (s, 2H), 3.93 (s, 3H).

Example 102

5-(2-Bromo-phenyl)-8-methoxy-7-phenyl-1,3-dihydro-benzo[e][1,4]diazepin-2-one

Prepared from 5-(2-Bromo-phenyl)-8-methoxy-7-phenyl-1,3-dihydro-benzo[e][1,4]diazepin-2-one
The title compound (351 mg) was obtained as a beige solid, (yield=61%).
TLC: (H/AcOEt: 1/1): Rf: 0.1 1H NMR (CDCl3, 300 MHz): δ 7.59-7.51 (m, 2H), 7.38-7.28 (m, 7H), 6.96 (s, 1H), 6.84 (s, 1H), 4.85-4.80 and 3.91-3.87 (AB system, J=10.5 Hz, 2H), 3.85 (s, 3H), 3.52 (s, 3H).

Preparation of Intermediates of General Formula VII (Scheme 4)

Intermediate 9

3-(7-bromo-8-methoxy-1-methyl-2-oxo-2,3-dihydro-1H-benzo[e][1,4]diazepin-5-yl)-benzonitrile To a mixture of toluene (20 mL) and Aliquat 336 (20 μL) was introduced methyl iodide (337 μL, 5.41 mmoles) while the mixture was agitated, powdered 3-(7-bromo-8-methoxy-2-oxo-2,3-dihydro-1H-benzo[e][1,4]diazepin-5-yl)-benzonitrile Intermediate 5 (1 g, 2.7 mmoles) and 50% aqueous sodium hydroxide (3.1 mL) were added to the reaction mixture. The two-phase system was stirred vigorously for 4 hours. The phases were separated, and the aqueous layer was extracted with ethyl acetate (20 mL). The combined organic extracts were washed with cold water (10 mL); then the organic phase were dried over $Na_2SO_4$ and concentrated to dryness. The title compound (0.93 g) was crystallised from MeOH/Diisopropylether to afford a white powder in 90% yield.
TLC: (AcOEt/Hexane: 1/1): Rf: 0.2 $^1$H NMR (CDCl$_3$, 200 MHz): δ 7.91-7.86 (m, 2H), 7.79-7.75 (m, 1H), 7.59-7.51 (m, 1H), 7.40 (s, 1H), 6.81 (s, 1H), 4.89-4.84 and 3.83-3.78 (AB system, J=11 Hz), 4.02 (s, 3H), 3.44 (s, 3H).

Intermediate 10

3-(7-Bromo-1-methyl-2-oxo-2,3-dihydro-1H-benzo[e][1,4]diazepin-5-yl)-benzonitrile Prepared from 3-(7-bromo-2-oxo-2,3-dihydro-1H-benzo[e][1,4]diazepin-5-yl)-benzonitrile Intermediate 8 using the same method described for Intermediate 9. The title compound (220 mg) was obtained as a yellow solid (yield=88%).
TLC: (AcOEt/$CH_2Cl_2$: 4/1): Rf: 0.7 $^1$H NMR (CDCl$_3$, 300 MHz): δ 7.92-7.87 (m, 2H), 7.79-7.75 (m, 2H), 7.59-7.51 (m, 1H), 7.37-7.36 (m, 1H), 7.29-7.27 (m, 1H), 4.90-4.87 and 3.81-3.77 (AB system, J=11 Hz), 3.41 (s, 3H).

Intermediate 11

3-(7-Iodo-8-methoxy-1-methyl-2-oxo-2,3-dihydro-1H-benzo[e][1,4]diazepin-5-yl)-benzonitrile Prepared from 3-(7-iodo-2-oxo-2,3-dihydro-1H-benzo[e][1,4]diazepin-5-yl)-benzonitrile Intermediate 7 using the same method described for Intermediate 9. The title compound (1.55 g) was obtained as a yellow solid (yield=83%).
TLC: (AcOEt/$CH_2Cl_2$: 2/1): Rf: 0.5 $^1$H NMR (CDCl$_3$, 200 MHz): δ 7.91-7.75 (m, 4H), 7.59-7.53 (m, 2H), 7.16-7.12 (m, 1H), 4.90-4.84 and 3.81-3.78 (AB system, J=11 Hz), 3.39 (s, 3H).

Intermediate 12

7-bromo-8-ethoxy-1-ethyl-5-phenyl-1,3-dihydro-benzo[e][1,4]diazepin-2-one

Prepared from 3-(7-bromo-8-ethoxy-2-oxo-2,3-dihydro-1H-benzo[e][1,4]diazepin-5-yl)-benzene Intermediate 6 using the same method described for Intermediate 9. The title compound was obtained as a beige solid (yield=80%).

TLC: (AcOEt/Hexane: 1/1): Rf: 0.47 $^1$H NMR (CDCl$_3$, 200 MHz): δ 7.60-7.53 (m, 2H), 7.47-7.35 (m, 4H), 6.82 (s, 1H), 4.78-4.74 and 4.38-4.14 (AB system, J=11 Hz, 4H), 3.82-3.62 (m, 2H), 1.60-1.50 (m, 3H), 1.13-1.09 (m, 3H).

Intermediate 15

3-(7-Bromo-1-methyl-2-oxo-8-phenoxy-2,3-dihydro-1H-benzo[e][1,4]diazepin-5-yl)-benzonitrile Prepared from 3-(7-bromo-2-oxo-8-phenoxy-2,3-dihydro-1H-benzo[e][1,4]diazepin-5-yl)-benzonitrile Intermediate 14 using the same method described for Intermediate 9. The title compound (1.5 g) was obtained as a yellow solid (yield=97%).

Rf (AcOEt/CH$_2$Cl$_2$: 1/2): 0.5 $^1$H NMR (CDCl$_3$, 200 MHz): δ 7.93 (s, 1H), 7.98-7.76 (m, 2H), 7.61-7.44 (m, 4H), 7.32-7.27 (m, 1H), 7.15-7.11 (m, 2H), 6.72 (s, 1H), 4.29 (s large, 2H), 4.88-4.83 and 3.84-3.78 (AB system, J=11 Hz, 2H), 3.20 (s, 3H).

Intermediate 23

7-Bromo-8-methoxy-5-(4-methoxy-phenyl)-1-methyl-1,3-dihydro-benzo[e][1,4]diazepin-2-one Prepared from 7-bromo-8-methoxy-5-(4-methoxy-phenyl)-1,3-dihydro-benzo[e][1,4]diazepin-2-one Intermediate 22 using the same method described for Intermediate 9. The title compound (2.3 g) was crystallised from Hexane/Diisopropylether to afford a beige powder in 77% yield.

TLC: (AcOEt/hexane: 1/1): Rf: 0.17 $^1$H NMR (CDCl$_3$, 400 MHz): δ 7.57-7.50 (m, 3H), 6.93-6.91 (m, 2H), 6.76 (s, 1H), 4.78-4.75 and 3.77-3.74 (AB system, J=10.5 Hz, 2H), 4.00 (s, 3H), 3.86 (s, 3H), 3.41 (s, 3H).

Example 62

5-(3-Bromo-phenyl)-8-methoxy-1-methyl-7-phenyl-1,3-dihydro-benzo[e][1,4]diazepin-2-one Prepared from 5-(3-Bromo-phenyl)-8-methoxy-7-phenyl-1,3-dihydro-benzo[e][1,4]diazepin-2-one Intermediate 80 using the same method described for Intermediate 9. The title compound (1.38 g) was obtained as a pale yellow solid (yield 68%).

1H NMR (CDCl3, 300 MHz): δ 7.87 (s, 1H), 7.57-7.53 (m, 2H), 7.46-7.21 (m, 7H), 6.86 (s, 1H), 4.87-4.83 and 3.90-3.86 (AB system, J=10.5 Hz, 2H), 3.94 (s, 3H), 3.49 (s, 3H).

Example 86

3-(1-Methyl-2-oxo-7-phenyl-8-trifluoromethoxy-2,3-dihydro-1H-benzo[e][1,4]diazepin-5-yl)-benzonitrile Prepared from 3-(2-oxo-7-phenyl-8-trifluoromethoxy-2,3-dihydro-1H-benzo[e][1,4]diazepin-5-yl)-benzonitrile Example 85 using the same method described for Intermediate 9. The title compound (80 mg) was obtained as a beige solid, (yield 86%).

1H NMR (CDCl3, 200 MHz): δ 7.96-7.89 (m, 2H), 7.77-7.73 (m, 1H), 7.58-7.22 (m, 8H), 4.97-4.91 and 3.94-3.88 (AB system, J=11 Hz, 2H), 3.47 (s, 3H).

Example 104

5-(2-Bromo-phenyl)-8-methoxy-1-methyl-7-phenyl-1,3-dihydro-benzo[e][1,4]diazepin-2-one Prepared from 5-(2-Bromo-phenyl)-8-methoxy-7-phenyl-1,3-dihydro-benzo[e][1,4]diazepin-2-one The title compound (351 mg) was obtained as a beige solid, (yield=61%).

TLC: (H/AcOEt: 1/1): Rf: 0.2 1H NMR (CDCl3, 300 MHz): δ 7.55-7.52 (m, 2H), 7.38-7.28 (m, 7H), 6.96 (s, 1H), 6.84 (s, 1H), 4.88-4.85 and 3.91-3.87 (AB system, J=10.5 Hz,2H), 3.91 (s, 3H), 3.52 (s, 3H).

Example 113

5-(4-Bromo-phenyl)-8-methoxy-1-methyl-7-phenyl-1,3-dihydro-benzo[e][1,4]diazepin-2-one Prepared from 5-(4-Bromo-phenyl)-8-methoxy-7-phenyl-1,3-dihydro-benzo[e][1,4]diazepin-2-one The title compound (621 mg) was obtained as a yellowish solid, (yield=78%).

TLC: (H/AcOEt: 1/1): Rf: 0.3 1H NMR (CDCl3, 300 MHz): δ 7.54-7.50 (m, 4H), 7.45-7.30 (m, 5H), 7.20 (s, 1H), 6.86 (s, 1H), 4.85-4.81 and 3.88-3.84 (AB system, J=10.5 Hz,2H), 3.93 (s, 3H), 3.48 (s, 3H).

Preparation of Examples of General Formula I
(Schemes 5 and 8)

Example 1

3-(8-Methoxy-1-methyl-2-oxo-7-phenyl-2,3-dihydro-1H-benzo[e][1,4]diazepin-5-yl)-benzonitrile To 5 mL of degazed DMF were added 3-(7-bromo-8-methoxy-1-methyl-2-oxo-2,3-dihydro-1H-benzo[e][1,4]diazepin-5-yl)-benzonitrile Intermediate 9 (200 mg, 0.52 mmol), benzene boronic acid (160 mg, 1.32 mmoles), tripotassium phosphate (300 mg, 1.42 mmol), Pd(PPh$_3$)$_4$ (30 mg, 0.03 mmoles). The mixture was stirred for 16 hours at 120° C. under nitrogen atmosphere. The working solution was diluted ten times with water and extracted three times with ethyl acetate. The organic phase was dried over Na$_2$SO$_4$ and concentrated until dryness. The residue was chromatographied: eluant: CH$_2$Cl$_2$/Et$_2$O: 1/1. The obtained compound was crystallised from ether/pentane to afford the title compound (118 mg): white solid, (yield=60%).

TLC: (AcOEt): Rf: 0.6 $^1$H NMR (CDCl$_3$, 300 MHz): δ 7.96-7.92 (m, 2H), 7.74-7.71 (m, 1H), 7.54-7.52 (m, 1H), 7.44-7.35 (m, 5H), 7.15 (s, 1H), 6.88 (s, 1H), 4.90-4.86 and 3.91-3.88 (AB system, J=11 Hz), 3.99 (s, 3H), 3.50 (s, 3H).

Example 2

3-[7-(4-Fluoro-phenyl)-8-methoxy-1-methyl-2-oxo-2,3-dihydro-1H-benzo[e][1,4]diazepin-5-yl]-benzonitrile Prepared from 3-(7-bromo-8-methoxy-1-methyl-2-oxo-2,3-dihydro-1H-benzo[e][1,4]diazepin-5-yl)-benzonitrile Intermediate 9 using the same method described for Example 1 and instead of using benzene boronic acid, we used p-fluorophenyl boronic acid. The title compound (66 mg) was obtained as a white solid, (yield=43%).

TLC: (AcOEt): Rf: 0.6 ¹H NMR (CDCl₃, 200 MHz): δ 7.95-7.92 (m, 2H), 7.75-7.71 (m, 1H), 7.57-7.49 (m, 1H), 7.43-7.36 (m, 2H), 7.13-7.04 (m, 3H), 6.88 (s, 1H), 4.91-4.85 and 3.91-3.86 (AB system, J=11 Hz), 3.95 (s, 3H), 3.49 (s, 3H).

Example 3

3-[8-Methoxy-7-(2-methoxy-phenyl)-1-methyl-2-oxo-2,3-dihydro-1H-benzo[e][1,4]diazepin-5-yl]-benzonitrile Prepared from 3-(7-bromo-8-methoxy-1-methyl-2-oxo-2,3-dihydro-1H-benzo[e][1,4]diazepin-5-yl)-benzonitrile Intermediate 9 using the same method described for Example 1 and instead of using benzene boronic acid, we used o-methoxyphenyl boronic acid. The title compound (80 mg) was obtained as a white solid, in 50% yield.

TLC: (AcOEt): Rf: 0.6 ¹H NMR (CDCl₃, 200 MHz): δ 8.04-7.96 (m, 2H), 7.74-7.70 (m, 1H), 7.55-7.45 (m, 1H), 7.38-7.30 (m, 1H), 7.22-7.19 (m, 1H), 7.14 (s, 1H), 7.03-6.95 (m, 2H), 6.88 (s, 1H), 4.89-4.84 and 3.95-3.90 (AB system, J=10 Hz), 3.90 (s, 3H), 3.82 (s, 3H), 3.50 (s, 3H).

Example 4

3-[8-Methoxy-7-(4-methoxy-phenyl)-1-methyl-2-oxo-2,3-dihydro-1H-benzo[e][1,4]diazepin-5-yl]-benzonitrile Prepared from 3-(7-bromo-8-methoxy-1-methyl-2-oxo-2,3-dihydro-1H-benzo[e][1,4]diazepin-5-yl)-benzonitrile Intermediate 9 using the same method described for Example 1 and instead of using benzene boronic acid, we used p-methoxyphenyl boronic acid. The title compound (85 mg) was obtained as a white solid, (yield=53%).

TLC: (AcOEt): Rf: 0.6 ¹H NMR (CDCl₃, 200 MHz): δ 7.96-7.92 (m, 2H), 7.74-7.71 (m, 1H), 7.55-7.48 (m, 1H), 7.39-7.35 (m, 2H), 7.12 (s, 1H), 6.96-6.91 (m, 2H), 6.87 (s, 1H), 4.90-4.84 and 3.91-3.86 (AB system, J=11 Hz), 3.94 (s, 3H), 3.83 (s, 3H), 3.49 (s, 3H).

Example 5

3-[7-(2-Chloro-phenyl)-8-methoxy-1-methyl-2-oxo-2,3-dihydro-1H-benzo[e][1,4]diazepin-5-yl]-benzonitrile Prepared from 3-(7-bromo-8-methoxy-1-methyl-2-oxo-2,3-dihydro-1H-benzo[e][1,4]diazepin-5-yl)-benzonitrile Intermediate 9 using the same method described for Example 1 and instead of using benzene boronic acid, we used o-chlorophenyl boronic acid. The title compound (107 mg) was obtained as a white solid, (yield=66%).

TLC: (AcOEt): Rf: 0.6 ¹H NMR (CDCl₃, 200 MHz): δ 7.97 (m, 2H), 7.74-7.44 (m, 6H), 7.09 (s, 1H), 6.89 (s, 1H), 4.91-4.86 and 3.94-3.89 (AB system, J=11 Hz), 3.91 (s, 3H), 3.51 (s, 3H).

Example 6

3-[7-(3-Chloro-phenyl)-8-methoxy-1-methyl-2-oxo-2,3-dihydro-1H-benzo[e][1,4]diazepin-5-yl]-benzonitrile Prepared from 3-(7-bromo-8-methoxy-1-methyl-2-oxo-2,3-dihydro-1H-benzo[e][1,4]diazepin-5-yl)-benzonitrile Intermediate 9 using the same method described for Example 1 and instead of using benzene boronic acid, we used m-chlorophenyl boronic acid. The title compound (58 mg) was obtained as a white solid, (yield=36%).

TLC: (AcOEt): Rf: 0.6 ¹H NMR (CDCl₃, 300 MHz): δ 7.95-7.91 (m, 2H), 7.75-7.72 (m, 1H), 7.55-7.50 (m, 1H), 7.43 (m, 1H), 7.32 (m, 3H), 7.13 (s, 1H), 6.88 (s, 1H), 4.90-4.87 and 3.89-3.86 (AB system, J=11 Hz), 3.95 (s, 3H), 3.49 (s, 3H).

Example 7

3-[7-(4-Chloro-phenyl)-8-methoxy-1-methyl-2-oxo-2,3-dihydro-1H-benzo[e][1,4]diazepin-5-yl]-benzonitrile Prepared from 3-(7-bromo-8-methoxy-1-methyl-2-oxo-2,3-dihydro-1H-benzo[e][1,4]diazepin-5-yl)-benzonitrile Intermediate 9 using the same method described for Example 1 and instead of using benzene boronic acid, we used p-chlorophenyl boronic acid. The title compound (48 mg) was obtained as a white solid, (yield=30%).

TLC: (AcOEt): Rf: 0.6 ¹H NMR (CDCl₃, 300 MHz): δ 7.94-7.92 (m, 2H), 7.75-7.72 (m, 1H), 7.55-7.50 (m, 1H), 7.37 (m, 4H), 7.12 (s, 1H), 6.68 (s, 1H), 4.90-4.86 and 3.90-3.86 (AB system, J=11 Hz), 3.95 (s, 3H), 3.49 (s, 3H).

Example 8

3-(7-Furan-2-yl-8-methoxy-1-methyl-2-oxo-2,3-dihydro-1H-benzo[e][1,4]diazepin-5-yl)-benzonitrile Prepared from 3-(7-bromo-8-methoxy-1-methyl-2-oxo-2,3-dihydro-1H-benzo[e][1,4]diazepin-5-yl)-benzonitrile Intermediate 9 using the same method described for Example 1 and instead of using benzene boronic acid, we used furan-2-boronic acid. The title compound (40 mg) was obtained as a white solid, (yield=41%).

TLC: (AcOEt): Rf: 0.6 1H NMR (CDCl₃, 200 MHz): δ 7.89-7.96 (m, 2H), 7.72-7.76 (m, 1H), 7.49-7.59 (m, 1H), 7.15-7.19 (d, J=9 Hz, 1H), 6.84-6.86 (d, J=2 Hz, 1H), 6.75-6.80 (dd, J=2 Hz and 9 Hz, 1H), 3.79-3.84 and 4.80-4.86 (AB system, J=10 Hz), 3.93 (s, 3H), 3.42 (s, 3H).

Example 9

3-(1-Methyl-2-oxo-7-phenyl-2,3-dihydro-1H-benzo[e][1,4]diazepin-5-yl)-benzaldehyde To 5 mL of degazed DMF were added 5-chloro-1-methyl-7-phenyl-1,3-dihydro-benzo[e][1,4]diazepin-2-one (200 mg, 0.52 mmol), 3-formylbenzene boronic acid (160 mg, 1.32 mmoles), tripotassium phosphate (300 mg, 1.42 mmol), Pd(PPh₃)₄ (30 mg, 0.03 mmoles). The mixture was stirred for 16 hours at 120° C. under nitrogen atmosphere. The working solution was diluted ten times with water and extracted three times with ethyl acetate. The organic phase was dried over Na₂SO₄ and concentrated until dryness. The residue was chromatographied: eluant: CH₂Cl₂/Et₂O: 1/1. The title compound was crystallised from ether/pentane to afford the title compound (118 mg): white solid, (yield=25%).

TLC: (Hexane/AcOEt: 3/1): Rf: 0.10 1H NMR (CDCl3, 200 MHz): δ 10.05 (s, 1H), 8.17 (s, 1H), 8.02-7.35 (m, 11H), 4.92-4.87 and 3.9-3.87 (AB system, J=10 Hz, 2H), 3.48 (s, 3H).

Example 10

3-[8-Methoxy-7-(2-methoxy-phenyl)-2-oxo-2,3-dihydro-1H-benzo[e][1,4]diazepin-5-yl]-benzonitrile Prepared from 3-(7-bromo-8-methoxy-2-oxo-2,3-dihydro-1H-benzo[e][1,4]diazepin-5-yl)-benzonitrile Intermediate 5 using the same method described for Example 1 and instead of using benzene boronic acid, we used 2-methoxybenzene boronic acid. The title compound (474 mg) was obtained as a pale yellow solid, (yield=88%).

TLC: (AcOEt/Hexane: 1/1): Rf: 0.1)

Example 11

3-(1-Methyl-2-oxo-7-phenyl-2,3-dihydro-1H-benzo[e][1,4]diazepin-5-yl)-benzonitrile Prepared from 3-(7-bromo-1-methyl-2-oxo-2,3-dihydro-1H-benzo[e][1,4]diazepin-5-yl)-benzonitrile Intermediate 14 using the same method described for Example 1. The title compound (82 mg) was obtained as a yellow solid, (yield=69%).

TLC: (AcOEt/CH$_2$Cl$_2$: 4/1): Rf: 0.4 $^1$H NMR (CDCl$_3$, 200 MHz): δ 7.98-7.92 (m, 2H), 7.85-7.73 (m, 2H), 7.57-7.40 (m, 7H), 4.92-4.87 and 3.91-3.86 (AB system, J=11 Hz$_2$), 3.47 (s, 3H).

Example 12

3-[7-(2-Methoxy-phenyl)-1-methyl-2-oxo-2,3-dihydro-1H-benzo[e][1,4]diazepin-5-yl]-benzonitrile Prepared from 3-(7-bromo-1-methyl-2-oxo-2,3-dihydro-1H-benzo[e][1,4]diazepin-5-yl)-benzonitrile Intermediate 14 using the same method described for Example 1 and instead of using benzene boronic acid, we used 2-methoxyphenyl boronic acid. The title compound (85 mg) was obtained as a yellow solid, (yield=45%).

TLC: (AcOEt/CH$_2$Cl$_2$: 3/7): Rf: 0.3 $^1$H NMR (CDCl$_3$, 200 MHz): δ 7.97-7.73 (m, 4H), 7.53-7.36 (m, 4H), 7.01-6.90 (m, 3H), 4.92-4.87 and 3.91-3.85 (AB system, J=10 Hz$_2$), 3.85 (s, 3H), 3.47 (s, 3H).

Example 13

3-[7-(3-Methoxy-phenyl)-1-methyl-2-oxo-2,3-dihydro-1H-benzo[e][1,4]diazepin-5-yl]-benzonitrile Prepared from 3-(7-bromo-1-methyl-2-oxo-2,3-dihydro-1H-benzo[e][1,4]diazepin-5-yl)-benzonitrile Intermediate 14 using the same method described for Example 1 and instead of using benzene boronic acid, we used 3-methoxyphenyl boronic acid. The title compound (110 mg) was obtained as a yellow solid, (yield=58%).

TLC: (AcOEt/CH$_2$Cl$_2$: 3/7): Rf: 0.3 $^1$H NMR (CDCl$_3$, 200 MHz): δ 8.06-8.01 (m, 2H), 7.76-7.73 (m, 2H), 7.57-7.40 (m, 3H), 7.27-7.23 (m, 2H), 7.05-6.96 (m, 2H), 4.91-4.85 and 3.93-3.87 (AB system, J=10 Hz$_2$), 3.82 (s, 3H$_3$), 3.46 (s, 3H$_3$).

Example 14

3-[7-(4-Methoxy-phenyl)-1-methyl-2-oxo-2,3-dihydro-1H-benzo[e][1,4]diazepin-5-yl]-benzonitrile Prepared from 3-(7-bromo-1-methyl-2-oxo-2,3-dihydro-1H-benzo[e][1,4]diazepin-5-yl)-benzonitrile Intermediate 14 using the same method described for Example 1 and instead of using benzene boronic acid, we used 4-methoxyphenyl boronic acid. The title compound (90 mg) was obtained as a yellow solid, (yield=47%).

TLC: (AcOEt/CH$_2$Cl$_2$: 3/7): Rf: 0.3 $^1$H NMR (CDCl$_3$, 300 MHz): δ 7.99-7.94 (m, 2H), 7.80-7.76 (m, 2H), 7.56-7.50 (m, 1H), 7.45-7.36 (m, 4H), 6.98-6.95 (m, 2H), 4.90-4.87 and 3.90-3.84 (AB system, J=10 Hz$_2$), 3.84 (s, 3H), 3.46 (s, 3H).

Example 15

3-[7-(2,5-Dimethoxy-phenyl)-1-methyl-2-oxo-2,3-dihydro-1H-benzo[e][1,4]diazepin-5-yl]-benzonitrile Prepared from 3-(7-bromo-1-methyl-2-oxo-2,3-dihydro-1H-benzo[e][1,4]diazepin-5-yl)-benzonitrile Intermediate 14 using the same method described for Example 1 and instead of using benzene boronic acid, we used 2,5-dimethoxyphenyl boronic acid. The title compound was obtained as a yellow solid, (yield=65%).

TLC: (AcOEt/CH$_2$Cl$_2$: 3/7): Rf: 0.3 $^1$H NMR (CDCl$_3$, 300 MHz): δ 8.05-8.01 (m, 2H), 7.77-7.73 (m, 2H), 7.56-7.51 (m, 1H), 7.44-7.41 (m, 3H), 6.89-6.82 (m, 3H), 4.90-4.86 and 3.92-3.88 (AB system, J=10 Hz$_2$), 3.79 (s, 3H), 3.77 (s, 3H), 3.46 (s, 3H).

Example 16

3-[7-(2,6-Dimethoxy-phenyl)-1-methyl-2-oxo-2,3-dihydro-1H-benzo[e][1,4]diazepin-5-yl]-benzonitrile Prepared from 3-(7-bromo-1-methyl-2-oxo-2,3-dihydro-1H-benzo[e][1,4]diazepin-5-yl)-benzonitrile Intermediate 14 using the same method described for Example 1 and instead of using benzene boronic acid, we used 2,6-dimethoxyphenyl boronic acid. The title compound (148 mg) was obtained as a yellow solid, (yield=71%).

TLC: (AcOEt/CH$_2$Cl$_2$: 3/7): Rf: 0.3 $^1$H NMR (CDCl$_3$, 300 MHz): δ 8.13-8.10 (m, 1H), 7.98 (s, 1H), 7.75-7.73 (m, 1H), 7.63-7.51 (m, 2H), 7.43-7.40 (m, 1H), 7.33-7.27 (m, 2H), 6.66-6.63 (m, 2H), 4.90-4.86 and 3.99-3.95 (AB system, J=10 Hz$_2$), 3.79 (s, 6H), 3.48 (s, 3H).

Example 17

3-[7-(2,4-Dimethoxy-phenyl)-1-methyl-2-oxo-2,3-dihydro-1H-benzo[e][1,4]diazepin-5-yl]-benzonitrile Prepared from 3-(7-bromo-1-methyl-2-oxo-2,3-dihydro-1H-benzo[e][1,4]diazepin-5-yl)-benzonitrile Intermediate 14 using the same method described for Example 1 and instead of using benzene boronic acid, we used 2,4-dimethoxyphenyl boronic acid. The title compound (135 mg) was obtained as a yellow solid, (yield=49%).

TLC: (AcOEt/CH$_2$Cl$_2$: 3/7): Rf: 0.3 $^1$H NMR (CDCl$_3$, 300 MHz): δ 8.06-8.01 (m, 2H), 7.75-7.70 (m, 2H), 7.56-7.53 (m, 1H), 7.41-7.39 (m, 2H), 7.19-7.16 (m, 1H), 6.56-6.54 (m, 2H), 4.89-4.85 and 3.84-3.80 (AB system, J=10 Hz$_2$), 3.84 (s, 3H), 3.80 (s, 3H), 3.46 (s, 3H).

Example 18

8-Ethoxy-1-ethyl-5,7-diphenyl-1,3-dihydro-benzo[e][1,4]diazepin-2-one

Prepared from 7-bromo-8-ethoxy-1-ethyl-5-phenyl-1,3-dihydro-benzo[e][1,4]diazepin-2-one Intermediate 16 using the same method described for Example 1. The title compound was obtained as a beige solid, (yield=10%).

TLC: (Hexane/AcOEt: 1/1): Rf: 0.29 $^1$H NMR (CDCl$_3$, 300 MHz): δ 7.75-7.60 (m, 2H), 7.5-7.3 (m, 8H), 7.2-7.1 (m, 1H), 6.92 (s, 1H), 4.83-4.79 and 3.89-3.86 (AB system, J=10 Hz, 2H), 4.41-4.31 (m, 1H), 4.24-4.15 (m, 2H), 3.82-3.75 (m, 1H), 1.5-1.4 (m, 3H), 1.3-1.1 (m, 3H).

Example 40

5-(3-Chloro-phenyl)-1-methyl-7-phenyl-1,3-dihydro-benzo[e][1,4]diazepin-2-one

Prepared from 5-chloro-1-methyl-7-phenyl-1,3-dihydro-benzo[e][1,4]diazepin-2-one using the same method described for Example 9 and instead of using benzene boronic acid, we used 3-chlorophenyl boronic acid. The title compound was obtained as a pale yellow solid, (yield=37%).

TLC: (Hexane/AcOEt: 31): Rf: 0.22 1H NMR (CDCl3, 200 MHz): δ 7.81-7.72 (m, 2H), 7.70-7.28 (s, 10H), 4.88-4.83 and 3.88-3.83 (AB system, J=10.5 Hz, 2H), 3.45 (s, 3H).

Example 41

5-(2-Chloro-phenyl)-1-methyl-7-phenyl-1,3-dihydro-benzo[e][1,4]diazepin-2-one

Prepared from 5-chloro-1-methyl-7-phenyl-1,3-dihydro-benzo[e][1,4]diazepin-2-one using the same method described for Example 9 and instead of using benzene boronic acid, we used 2-chlorophenyl boronic acid. The title compound (115 mg) was obtained as a beige solid, (yield=61%).

TLC: (Hexane/AcOEt: 3/1): Rf: 0.11 1H NMR (CDCl3, 200 MHz): δ 8.00-7.28 (m, 12H), 4.95-4.90 and 3.98-3.93 (AB system, J=10.5 Hz, 2H), 3.53 (s, 3H).

Example 42

5-(4-Chloro-phenyl)-1-methyl-7-phenyl-1,3-dihydro-benzo[e][1,4]diazepin-2-one

Prepared from 5-chloro-1-methyl-7-phenyl-1,3-dihydro-benzo[e][1,4]diazepin-2-one using the same method described for Example 9 and instead of using 3-formylbenzene boronic acid, we used 4-chlorophenyl boronic acid. The title compound was obtained as a pale yellow solid, (yield=35%).

TLC: (Hexane/AcOEt: 3/1): Rf: 0.14 1H NMR (CDCl3, 200 MHz): δ 7.81-7.26 (m, 12H), 4.87-4.82 and 3.87-3.82 (AB system, J=10.5 Hz, 2H), 3.45 (s, 3H).

Example 43

3-(8-Methoxy-1-methyl-2-oxo-7-(4-cyanophenyl)-2,3-dihydro-1H-benzo[e][1,4]diazepin-5-yl)-benzonitrile

Prepared from 3-(7-bromo-8-methoxy-1-methyl-2-oxo-2,3-dihydro-1H-benzo[e][1,4]diazepin-5-yl)-benzonitrile Intermediate 9 using the same method described for Example 1 and instead of using benzene boronic acid, we used 4-cyanophenyl boronic acid. The title compound (25 mg) was obtained as a beige solid, (yield=14%).

TLC: (CH$_2$Cl$_2$/Et$_2$O: 1/1): Rf: 0.3 $^1$H NMR (CDCl$_3$, 300 MHz): δ 7.96-7.92 (m, 2H), 7.71-7.67 (m, 3H), 7.56-7.52 (m, 3H), 7.14 (s, 1H), 6.90 (s, 1H), 4.92-4.87 and 3.90-3.85 (AB system, J=10 Hz), 3.96 (s, 3H), 3.50 (s, 3H).

Example 48

3-[7-(4-Acetylphenyl)-8-methoxy-1-methyl-2-oxo-2,3-dihydro-1H-benzo[e][1,4]diazepin-5-yl]-benzonitrile

Prepared from 3-(7-bromo-8-methoxy-1-methyl-2-oxo-2,3-dihydro-1H-benzo[e][1,4]diazepin-5-yl)-benzonitrile Intermediate 9 using the same method described for Example 1 and instead of using benzene boronic acid, we used 4-acetylphenyl boronic acid. The title compound (83 mg) was obtained as a pale green solid, (yield=51%).

TLC: (Hexane/AcOEt: 1/1): Rf: 0.1 $^1$H NMR (CDCl$_3$, 300 MHz): δ 7.93-7.48 (m, 8H), 7.17 (s, 1H), 6.90 (s, 1H), 4.92-4.87 and 3.92-3.86 (AB system, J=11 Hz), 3.96 (s, 3H), 3.50 (s, 3H), 2.62 (s, 3H).

Example 50

5-(4-Methoxy-phenyl)-1-methyl-7-phenyl-1,3-dihydro-benzo[e][1,4]diazepin-2-one

Prepared from 5-chloro-1-methyl-7-phenyl-1,3-dihydro-benzo[e][1,4]diazepin-2-one using the same method described for Example 9 and instead of using 3-formylbenzene boronic acid, we used 4-methoxyphenyl boronic acid. The title compound (70 mg) was obtained as a white solid, (yield=47%).

TLC: (Hexane/AcOEt: 1/1): Rf: 0.35 1H NMR (CDCl3, 200 MHz): δ 7.80-7.27 (m, 10H), 6.93-6.89 (2s, 2H), 4.82-4.77 and 3.85-3.81 (AB system, J=10.5 Hz, 2H), 3.85 (s, 3H), 3.44 (s, 1H).

Example 51

5-(2-Methoxy-phenyl)-1-methyl-7-phenyl-1,3-dihydro-benzo[e][1,4]diazepin-2-one

Prepared from 5-chloro-1-methyl-7-phenyl-1,3-dihydro-benzo[e][1,4]diazepin-2-one using the same method described for Example 9 and instead of using 3-formylbenzene boronic acid, we used 2-methoxyphenyl boronic acid. The title compound (87 mg) was obtained as a beige solid, (yield=58%).

TLC: (Hexane/AcOEt: 1/1): Rf: 0.30 1H NMR (CDCl3, 200 MHz): δ 7.68-7.67 (m, 1H), 7.56-7.52 (s, 1H), 7.46-7.32 (m, 8H), 7.08-7.01 (m, 1H), 6.88-6.84 (m, 1H), 4.86-4.81 and 3.91-3.86 (AB system, J=10.5 Hz, 2H), 3.51 (s, 3H), 3.48 (s, 1H).

Example 52

3-[7-(Furan-2-yl)-1-methyl-2-oxo-2,3-dihydro-1H-benzo[e][1,4]diazepin-5-yl]-benzonitrile

Prepared from 3-(7-iodo-1-methyl-2-oxo-2,3-dihydro-1H-benzo[e][1,4]diazepin-5-yl)-benzonitrile Intermediate 11 using the same conditions used to prepare Example 1 but using 2-furanboronic acid instead of benzene boronic acid. The title compound (10 mg) was obtained as a brown solid, (yield=8%).
Rf (AcOEt/CH$_2$Cl$_2$: 3/7): 0.4 $^1$H NMR (CDCl$_3$, 300 MHz): δ 7.92-7.73 (m, 4H), 7.57-7.37 (m, 1H), 4.92-4.85 and 3.91-3.86 (AB system, J=10 Hz, 2H), 3.47 (s, 3H).

Example 53

3-[7-(3,4-Dimethoxy-phenyl)-1-methyl-2-oxo-2,3-dihydro-1H-benzo[e][1,4]diazepin-5-yl]-benzonitrile Prepared from 3-(7-iodo-1-methyl-2-oxo-2,3-dihydro-1H-benzo[e][1,4]diazepin-5-yl)-benzonitrile Intermediate 11 using the same conditions used to prepare Example 1 but using 3,4-dimethoxyphenyl boronic acid instead of benzene boronic acid. The title compound (110 mg) was obtained as a beige solid, (yield=72%).
Rf (AcOEt/CH$_2$Cl$_2$: 3/7): 0.3 $^1$H NMR (CDCl$_3$, 300 MHz): δ 7.99-7.98 (m, 2H), 7.77-7.73 (m, 2H), 7.56-7.53 (m, 1H), 7.44-7.35 (m, 2H), 7.03-6.92 (m, 3H), 4.91-4.87 and 3.91-3.90 (AB system, J=10 Hz, 2H), 3.91 (s, 3H), 3.90 (s, 3H), 3.46 (s, 3H).

Example 55

5-(3,5-Dichloro-phenyl)-1-methyl-7-phenyl-1,3-dihydro-benzo[e][1,4]diazepin-2-one Prepared from 5-chloro-1-methyl-7-phenyl-1,3-dihydro-benzo[e][1,4]diazepin-2-one using the same method described for Example 9 and instead of using 3-formylbenzene boronic acid, we used 3,5-dichlorophenyl boronic acid. The title compound (34 mg) was obtained as a beige solid, (yield=22%).
TLC: (Hexane/AcOEt: 1/1): Rf: 0.20 1H NMR (CDCl3, 200 MHz): δ 7.87-7.82 (m, 1H), 7.60-7.40 (m, 10H), 4.93-4.88 and 3.91-3.86 (AB system, J=10.5 Hz, 2H), 3.49 (s, 3H).

Example 56

5-(3,4-Dichloro-phenyl)-1-methyl-7-phenyl-1,3-dihydro-benzo[e][1,4]diazepin-2-one Prepared from 5-chloro-1-methyl-7-phenyl-1,3-dihydro-benzo[e][1,4]diazepin-2-one using the same method described for Example 9 and instead of using 3-formylbenzene boronic acid, we used 3,4-dichlorophenyl boronic acid. The title compound (46 mg) was obtained as a beige solid, (yield=30%).
TLC: (Hexane/AcOEt: 1/1): Rf: 0.13 1H NMR (CDCl3, 200 MHz): δ 7.88-7.82 (m, 2H), 7.48-7.40 (m, 9H), 4.92-4.87 and 3.91-3.86 (AB system, J=10.5 Hz, 2H), 3.49 (s, 3H).

Example 57

5-(4-Fluoro-phenyl)-1-methyl-7-phenyl-1,3-dihydro-benzo[e][1,4]diazepin-2-one

Prepared from 5-chloro-1-methyl-7-phenyl-1,3-dihydro-benzo[e][1,4]diazepin-2-one using the same method described for Example 9 and instead of using 3-formylbenzene boronic acid, we used 4-fluorophenyl boronic acid. The title compound (19 mg) was obtained as a beige solid, (yield=14%).
TLC: (Hexane/AcOEt: 1/1): Rf: 0.26 1H NMR (CDCl3, 300 MHz): δ 7.82-7.78 (m, 1H), 7.72-7.65 (m, 2H), 7.55-7.34 (m, 7H), 7.13-7.06 (m, 2H), 4.85-4.82 and 3.87-3.83 (AB system, J=10.5 Hz, 2H), 3.46 (s, 3H).

Example 58

5-(3-Acetyl-phenyl)-1-methyl-7-phenyl-1,3-dihydro-benzo[e][1,4]diazepin-2-one

Prepared from 5-chloro-1-methyl-7-phenyl-1,3-dihydro-benzo[e][1,4]diazepin-2-one using the same method described for Example 9 and instead of using 3-formylbenzene boronic acid, we used 3-acetylphenyl boronic acid. The title compound (44 mg) was obtained as a beige solid, (yield=31%).
TLC: (Hexane/AcOEt: 1/1): Rf: 0.25 1H NMR (CDCl3, 300 MHz): δ 8.30 (s, 1H), 8.10-8.00 (m, 1H), 7.98-7.75 (m, 2H), 7.52-7.34 (m, 8H), 4.91-4.87 and 3.91-3.87 (AB system, J=10.5 Hz, 2H), 3.48 (s, 3H), 2.64 (s, 3H).

Example 59

1-Methyl-7-phenyl-5-(3-trifluoromethyl-phenyl)-1,3-dihydro-benzo[e][1,4]diazepin-2-one Prepared from 5-chloro-1-methyl-7-phenyl-1,3-dihydro-benzo[e][1,4]diazepin-2-one using the same method described for Example 9 and instead of using 3-formylbenzene boronic acid, we used 3-trifluoromethylphenyl boronic acid. The title compound (30 mg) was obtained as a beige solid, (yield=20%).
TLC: (Hexane/AcOEt: 1/1): Rf: 0.1 1H NMR (CDCl3, 300 MHz): δ 8.05 (s, 1H), 7.92-7.70 (m, 3H), 7.51-7.30 (m, 8H), 4.92-4.88 and 3.91-3.87 (AB system, J=10.5 Hz, 2H), 3.50 (s, 3H).

Example 60

1-Methyl-5-(4-methyl-3-nitro-phenyl)-7-phenyl-1,3-dihydro-benzo[e][1,4]diazepin-2-one Prepared from 5-chloro-1-methyl-7-phenyl-1,3-dihydro-benzo[e][1,4]diazepin-2-one using the same method described for Example 9 and instead of using 3-formylbenzene boronic acid, we used (4-methyl-3-nitro)phenyl boronic acid. The title compound (36 mg) was obtained as a beige solid, (yield=24%).
TLC: (Hexane/AcOEt: 1/1): Rf: 0.1 1H NMR (CDCl3, 300 MHz): δ 8.29 (s, 1H), 7.91-7.81 (m, 2H), 7.52-7.30 (m, 8H), 4.91-4.88 and 3.90-3.87 (AB system, J=10.5 Hz, 2H), 3.48 (s, 3H).

Example 61

1-Methyl-7-phenyl-5-(4-trifluoromethoxy-phenyl)-1,3-dihydro-benzo[e][1,4]diazepin-2-one Prepared from 5-chloro-1-methyl-7-phenyl-1,3-dihydro-benzo[e][1,4]diazepin-2-one using the same method described for Example 9 and instead of using 3-formylbenzene boronic acid, we used (4-trifluoromethoxy)phenyl boronic acid. The title compound (13 mg) was obtained as a pale yellow solid, (yield=8%).
TLC: (Hexane/AcOEt: 1/1): Rf: 0.54 1H NMR (CDCl3, 300 MHz): δ 7.80-7.70 (m, 3H), 7.58-7.36 (m, 7H), 7.24 (s, 1H), 4.89-4.85 and 3.89-3.86 (AB system, J=10.5 Hz, 2H), 3.47 (s, 3H).

Example 63

3-[7-(2-isopropoxy-phenyl)-8-methoxy-1-methyl-2-oxo-2,3-dihydro-1H-benzo[e][1,4]diazepin-5-yl]-benzonitrile Prepared from 3-(7-bromo-8-methoxy-1-methyl-2-oxo-2,3-dihydro-1H-benzo[e][1,4]diazepin-5-yl)-benzonitrile Intermediate 9 using the same method described for Example 1 and instead of using benzene boronic acid, we used 2-isopropoxyphenyl boronic acid. The title compound (147 mg) was obtained as a white solid, (yield=86%).

TLC: (AcOEt): Rf: 0.8 $^1$H NMR (CDCl$_3$, 300 MHz): δ 7.94-7.92 (m, 2H), 7.72-7.69 (m, 1H), 7.53-7.47 (m, 1H), 7.33-7.29 (m, 1H), 7.16-7.14 (m, 1H), 7.08 (s, 1H), 6.99-6.94 (m, 2H), 6.84 (s, 1H), 4.88-4.85 and 3.92-3.90 (AB system, J=11 Hz), 4.52-4.40 (sept, 1H), 3.88 (s, 3H), 3.51 (s, 3H), 1.22-1.19 (m, 6H).

Example 64

5-(3,4-Dimethoxy-phenyl)-1-methyl-7-phenyl-1,3-dihydro-benzo[e][1,4]diazepin-2-one Prepared from 5-chloro-1-methyl-7-phenyl-1,3-dihydro-benzo[e][1,4]diazepin-2-one using the same method described for Example 9 and instead of using 3-formylbenzene boronic acid, we used 3,4-dimethoxyphenyl boronic acid. The title compound (88 mg) was obtained as a pale yellow solid, (yield=59%).

TLC: (AcOEt:): Rf: 0.56 1H NMR (CDCl3, 200 MHz): δ 7.91-7.85 (m, 1H), 7.58-7.26 (m, 8H), 7.05-7.00 (m, 1H), 6.83-6.79 (m, 1H), 4.83-4.78 and 3.92-3.87 (AB system, J=10.5 Hz, 2H), 3.97 (s, 3H), 3.45 (s, 3H).

Example 65

1-Methyl-5-(3-nitro-phenyl)-7-phenyl-1,3-dihydro-benzo[e][1,4]diazepin-2-one Prepared from 5-chloro-1-methyl-7-phenyl-1,3-dihydro-benzo[e][1,4]diazepin-2-one using the same method described for Example 9 and instead of using 3-formylbenzene boronic acid, we used 3-nitrophenyl boronic acid. The title compound (60 mg) was obtained as a beige solid, (yield=26%).

TLC: (AcOEt:): Rf: 0.56 1H NMR (CDCl3, 200 MHz): δ 8.53 (m, 1H), 8.34-8.30 (m, 1H), 8.10-8.06 (m, 1H), 7.84-7.80 (m, 1H), 7.65-7.28 (m, 8H), 4.95-4.89 and 3.93-3.87 (AB system, J=10.5 Hz, 2H), 3.48 (s, 3H).

Example 68

5-(3-Amino-phenyl)-1-methyl-7-phenyl-1,3-dihydro-benzo[e][1,4]diazepin-2-one 1-Methyl-5-(3-nitro-phenyl)-7-phenyl-1,3-dihydro-benzo[e][1,4]diazepin-2-one Example 65 (40 mg, 0.11 mmole)was dissolved in Methanol/CH2Cl2 then Pd/C (10 mg) was added and the flask was stirred over hydrogene atmosphere. The solution was filtered over celite, and the solvent was evaporated. The crude material was chromatographied: eluant: AcOEt/Hexane: 1/1. The title compound (6 mg) was obtained as a beige solid, (yield=16%).

TLC: (AcOEt:) Rf: 0.10 1H NMR (CDCl3, 200 MHz): δ 7.58-7.53 (m, 1H), 7.50-7.14 (m, 9H), 6.96-6.80 (m, 2H), 4.88-4.83 and 3.91-3.86 (AB system, J=10.5 Hz, 2H), 3.48 (s, 3H).

Example 69

3-(1-Methyl-2-oxo-8-phenoxy-7-phenyl-2,3-dihydro-1H-benzo[e][1,4]diazepin-5-yl)-benzonitrile Prepared from 3-(7-bromo-1-methyl-2-oxo-8-phenoxy-2,3-dihydro-1H-benzo[e][1,4]diazepin-5-yl)-benzonitrile Intermediate 15 using the same method described for Example 1.

The title compound (85 mg) was obtained as a pale beige solid, (yield=54%).

Rf (AcOEt/CH$_2$Cl$_2$: 1/2): 0.5 $^1$H NMR (CDCl$_3$, 200 MHz): δ 7.96 (s, 1H arom), 7.96-7.92 (m, 1H arom), 7.73-7.71 (m, 1H arom), 7.56-7.44 (m, 4H arom), 7.40-7.34 (m, 4H arom), 7.27-7.19 (m, 2H arom), 7.09-7.05 (m, 2H arom), 6.80 (s, 1H arom), 4.88-4.83 and 3.91-3.86 (AB system, J=10 Hz, CH$_2$), 3.90 (s, 3H, OCH$_3$), 3.24 (s, 3H, NCH$_3$).

Example 70

3-[7-(2-Methoxy-phenyl)-1-methyl-2-oxo-8-phenoxy-2,3-dihydro-1H-benzo[e][1,4]diazepin-5-yl]-benzonitrile Prepared from 3-(7-bromo-1-methyl-2-oxo-8-phenoxy-2,3-dihydro-1H-benzo[e][1,4]diazepin-5-yl)-benzonitrile Intermediate 15 using the same method described for Example 1. and instead of using benzene boronic acid, we used 2-methoxy-benzene boronic acid.

The title compound (100 mg) was obtained as a grey solid, (yield=63%).

Rf (AcOEt/CH$_2$Cl$_2$: 1/2): 0.4 $^1$H NMR (CDCl$_3$, 200 MHz): δ 8.07-8.03 (m, 1H arom), 7.99 (s, 1H arom), 7.76-7.73 (m, 1H arom), 7.58-7.54 (m, 1H arom), 7.43-7.17 (m, 6H arom), 7.10-6.91 (m, 4H arom), 6.83 (s, 1H arom), 4.90-4.85 and 3.97-3.93 (AB system, J=10 Hz, CH$_2$), 3.77 (s, 3H, OCH$_3$), 3.28 (s, 3H, NCH$_3$).

Example 71

3-[7-(2-Chloro-phenyl)-1-methyl-2-oxo-8-phenoxy-2,3-dihydro-1H-benzo[e][1,4]diazepin-5-yl]-benzonitrile Prepared from 3-(7-bromo-1-methyl-2-oxo-8-phenoxy-2,3-dihydro-1H-benzo[e][1,4]diazepin-5-yl)-benzonitrile Intermediate 15 using the same method described for Example 1. and instead of using benzene boronic acid, we used 2-chloro-benzene boronic acid.

The title compound (115 mg) was obtained as a yellow solid, (yield=72%).

Rf (AcOEt/CH$_2$Cl$_2$: 1/2): 0.4 $^1$H NMR (CDCl$_3$, 200 MHz): δ 7.99 (s, 2H arom), 7.75-7.72 (m, 1H arom), 7.56-7.51 (m, 1H arom), 7.45-7.33 (m, 4H arom), 7.31-7.19 (m, 4H arom), 7.09-7.06 (m, 2H arom), 6.80 (s, 1H arom), 4.90-4.85 and 3.97-3.93 (AB system, J=10 Hz, CH$_2$), 3.77 (s, 3H, OCH$_3$), 3.28 (s, 3H, NCH$_3$).

Example 75

7-(2,6-Dimethoxy-phenyl)-5-(4-methoxy-phenyl)-1-methyl-1,3-dihydro-benzo[e][1,4]diazepin-2-one Prepared from 5-chloro-1-methyl-7-(3,5-dimethoxy)-phenyl-1,3-dihydro-benzo[e][1,4]diazepin-2-one using the same method described for Example 9 and instead of using 3-formylbenzene boronic acid, we used 4-methoxyphenyl boronic acid. The title compound (26 mg) was obtained as a beige solid, (yield=15%).

TLC: (AcOEt:): Rf: 0.13 1H NMR (CDCl3, 300 MHz): δ 7.78-7.69 (m, 1H), 7.58-7.55 (m, 1H), 7.39-7.27 (m, 4H), 6.92-6.89 (m, 2H), 6.64-6.62 (m, 2H), 4.79-4.76 and 3.94-3.91 (AB system, J=10.5 Hz, 2H), 3.85 (s, 3H), 3.76 (s, 6H), 3.44 (s, 3H).

Example 77

7-(2,6-Dimethoxy-phenyl)-1-methyl-5-(4-methyl-3-nitro-phenyl)-1,3-dihydro-benzo[e][1,4]diazepin-2-one Prepared from 5-chloro-1-methyl-7-(3,5-dimethoxy)-phenyl-1,3-dihydro-benzo[e][1,4]diazepin-2-one using the same method described for Example 9 and instead of using 3-formylbenzene boronic acid, we used (4-methyl-3-nitrophenyl)-phenyl boronic acid. The title compound (64 mg) was obtained as a beige solid, (yield=33%).

1H NMR (CDCl3, 300 MHz): δ 8.27 (s, 1H), 7.98-7.96 (m, 1H), 7.60-7.57 (m, 1H), 7.42-7.37 (m, 2H), 7.29-7.26 (m, 2H), 6.64-6.62 (m, 2H), 4.88-4.85 and 3.98-3.94 (AB system, J=10.5 Hz, 2H), 3.74 (s, 6H), 3.48 (s, 3H), 2.64 (s, 3H).

Example 79

5-(3-Methoxy-phenyl)-1-methyl-7-phenyl-1,3-dihydro-benzo[e][1,4]diazepin-2-one

Prepared from 5-Chloro-1-methyl-7-phenyl-1,3-dihydro-benzo[e][1,4]diazepin-2-one using the same method described for Example 9 and instead of using 3-formylbenzene boronic acid, we used 3-methoxyphenyl boronic acid. The title compound (11 mg) was obtained as a yellow solid, (yield=10%).

TLC: (Hexane/AcOEt: 1/1): Rf: 0.22 1H NMR (CDCl3, 200 MHz): δ 7.88-7.72 (m, 1H), 7.84-7.29 (m, 9H), 7.19-7.15 (m, 1H), 7.08-7.02 (m, 1H) 4.91-4.86 and 3.92-3.88 (AB system, J=10.5 Hz, 2H), 3.88 (s, 3H), 3.49 (s, 1H).

Example 81

3-[7-(5-Chloro,2-methoxy-phenyl)-1-methyl-2-oxo-2,3-dihydro-1H-benzo[e][1,4]diazepin-5-yl]-benzonitrile Prepared from 3-(7-iodo-1-methyl-2-oxo-2,3-dihydro-1H-benzo[e][1,4]diazepin-5-yl)-benzonitrile Intermediate 11 using the same conditions used to prepare Example 1 but using 5-chloro, 2-methoxyphenyl boronic acid instead of benzene boronic acid. The title compound (85 mg) was obtained as a yellow solid, in 55% yield.

Rf (AcOEt/CH$_2$Cl$_2$: 3/7): 0.3 $^1$H NMR (CDCl$_3$, 300 MHz): δ 8.06-8.03 (m, 1H), 7.98 (s, 1H), 7.74-7.70 (m, 2H), 7.58-7.55 (m, 1H), 4.91-4.87 and 3.90-3.86 (AB system, J=10 Hz, 2H), 3.81 (s, 3H), 3.90 (s, 3H), 3.46 (s, 3H).

Example 82

3-[7-(2-Chloro,6-methoxy-phenyl)-1-methyl-2-oxo-2,3-dihydro-1H-benzo[e][1,4]diazepin-5-yl]-benzonitrile Prepared from 3-(7-iodo-1-methyl-2-oxo-2,3-dihydro-1H-benzo[e][1,4]diazepin-5-yl)-benzonitrile Intermediate 11 using the same conditions used to prepare Example 1 but using 2-chloro, 6-methoxyphenyl boronic acid instead of benzene boronic acid. The title compound (115 mg) was obtained as a beige solid, in 74% yield.

Rf (AcOEt/CH$_2$Cl$_2$: 3/7): 0.3 $^1$H NMR (CDCl$_3$, 300 MHz): δ 8.10-7.96 (m, 1H), 7.75-7.73 (m, 1H), 7.59-7.44 (m, 3H), 7.30-7.20 (m, 3H), 7.10-7.07 (m, 1H), 6.89-6.86 (m, 1H), 4.91-4.87 and 3.90-3.86 (AB system, J=10 Hz, 2H), 3.81 (s, 3H), 3.90 (s, 3H), 3.46 (s, 3H).

Example 88

3-[1-Methyl-2-oxo-7-(2-phenoxy-phenyl)-2,3-dihydro-1H-benzo[e][1,4]diazepin-5-yl]-benzonitrile Prepared from 3-(7-iodo-1-methyl-2-oxo-2,3-dihydro-1H-benzo[e][1,4]diazepin-5-yl)-benzonitrile Intermediate 11 using the same conditions used to prepare Example 1 but using 2-phenoxy-phenyl boronic acid instead of benzene boronic acid. The title compound (90 mg) was obtained as a beige solid, in 41% yield.

Rf (AcOEt/CH$_2$Cl$_2$: 3/7): 0.3 $^1$H NMR (CDCl$_3$, 200 MHz): δ 7.96 (m, 1H), 7.83-7.76 (m, 2H), 7.66-7.62 (m, 1H), 7.44-7.28 (m, 5H), 7.30-7.20 (m, 3H), 7.10-7.06 (m, 2H), 6.86-6.82 (m, 2H), 4.88-4.83 and 3.84-3.79 (AB system, J=10 Hz, 2H), 3.43 (s, 3H).

Example 89

3-[7-(2,6-Dimethoxy-phenyl)-8-methoxy-1-methyl-2-oxo-2,3-dihydro-1H-benzo[e][1,4]diazepin-5-yl]-benzonitrile Prepared from 3-(7-bromo-8-methoxy-1-methyl-2-oxo-2,3-dihydro-1H-benzo[e][1,4]diazepin-5-yl)-benzonitrile Intermediate 9 using the same method described for Example 1 and instead of using benzene boronic acid, we used 2,6-dimethoxyphenyl boronic acid. The title compound (83 mg) was obtained as a pale green solid, (yield=44%).

Rf (AcOEt/CH$_2$Cl$_2$: 3/7): 0.4 $^1$H NMR (CDCl$_3$, 400 MHz): δ 8.04-7.02 (m, 1H), 7.85 (s, 1H), 7.64-7.62 (m, 1H), 7.46-7.42 (m, 1H), 7.28-7.25 (m, 1H), 6.99 (s, 1H), 6.80 (s, 1H), 6.59-6.52 (m, 2H), 4.79-4.77 and 3.92-3.89 (AB system, J=12 Hz, 2H), 3.80 (s, 3H), 3.78 (s, 3H), 3.63 (s, 3H), 3.42 (s, 3H).

Example 90

3-[8-Methoxy-1-methyl-2-oxo-7-(2-phenoxy-phenyl)-2,3-dihydro-1H-benzo[e][1,4]diazepin-5-yl]-benzonitrile Prepared from 3-(7-bromo-8-methoxy-1-methyl-2-oxo-2,3-dihydro-1H-benzo[e][1,4]diazepin-5-yl)-benzonitrile Intermediate 9 using the same method described for Example 1 and instead of using benzene boronic acid, we used 2-phenoxy-phenyl boronic acid The title compound (120 mg) was obtained as a pale green solid, (yield=72%).

Rf (AcOEt/CH$_2$Cl$_2$: 3/7): 0.5 $^1$H NMR (CDCl$_3$, 400 MHz): δ 7.98 (s, 1H), 7.84-7.82 (m, 1H), 7.70-7.68 (m, 1H), 7.39-7.28 (m, 5H), 7.18-7.16 (m, 2H), 7.18-7.16 (m, 1H), 7.00-6.98 (m, 1H), 6.92-6.90 (m, 2H), 6.82 (s, 1H), 4.88-4.85 and 3.88-3.85 (AB system, J=12 Hz, 2H), 3.85 (s, 3H), 3.48 (s, 3H).

Example 99

5-(3,4-Dichloro-phenyl)-7-(2,6-dimethoxy-phenyl)-1-methyl-1,3-dihydro-benzo[e][1,4]diazepin-2-one Prepared from 5-Chloro-7-(2,6-dimethoxy-phenyl)-1-methyl-1,3-dihydro-benzo[e][1,4]diazepin-2-one The title compound (55 mg) was obtained as a beige solid, (yield=28%).

TLC: (H/AcOEt: 1/1): Rf: 0.2 1H NMR (CDCl3, 300 MHz): δ 7.86-7.83 (m, 1H), 7.65-7.23 (m, 6H), 6.65-6.62 (m, 2H), 4.85-4.81 and 3.95-3.91 (AB system, J=10.5 Hz, 2H), 3.80-3.73 (m, 6H), 3.49 (s, 3H).

Example 100

7-(2,6-Dimethoxy-phenyl)-5-(4-fluoro-phenyl)-1-methyl-1,3-dihydro-benzo[e][1,4]diazepin-2-one Prepared from 5-Chloro-7-(2,6-dimethoxy-phenyl)-1-methyl-1,3-dihydro-benzo[e][1,4]diazepin-2-one The title compound (58 mg) was obtained as a beige solid, (yield=33%).

TLC: (H/AcOEt: 1/1): Rf: 0.3 1H NMR (CDCl3, 300 MHz): δ 7.77-7.72 (m, 2H), 7.60-7.56 (m, 1H), 7.38-7.25 (m, 3H), 7.10-7.04 (m, 2H), 6.65-6.62 (m, 2H), 4.84-4.81 and 3.96-3.92 (AB system, J=10.5 Hz, 2H), 3.80-3.70 (m, 6H), 3.47 (s, 3H).

Example 101

5-(3,4-Dimethoxy-phenyl)-7-(2,6-dimethoxy-phenyl)-1-methyl-1,3-dihydro-benzo[e][1,4]diazepin-2-one Prepared from 5-Chloro-7-(2,6-dimethoxy-phenyl)-1-methyl-1,3-dihydro-benzo[e][1,4]diazepin-2-one.

The title compound (71 mg) was obtained as a orange solid, (yield=37%).

TLC: (H/AcOEt: 1/1): Rf: 0.2 1H NMR (CDCl3, 300 MHz): δ 7.77-7.27 (m, 5H), 7.17-7.13 (m, 1H), 6.83-6.80 (m, 1H), 6.65-6.62 (m, 2H), 4.80-4.76 and 3.80-3.70 (AB system, J=10.5 Hz, 2H), 4.15-3.85 (m, 6H), 3.73 (s, 3H).

Example 115

7-(2,6-Dimethoxy-phenyl)-1-methyl-5-m-tolyl-1,3-dihydro-benzo[e][1,4]diazepin-2-one Prepared from 5-Chloro-7-(2,6-dimethoxy-phenyl)-1-methyl-1,3-dihydro-benzo[e][1,4]diazepin-2-one.

The title compound (71 mg) was obtained as a orange solid, (yield=41%).

TLC: (H/AcOEt: 1/1): Rf: 0.4 1H NMR (CDCl3, 300 MHz): δ 7.62-7.55 (m, 2H), 7.42-7.26 (m, 6H), 6.63-6.61 (m, 2H), 4.80-4.76 and 3.80-3.70 (AB system, J=10.5 Hz, 2H), 3.85 (s, 6H), 3.48 (s, 3H), 2.39 (s, 3H).

Example 108

8-Methoxy-5-(4-methoxy-phenyl)-1-methyl-7-(2-methoxy-phenyl)-1,3-dihydro-benzo[e][1,4]diazepin-2-one Prepared from 7-Bromo-8-methoxy-5-(4-methoxy-phenyl)-1-methyl-1,3-dihydro-benzo[e][1,4]diazepin-2-one The title compound (13 mg) was obtained as a yellowish solid, (yield=8%).

TLC: (H/AcOEt: 1/1): Rf: 0.1 1H NMR (CDCl3, 300 MHz): δ 7.69-7.55 (m, 3H), 7.41-7.37 (m, 3H), 7.30-7.12 (m, 2H), 6.92-6.75 (s, 2H), 4.71-4.69 and 3.82-3.79 (AB system, J=10.5 Hz, 2H), 3.82 (s, 3H), 3.80 (s, 3H), 3.76 (s, 3H), 3.39 (s, 3H).

Example 109

7-(2,6-Dimethoxy-phenyl)-8-methoxy-5-(4-methoxy-phenyl)-1-methyl-1,3-dihydro-benzo[e][1,4]diazepin-2-one Prepared from 7-Bromo-8-methoxy-5-(4-methoxy-phenyl)-1-methyl-1,3-dihydro-benzo[e][1,4]diazepin-2-one Intermediate 23.

The title compound (29 mg) was obtained as a beige solid, (yield=17%).

TLC: (H/AcOEt: 1/1): Rf: 0.1 1H NMR (CDCl3, 300 MHz): δ 7.61-7.58 (m, 2H), 7.50-7.45 (m, 1H), 6.79 (s, 1H), 6.79-6.75 (m, 3H), 6.56-6.51 (m, 2H), 4.70-4.67 and 3.87-3.84 (AB system, J=10.5 Hz, 2H), 3.78-3.73 (m, 9H), 3.62 (s, 3H), 3.39 (s, 3H).

Example 110

7-(2,5-Dimethoxy-phenyl)-8-methoxy-5-(4-methoxy-phenyl)-1-methyl-1,3-dihydro-benzo[e][1,4]diazepin-2-one Prepared from 7-Bromo-8-methoxy-5-(4-methoxy-phenyl)-1-methyl-1,3-dihydro-benzo[e][1,4]diazepin-2-one The title compound (7 mg) was obtained as a beige solid, (yield=4%).

TLC: (H/AcOEt: 1/1): Rf: 0.1 1H NMR (CDCl3, 400 MHz): δ 7.66-7.64 (m, 2H), 7.56-7.46 (m, 2H), 7.24 (s, 1H), 6.90-6.78 (m, 4H), 4.80-4.77 and 3.87-3.84 (AB system, J=10.5 Hz, 2H), 3.89-3.73 (m, 12H), 3.47 (s, 3H).

Example 111

7-(2-Fluoro-6-methoxy-phenyl)-8-methoxy-5-(4-methoxy-phenyl)-1-methyl-1,3-dihydro-benzo[e][1,4]diazepin-2-one Prepared from 7-Bromo-8-methoxy-5-(4-methoxy-phenyl)-1-methyl-1,3-dihydro-benzo[e][1,4]diazepin-2-one The title compound (3 mg) was obtained as a beige solid, (yield=3%).

TLC: (H/AcOEt: 1/1): Rf: 0.2 1H NMR (CDCl3, 400 MHz): δ 7.68-7.60 (m, 2H), 7.26-7.24 (m, 2H), 6.90-6.73 (m, 5H), 4.79-4.76 and 3.88-3.85 (AB system, J=10.5 Hz, 2H), 3.91-3.83 (s, 9H), 3.47 (s, 3H).

Example 112

8-Methoxy-5-(4-methoxy-phenyl)-1-methyl-7-(2-phenoxy-phenyl)-1,3-dihydro-benzo[e][1,4]diazepin-2-one Prepared from 7-Bromo-8-methoxy-5-(4-methoxy-phenyl)-1-methyl-1,3-dihydro-benzo[e][1,4]diazepin-2-one The title compound (10 mg) was obtained as a yellowish solid, (yield=8%).

TLC: (H/AcOEt: 1/1): Rf: 0.2 1H NMR (CDCl3, 400 MHz): δ 7.68-7.60 (m, 2H), 7.26-7.24 (m, 2H), 7.16-6.75 (m,

9H), 4.77-4.75 and 3.86-3.83 (AB system, J=10.5 Hz, 2H), 3.86-3.79 (m, 6H), 3.42 (s, 3H).

Preparation of Examples of General Formula I (Scheme 6)

Example 35

3-[1-Hexyl-8-methoxy-7-(2-methoxy-phenyl)-2-oxo-2,3-dihydro-1H-benzo[e][1,4]diazepin-5-yl]-benzonitrile To a mixture of toluene (6 mL) and Aliquat 336 (2 μL) was introduced hexyl bromine (70 μL, 0.499 mmole) while the mixture was agitated, powdered 3-[8-methoxy-7-(2-methoxy-phenyl)-2-oxo-2,3-dihydro-1H-benzo[e][1,4]diazepin-5-yl]-benzonitrile Example 10 (100 mg, 0.25 mmole) and 50% aqueous sodium hydroxide (0.27 mL) were added to the reaction mixture. The two-phase system was stirred vigorously for 4 hours. The phases were separated, and the aqueous layer was extracted with ethyl acetate (20 mL). The combined organic extracts were washed with cold water (10 mL); then the organic phase were dried over $Na_2SO_4$ and concentrated to dryness. The title compound was crystallised from $Et_2O$/Pentane to afford 80 mg of a white powder—yield: 66%.

TLC: ($CH_2Cl_2/Et_2O$: 1/1): Rf: 0.8 $^1$H NMR ($CDCl_3$, 300 MHz): δ 8.04-7.93 (m, 2H), 7.74-7.71 (m, 1H), 7.52-7.49 (m, 1H), 7.36-7.31 (m, 1H), 7.23-7.20 (m, 1H), 7.13 (s, 1H), 7.02-6.96 (m, 2H), 6.94 (s, 1H), 4.84-4.81 and 3.93-3.90 (AB system, J=10 Hz), 3.88 (s, 3H), 3.81 (s, 3H), 4.42-4.33 and 3.74-3.65 (AB system, 2H), 1.57 (m, 2H), 1.18 (m, 6H), 0.81-0.76 (s, 3H).

Example 37

3-[8-Methoxy-7-(2-methoxy-phenyl)-2-oxo-1-propyl-2,3-dihydro-1H-benzo[e][1,4]diazepin-5-yl]-benzonitrile Prepared from 3-[8-methoxy-7-(2-methoxy-phenyl)-2-oxo-2,3-dihydro-1H-benzo[e][1,4]diazepin-5-yl]-benzonitrile Example 10 using the same method described for Example 35 using propyl iodide instead of hexyl bromine. The title compound (99 mg) was obtained as a white solid, yield=89%.

TLC: ($CH_2Cl_2/Et_2O$: 1/1): Rf: 0.7 $^1$H NMR ($CDCl_3$, 200 MHz): δ 8.04-7.93 (m, 2H), 7.74-7.71 (m, 1H), 7.56-7.48 (m, 1H), 7.38-7.30 (m, 1H), 7.23-7.20 (m, 1H), 7.12 (s, 1H), 7.02-6.96 (m, 2H), 6.94 (s, 1H), 4.86-4.81 and 3.93-3.90 (AB system, J=10 Hz, 2H), 3.88 (s, 3H), 3.80 (s, 3H), 4.42-4.32 and 3.74-3.65 (AB system, 2H), 1.60 (m, 2H), 0.86-0.79 (s, 3H).

Example 38

3-[8-Methoxy-7-(2-methoxy-phenyl)-2-oxo-1-phenethyl-2,3-dihydro-1H-benzo[e][1,4]diazepin-5-yl]-benzonitrile Prepared from 3-[8-methoxy-7-(2-methoxy-phenyl)-2-oxo-2,3-dihydro-1H-benzo[e][1,4]diazepin-5-yl]-benzonitrile Example 10 using the same method described for Example 35 using phenethyl bromine instead of hexyl bromine. The title compound (110 mg) was obtained as a white solid, (yield=87%).

TLC: ($CH_2Cl_2/Et_2O$: 1/1): Rf: 0.8 $^1$H NMR ($CDCl_3$, 200 MHz): δ 7.96-7.92 (m, 1H), 7.72-7.70 (m, 2H), 7.53-7.45 (m, 1H), 7.37-7.29 (m, 1H), 7.20-7.15 (m, 6H), 7.06 (s, 1H), 7.01-6.94 (m, 2H), 6.82 (s, 1H), 4.59-4.49 and 4.09-3.99 (AB system, 2H), 4.87-4.82 and 3.93-3.88 (AB system, J=9 Hz, 2H), 3.88 (s, 3H), 3.80 (s, 3H), 3.05-2.98 (t, 2H).

Example 39

3-[1-Benzyl-8-methoxy-7-(2-methoxy-phenyl)-2-oxo-2,3-dihydro-1H-benzo[e][1,4]diazepin-5-yl]-benzonitrile Prepared from 3-[8-methoxy-7-(2-methoxy-phenyl)-2-oxo-2,3-dihydro-1H-benzo[e][1,4]diazepin-5-yl]-benzonitrile Example 10 using the same method described for Example 35 using benzyl bromine instead of hexyl bromine, we. The title compound (95 mg) was obtained as a yellow solid, (yield=90%).

TLC: ($CH_2Cl_2/Et_2O$: 1/1): Rf: 0.8 $^1$H NMR ($CDCl_3$, 200 MHz): δ 7.89-7.85 (m, 1H), 7.73-7.67 (m, 2H), 7.53-7.49 (m, 1H), 7.30-7.20 (m, 5H), 7.03-6.91 (m, 2H), 5.39-5.31 and 5.11-5.03 (AB system, J=10 Hz, 2H), 4.97-4.92 and 4.07-4.02 (AB system, J=10 Hz, 2H), 3.75 (s, 3H), 3.70 (s, 3H).

Preparation of Examples of General Formula I (Scheme 7)

Example 19

3-(8-Methoxy-1-methyl-2-oxo-7-phenyl-2,3-dihydro-1H-benzo[e][1,4]diazepin-5-yl)-benzamide To a solution of compound 3-(8-methoxy-1-methyl-2-oxo-7-phenyl-2,3-dihydro-1H-benzo[e][1,4]diazepin-5-yl)-benzonitrile Example 1 (46 mg, 0.12 mmol) in absolute ethanol (2 ml), were added dropwise $H_2O_2$ aqueous (30% wt in water, 42 μl), followed by aqueous NaOH (0.5 M, 60 μl). The solution was stirred at RT for 16 hours. Removal of ethanol in vacuum gave the crude material which was purified by silica gel column chromatography with $CH_2Cl_2$/MeOH: 95/5 to give after crystallization from ether/pentane the title compound (27 mg) as a white solid, (yield=72%).

TLC: ($CH_2Cl_2$/MeOH: 9/1): Rf: 0.2 mp 191-192° C. HPLC 99.2% $^1$H NMR ($CDCl_3$, 200 MHz): δ 8.14 (m, 1H), 7.91-7.95 (m, 1H), 7.78-7.83 (m, 1H), 7.53-7.45 (m, 1H), 7.34-7.41 (m, 5H), 7.19 (s, 1H), 6.87 (s, 1H), 6.12 and 5.69 (2 s-broad, 2H), 4.88-4.83 and 3.93-3.87 (AB system, J=10 $Hz_2$), 3.94 (s, 3H), 3.50 (s, 3H).

Example 20

3-[7-(4-Fluoro-phenyl)-8-methoxy-1-methyl-2-oxo-2,3-dihydro-1H-benzo[e][1,4]diazepin-5-yl]-benzamide Prepared from 3-[7-(4-fluorophenyl)-8-methoxy-1-methyl-2-oxo-2,3-dihydro-1H-benzo[e][1,4]diazepin-5-yl]-benzonitrile Example 2 using the same method described for Example 19. The title compound (35 mg) was obtained as a white solid, (yield=78%).

TLC: ($CH_2Cl_2$/MeOH: 9/1): Rf: 0.2 $^1$H NMR ($CDCl_3$, 200 MHz): δ 8.14 (m, 1H), 7.94-7.90 (m, 1H), 7.82-7.79 (m, 1H), 7.53-7.36 (m, 3H), 7.16 (s, 1H), 7.11-7.02 (s, 2H), 6.87 (s, 1H), 6.20 and 5.73 (2 s-broad, 2H), 4.88-4.83 and 3.91-3.86 (AB system, J=11 $Hz_2$), 3.94 (s, 3H), 3.49 (s, 3H).

Example 21

3-[8-Methoxy-7-(2-methoxy-phenyl)-1-methyl-2-oxo-2,3-dihydro-1H-benzo[e][1,4]diazepin-5-yl]-benzamide

Prepared from 3-[8-methoxy-7-(2-methoxy-phenyl)-1-methyl-2-oxo-2,3-dihydro-1H-benzo[e][1,4]diazepin-5-yl]-benzonitrile Example 3 using the same method described for Example 19. The title compound (50 mg) was obtained as a white solid, yield=83%.

TLC: ($CH_2Cl_2$/MeOH: 9/1): Rf: 0.2 $^1$H NMR ($CDCl_3$, 300 MHz): δ 8.13 (m, 1H), 7.95-7.92 (m, 1H), 7.85-7.82 (m, 1H), 7.51-7.46 (m, 1H), 7.35-7.29 (s, 1H), 7.21-7.17 (s, 2H), 7.00-6.94 (m, 2H), 6.86 (s, 1H), 6.16 and 5.63 (2 s-broad, 2H), 4.86-4.82 and 3.95-3.91 (AB system, J=11 $Hz_2$), 3.89 (s, 3H), 3.76 (s, 3H), 3.50 (s, 3H).

Example 22

3-[8-Methoxy-7-(4-methoxy-phenyl)-1-methyl-2-oxo-2,3-dihydro-1H-benzo[e][1,4]diazepin-5-yl]-benzamide

Prepared from 3-[8-methoxy-7-(4-methoxy-phenyl)-1-methyl-2-oxo-2,3-dihydro-1H-benzo[e][1,4]diazepin-5-yl]-benzonitrile Example 4 using the same method described for Example 19. The title compound (47 mg) was obtained as a white solid, yield=71%.

TLC: ($CH_2Cl_2$/MeOH: 9/1): Rf: 0.2 $^1$H NMR ($CDCl_3$, 200 MHz): δ 8.14 (m, 1H), 7.95-7.91 (m, 1H), 7.85-7.78 (m, 1H), 7.55-7.45 (m, 1H), 7.39-7.35 (m, 2H), 7.16 (s, 1H), 6.94-6.89 (m, 2H), 6.85 (s, 1H), 6.24 and 5.65 (2 s-broad, 2H), 4.87-4.82 and 3.92-3.87 (AB system, J=11 $Hz_2$), 3.94 (s, 3H), 3.82 (s, 3H), 3.49 (s, 3H).

Example 23

3-[7-(2-Chloro-phenyl)-8-methoxy-1-methyl-2-oxo-2,3-dihydro-1H-benzo[e][1,4]diazepin-5-yl]-benzamide

Prepared from 3-[7-(2-Chloro-phenyl)-8-methoxy-1-methyl-2-oxo-2,3-dihydro-1H-benzo[e][1,4]diazepin-5-yl]-benzonitrile Example 5 using the same method described for Example 19. The title compound (74 mg) was obtained as a white solid, yield=84%.

TLC: ($CH_2Cl_2$/MeOH: 9/1): Rf: 0.2 $^1$H NMR ($CDCl_3$, 300 MHz): δ 8.09 (m, 1H), 7.95-7.92 (m, 1H), 7.87-7.84 (m, 1H), 7.71-7.65 (m, 1H), 7.56-7.42 (m, 3H), 7.30-7.28 (m, 1H), 7.12 (s, 1H), 6.87 (s, 1H), 6.17 and 5.65 (2 s-broad, 2H), 4.88-4.85 and 3.94-3.90 (AB system, J=11 $Hz_2$), 3.90 (s, 3H), 3.51 (s, 3H).

Example 24

3-[7-(3-Chloro-phenyl)-8-methoxy-1-methyl-2-oxo-2,3-dihydro-1H-benzo[e][1,4]diazepin-5-yl]-benzamide

Prepared from 3-[7-(3-Chloro-phenyl)-8-methoxy-1-methyl-2-oxo-2,3-dihydro-1H-benzo[e][1,4]diazepin-5-yl]-benzonitrile Example 6 using the same method described for Example 19. The title compound (30 mg) was obtained as a white solid, yield=64%.

TLC: ($CH_2Cl_2$/MeOH: 9/1): Rf: 0.2 $^1$H NMR ($CDCl_3$, 200 MHz): δ 8.13 (m, 1H), 7.94-7.90 (m, 1H), 7.82-7.79 (m, 1H), 7.54-7.44 (m, 2H), 7.30 (m, 3H), 7.17 (s, 1H), 6.87 (s, 1H), 6.15 and 5.70 (2 s-broad, 2H), 4.89-4.84 and 3.91-3.85 (AB system, J=11 $Hz_2$), 3.95 (s, 3H), 3.49 (s, 3H).

Example 25

3-[7-(4-Chloro-phenyl)-8-methoxy-1-methyl-2-oxo-2,3-dihydro-1H-benzo[e][1,4]diazepin-5-yl]-benzamide

Prepared from 3-[7-(4-Chloro-phenyl)-8-methoxy-1-methyl-2-oxo-2,3-dihydro-1H-benzo[e][1,4]diazepin-5-yl]-benzonitrile Example 7 using the same method described for Example 19. The title compound (22 mg) was obtained as a white solid, yield=64%.

TLC: ($CH_2Cl_2$/MeOH: 9/1): Rf: 0.2 $^1$H NMR (CDCl3, 200 MHz): δ 8.14 (m, 1H), 7.94-7.78 (m, 2H), 7.53-7.45 (m, 1H), 7.35 (m, 4H), 7.16 (s, 1H), 6.87 (s, 1H), 6.20 and 5.75 (2 s-broad, 2H), 4.88-4.83 and 3.91-3.86 (AB system, J=11 $Hz_2$), 3.94 (s, 3H), 3.49 (s, 3H).

Example 26

3-(7-Furan-2-yl-8-methoxy-1-methyl-2-oxo-2,3-dihydro-1H-benzo[e][1,4]diazepin-5-yl)-benzamide

Prepared from 3-(7-furan-2-yl-8-methoxy-1-methyl-2-oxo-2,3-dihydro-1H-benzo[e][1,4]diazepin-5-yl)-benzonitrile Example 8 using the same method described for Example 19. The title compound (12 mg) was obtained as a white solid, yield=46%.

TLC: ($CH_2Cl_2$/MeOH: 9/1): Rf: 0.2 $^1$H NMR ($CDCl_3$, 300 MHz): δ 8.08 (m, 1H), 7.93-7.95 (m, 1H), 7.77-7.80 (m, 1H), 7.47-7.53 (m, 1H), 7.19-7.22 (d, J=9 Hz, 1H), 6.84-6.85 (d, J=2 Hz, 1H), 6.75-6.80 (dd, J=2 Hz and 9 Hz, 1H), 5.64 and 6.20 (2 s-broad, 2H), 3.80-3.84 and 4.79-4.83 (AB system, J=10 $Hz_2$), 3.91 (s, 3H), 3.43 (s, 3H).

Example 27

3-(1-methyl-2-oxo-7-phenyl-2,3-dihydro-1H-benzo[e][1,4]diazepin-5-yl)-benzamide

Prepared from 3-(1-methyl-2-oxo-7-phenyl-2,3-dihydro-1H-benzo[e][1,4]diazepin-5-yl)-benzonitrile Example 11 using the same method described for Example 19. The title compound (26 mg) was obtained as a yellow solid, yield=70%.

$^1$H NMR ($CDCl_3$, 200 MHz): δ 8.18 (s, 1H), 7.97-7.94 (m, 1H), 7.83-7.78 (m, 2H), 7.54-7.35 (m, 8H), 6.19 and 5.58 (2 s-broad, 2H), 4.90-4.84 and 3.91-3.86 (AB system, J=10 $Hz_2$), 3.47 (s, 3H).

Example 28

3-[7-(2-methoxy-phenyl)-1-methyl-2-oxo-2,3-dihydro-1H-benzo[e][1,4]diazepin-5-yl]-benzamide

Prepared from 3-[7-(2-methoxy-phenyl)-1-methyl-2-oxo-2,3-dihydro-1H-benzo[e][1,4]diazepin-5-yl]-benzonitrile Example 12 using the same method described for Example 19. The title compound (32 mg) was obtained as a yellow solid, yield=80%.

$^1$H NMR ($CDCl_3$, 300 MHz): δ 8.18 (m, 1H), 7.98-7.96 (m, 1H), 7.86-7.83 (m, 1H), 7.76-7.73 (m, 1H), 7.50-7.40 (m, 3H), 7.27-7.24 (m, 2H), 7.01-6.97 (m, 2H), 6.25 and 5.21 (2 s-broad, 2H), 4.87-4.84 and 3.93-3.89 (AB system, J=10 Hz₂), 3.77 (s, 3H), 3.47 (s, 3H).

Example 29

3-[7-(3-methoxy-phenyl)-1-methyl-2-oxo-2,3-dihydro-1H-benzo[e][1,4]diazepin-5-yl]-benzamide Prepared from 3-[7-(3-methoxy-phenyl)-1-methyl-2-oxo-2,3-dihydro-1H-benzo[e][1,4]diazepin-5-yl]-benzonitrile Example 13 using the same method described for Example 19. The title compound (50 mg) was obtained as a yellow solid, yield=80%.
$^1$H NMR (CDCl₃, 200 MHz): δ 8.19 (m, 1H), 7.94-7.92 (m, 1H), 7.81-7.76 (m, 2H), 7.54-7.34 (m, 4H), 7.08-6.92 (m, 3H), 6.28 and 5.22 (2 s-broad, 2H), 4.90-4.85 and 3.91-3.85 (AB system, J=10 Hz₂), 3.85 (s, 3H), 3.47 (s, 3H).

Example 30

3-[7-(4-methoxy-phenyl)-1-methyl-2-oxo-2,3-dihydro-1H-benzo[e][1,4]diazepin-5-yl]-benzamide Prepared from 3-[7-(4-methoxy-phenyl)-1-methyl-2-oxo-2,3-dihydro-1H-benzo[e][1,4]diazepin-5-yl]-benzonitrile Example 14 using the same method described for Example 19. The title compound (37 mg) was obtained as a yellow solid, yield=71%.
$^1$H NMR (CDCl₃, 300 MHz): δ 8.18 (m, 1H), 7.97-7.94 (m, 1H), 7.81-7.73 (m, 2H), 7.52-7.40 (m, 5H), 6.96-6.94 (m, 2H), 6.23 and 5.24 (2 s-broad, 2H), 4.88-4.85 and 3.90-3.86 (AB system, J=10 Hz₂), 3.84 (s, 3H), 3.46 (s, 3H).

Example 31

3-[7-(2,5-Dimethoxy-phenyl)-1-methyl-2-oxo-2,3-dihydro-1H-benzo[e][1,4]diazepin-5-yl]-benzamide Prepared from 3-[7-(2,5-dimethoxy-phenyl)-1-methyl-2-oxo-2,3-dihydro-1H-benzo[e][1,4]diazepin-5-yl]-benzonitrile Example 9 using the same method described for Example 19. The title compound (50 mg) was obtained as a yellow solid, yield=80%.
$^1$H NMR (CDCl₃, 300 MHz): δ 8.18 (m, 1H), 7.98-7.96 (m, 1H), 7.88-7.85 (m, 1H), 7.76-7.72 (m, 1H), 7.53-7.39 (m, 3H), 6.88-6.83 (m, 3H), 6.01 and 5.71 (2 s-broad, 2H), 4.88-4.84 and 3.93-3.89 (AB system, J=11 Hz₂), 3.78 (s, 3H), 3.71 (s, 3H), 3.47 (s, 3H).

Example 32

3-[7-(2,6-Dimethoxy-phenyl)-1-methyl-2-oxo-2,3-dihydro-1H-benzo[e][1,4]diazepin-5-yl]-benzamide Prepared from 3-[7-(2,6-dimethoxy-phenyl)-1-methyl-2-oxo-2,3-dihydro-1H-benzo[e][1,4]diazepin-5-yl]-benzonitrile Example 16 using the same method described for Example 19. The title compound (82 mg) was obtained as a yellow solid, yield=87%.
1H NMR (CDCl₃, 300 MHz): δ 8.17 (m, 1H), 7.98-7.95 (m, 1H), 7.87-7.85 (m, 1H), 7.60-7.57 (m, 1H), 7.51-7.48 (m, 1H), 7.40-7.37 (m, 1H), 7.30-7.24 (m, 2H), 6.64-6.61 (m, 2H), 6.17 and 5.76 (2 s-broad, 2H), 4.86-4.83 and 3.98-3.94 (AB system, J=11 Hz₂), 3.81 (s, 6H), 3.48 (s, 3H).

Example 33

3-[7-(2,4-Dimethoxy-phenyl)-1-methyl-2-oxo-2,3-dihydro-1H-benzo[e][1,4]diazepin-5-yl]-benzamide Prepared from 3-[7-(2,4-dimethoxy-phenyl)-1-methyl-2-oxo-2,3-dihydro-1H-benzo[e][1,4]diazepin-5-yl]-benzonitrile Example 17 using the same method described for Example 19. The title compound (45 mg) was obtained as a yellow solid, yield=72%.
1H NMR (CDCl₃, 300 MHz): δ 8.18 (m, 1H), 7.98-7.95 (m, 1H), 7.87-7.84 (m, 1H), 7.72-7.69 (m, 1H), 7.52-7.49 (m, 1H), 7.44-7.38 (m, 2H), 7.19-7.16 (m, 1H), 6.55-6.53 (m, 2H), 6.17 and 5.66 (2 s-broad, 2H), 4.87-4.83 and 3.92-3.88 (AB system, J=11 Hz₂), 3.83 (s, 3H), 3.75 (s, 3H), 3.46 (s, 3H).

Example 34

3-[8-Methoxy-7-(4-benzamide)-2-oxo-2,3-dihydro-1H-benzo[e][1,4]diazepin-5-yl]-benzamide Prepared from 3-(8-Methoxy-1-methyl-2-oxo-7-(4-cyanophenyl)-2,3-dihydro-1H-benzo[e][1,4]diazepin-5-yl)-benzonitrile Example 43 using the same method described for Example 19. The title compound (13 mg) was obtained as a white solid, yield=80%.
$^1$H NMR (DMSO-d6, 200 MHz): δ 8.11-7.37 (m, 12H), 7.26 (s, 1H), 7.15 (s, 1H), 4.67-4.61 and 3.92-3.86 (AB system, J=12 Hz), 3.97 (s, 3H), 3.45 (s, 3H).

Example 36

3-[8-Methoxy-7-(2-methoxy-phenyl)-2-oxo-2,3-dihydro-1H-benzo[e][1,4]diazepin-5-yl]-benzamide Prepared from 3-[8-methoxy-7-(2-methoxy-phenyl)-2-oxo-2,3-dihydro-1H-benzo[e][1,4]diazepin-5-yl]-benzonitrile Example 10 using the same method described for Example 19. The title compound (45 mg) was obtained as a pale yellow solid, yield=85%.
$^1$H NMR (CDCl₃, 300 MHz): δ 8.25 (s-broad, 1H), 8.06 (m, 1H), 7.97-7.94 (m, 1H), 7.78-7.75 (m, 1H), 7.51-7.46 (m, 1H), 7.32-7.29 (m, 1H), 7.19-7.17 (m, 2H), 6.99-6.93 (m, 2H), 6.63 (s, 1H), 6.24 and 5.69 (2 s-broad, 2H), 4.41 (s-broad, 2H), 3.85 (s, 3H), 3.74 (s, 3H).

Example 44

3-[1-Benzyl-8-methoxy-7-(2-methoxy-phenyl)-2-oxo-2,3-dihydro-1H-benzo[e][1,4]diazepin-5-yl]-benzamide Prepared from 3-[1-Benzyl-8-methoxy-7-(2-methoxy-phenyl)-2-oxo-2,3-dihydro-1H-benzo[e][1,4]diazepin-5-yl]-benzonitrile Example 39 using the same method described for Example 19. The title compound (23 mg) was obtained as a white solid, yield=23%.
$^1$H NMR (CDCl₃, 200 MHz): δ 8.00-7.93 (m, 2H), 7.69-7.65 (m, 1H), 7.50-7.43 (m, 1H), 7.32-7.29 (m, 1H), 7.22 (m, 5H), 7.17-7.09 (m, 2H), 6.98-6.94 (m, 2H), 6.89 (s, 1H), 6.11 and 5.55 (2 s-broad, 2H), 5.38-5.31 and 5.14-5.07 (AB system, J=16 Hz, 2H), 4.96-4.90 and 4.08-4.09 (AB system, J=10 Hz, 2H), 3.69 (s, 6H).

Example 45

3-[8-Methoxy-7-(2-methoxy-phenyl)-2-oxo-1-propyl-2,3-dihydro-1H-benzo[e][1,4]diazepin-5-yl]-benzamide Prepared from 3-[8-Methoxy-7-(2-methoxy-phenyl)-2-oxo-1-propyl-2,3-dihydro-1H-benzo[e][1,4]diazepin-5-yl]-benzonitrile using the same method described for Example 37. The title compound (62 mg) was obtained as a white solid, yield=82%.

$^1$H NMR (CDCl$_3$, 300 MHz): δ 8.15 (s, 1H), 7.98-7.94 (m, 2H), 7.78-7.76 (m, 1H), 7.51-7.46 (m, 1H), 7.35-7.30 (m, 1H), 7.23-7.20 (m, 1H), 7.16 (s, 1H), 7.00-6.92 (m, 3H), 6.21 and 5.62 (2 s-broad, 2H), 4.83-4.79 and 3.94-3.91 (AB system, J=10 Hz, 2H), 3.88 (s, 3H), 3.76 (s, 3H), 4.38-4.28 and 3.73-3.63 (AB system, 2H), 1.72-1.64 (m, 2H), 0.86-0.81 (s, 3H).

Example 46

3-[8-Methoxy-7-(2-methoxy-phenyl)-2-oxo-1-phenethyl-2,3-dihydro-1H-benzo[e][1,4]diazepin-5-yl]-benzamide Prepared from 3-[8-methoxy-7-(2-methoxy-phenyl)-2-oxo-1-phenethyl-2,3-dihydro-1H-benzo[e][1,4]diazepin-5-yl]-benzonitrile using the same method described for Example 38. The title compound (58 mg) was obtained as a white solid, yield=52%.

$^1$H NMR (CDCl$_3$, 300 MHz): δ 8.10 (m, 1H), 8.00-7.95 (m, 1H), 7.73-7.71 (m, 1H), 7.50-7.44 (m, 1H), 7.34-7.29 (m, 1H), 7.19-7.14 (m, 7H), 7.00-6.93 (m, 2H), 6.79 (s, 1H), 6.17 and 5.61 (2 s-broad, 2H), 4.52-4.43 and 4.08-3.98 (AB system, 2H), 4.85-4.81 and 3.94-3.91 (AB system, J=11 Hz, 2H), 3.79 (s, 3H), 3.75 (s, 3H), 3.05-3.00 (t, 2H).

Example 47

3-[1-Hexyl-8-methoxy-7-(2-methoxy-phenyl)-2-oxo-2,3-dihydro-1H-benzo[e][1,4]diazepin-5-yl]-benzamide Prepared from 3-[1-Hexyl-8-methoxy-7-(2-methoxy-phenyl)-2-oxo-2,3-dihydro-1H-benzo[e][1,4]diazepin-5-yl]-benzonitrile using the same method described for Example 35. The title compound (37 mg) was obtained as a white solid, yield=59%.

$^1$H NMR (CDCl$_3$, 200 MHz): δ 8.16 (m, 1H), 8.98-7.94 (m, 1H), 7.79-7.75 (m, 1H), 7.52-7.44 (m, 1H), 7.36-7.28 (m, 1H), 7.25-7.20 (m, 1H), 7.17 (s, 1H), 7.01-6.93 (m, 3H), 6.23 and 5.62 (2 s-broad, 2H), 4.83-4.78 and 3.95-3.90 (AB system, J=10 Hz), 3.88 (s, 3H), 3.76 (s, 3H), 4.43-4.28 and 3.81-3.64 (AB system, 2H), 1.62 (m 2H), 1.29-1.18 (m, 6H), 0.81-0.76 (s, 3H).

Example 49

3-[7-(4-Acetylphenyl)-8-methoxy-1-methyl-2-oxo-2,3-dihydro-1H-benzo[e][1,4]diazepin-5-yl]-benzamide Prepared from 3-[7-(4-acetylphenyl)-8-methoxy-1-methyl-2-oxo-2,3-dihydro-1H-benzo[e][1,4]diazepin-5-yl]-benzonitrile Example 48 using the same method described for Example 35. The title compound (24 mg) was obtained as a white solid, yield=38%.

TLC: (CH$_2$Cl$_2$/MeOH: 9/1): Rf: 0.4 $^1$H NMR (CDCl$_3$, 300 MHz): δ 8.15 (m, 1H), 7.98-7.90 (m, 3H), 7.83-7.81 (m, 1H), 7.55-7.47 (m, 3H), 7.04 (s, 1H), 6.89 (s, 1H), 6.23 and 5.67 (2 s-broad, 2H), 4.89-4.85 and 3.91-3.88 (AB system, J=10 Hz), 3.95 (s, 3H), 3.50 (s, 3H), 2.61 (s, 3H).

Example 54

3-[7-(3,4-Dimethoxy-phenyl)-1-methyl-2-oxo-2,3-dihydro-1H-benzo[e][1,4]diazepin-5-yl]-benzamide Prepared from 3-[7-(3,4-dimethoxy-phenyl)-1-methyl-2-oxo-2,3-dihydro-1H-benzo[e][1,4]diazepin-5-yl]-benzonitrile Example 53 using the same conditions used to prepare Example 19. The title compound (45 mg) was obtained as a yellow solid, yield=86%.

1H NMR (CDCl$_3$, 300 MHz): δ 8.20 (m, 1H), 7.95-7.93 (m, 1H), 7.82-7.74 (m, 2H), 7.54-7.40 (m, 3H), 6.93-6.91 (m, 3H), 6.27 and 5.76 (2 large s, 2H), 4.88-4.84 and 3.90-3.86 (AB system, J=11 Hz, 2H), 3.90 (s, 6H), 3.46 (s, 3H).

Example 72

3-(1-Methyl-2-oxo-8-phenoxy-7-phenyl-2,3-dihydro-1H-benzo[e][1,4]diazepin-5-yl)-benzamide Prepared from 3-(1-Methyl-2-oxo-8-phenoxy-7-phenyl-2,3-dihydro-1H-benzo[e][1,4]diazepin-5-yl)-benzonitrile Example 69 using the same method described for Example 35. The title compound (35 mg) was obtained as a yellow solid, yield=67%.

$^1$H NMR (CDCl$_3$, 300 MHz): δ 8.19 (s, 1H), 7.95-7.92 (m, 1H), 7.83-7.81 (m, 1H), 7.53-7.49 (m, 3H), 7.41-7.33 (m, 6H), 7.21-7.19 (m, 1H), 7.10-7.07 (m, 2H), 6.81 (s, 1H), 6.31 and 5.83 (2 large s, 2H), 4.86-4.83 and 3.92-3.89 (AB system, J=10 Hz, 2H), 3.26 (s, 3H).

Example 73

3-[7-(2-Chloro-phenyl)-1-methyl-2-oxo-8-phenoxy-2,3-dihydro-1H-benzo[e][1,4]diazepin-5-yl]-benzamide Prepared from 3-[7-(2-chloro-phenyl)-1-methyl-2-oxo-8-phenoxy-2,3-dihydro-1H-benzo[e][1,4]diazepin-5-yl]-benzonitrile Example 71 using the same method described for Example 35. The title compound (35 mg) was obtained as a yellow solid, yield=67%.

$^1$H NMR (CDCl$_3$, 300 MHz): δ 8.18 (s, 1), 7.97-7.84 (m, 2H), 7.52-7.49 (m, 1H), 7.40-7.23 (m, 5H), 7.18-7.06 (m, 3H), 6.97-6.88 (m, 2H), 6.80 (s, 1H), 6.33 and 5.82 (2 large s, 2H), 4.85-4.82 and 3.96-3.92 (AB system, J=10 Hz, 2H), 3.71 (s, 3H), 3.27 (s, 3H).

Example 74

3-[7-(2-Methoxy-phenyl)-1-methyl-2-oxo-8-phenoxy-2,3-dihydro-1H-benzo[e][1,4]diazepin-5-yl]-benzamide Prepared from 3-[7-(2-methoxy-phenyl)-1-methyl-2-oxo-8-phenoxy-2,3-dihydro-1H-benzo[e][1,4]diazepin-5-yl]-benzonitrile Example 70 using the same method described for Example 35. The title compound (60 mg) was obtained as a yellow solid, yield=83%.

$^1$H NMR (CDCl$_3$, 300 MHz): δ 8.14 (s, 1H), 7.95-7.87 (m, 2H), 7.53-7.50 (m, 1H), 7.43-7.20 (m, 4H), 7.27-7.17 (m,

4H), 7.09-7.06 (m, 2H), 6.78 (s, 1H), 6.25 and 5.77 (2 large s, 2H), 4.87-4.84 and 3.94-3.91 (AB system, J=10 Hz, 2H), 3.27 (s, 3H).

Example 78

3-[7-(2-Isopropoxy-phenyl)-8-methoxy-1-methyl-2-oxo-2,3-dihydro-1H-benzo[e][1,4]diazepin-5-yl]-benzamide Prepared from 3-[7-(2-isopropoxy-phenyl)-8-methoxy-1-methyl-2-oxo-2,3-dihydro-1H-benzo[e][1,4]diazepin-5-yl]-benzonitrile Example 63 using the same method described for Example 35. The title compound (89 mg) was obtained as a white solid, yield=69%.

$^1$H NMR (CDCl$_3$, 200 MHz): δ 8.12 (m, 1H), 7.95-7.91 (m, 1H), 7.81-7.77 (m, 1H), 7.51-7.44 (m, 1H), 7.33-7.29 (m, 1H), 7.17-7.12 (m, 2H), 6.98-6.91 (m, 2H), 6.84 (s, 1H), 6.09 and 5.62 (2 s-broad, 2H), 4.87-4.82 and 3.94-3.89 (AB system, J=11 Hz), 4.50-4.41 (sept, 1H), 3.88 (s, 3H), 3.51 (s, 3H), 1.20-1.17 (m, 6H).

Example 83

3-[7-(5-Chloro,2-methoxy-phenyl)-1-methyl-2-oxo-2,3-dihydro-1H-benzo[e][1,4]diazepin-5-yl]-benzamide Prepared from 3-[7-(5-chloro,2-methoxy-phenyl)-1-methyl-2-oxo-2,3-dihydro-1H-benzo[e][1,4]diazepin-5-yl]-benzonitrile Example 81 using the same conditions used to prepare Example 19. The title compound (37 mg) was obtained as a yellow solid, yield=79%.

1H NMR (CDCl$_3$, 300 MHz): δ 8.18 (m, 1H), 7.99-7.97 (m, 1H), 7.85-7.83 (m, 1H), 7.73-7.69 (m, 1H), 7.52-7.41 (m, 3H), 7.29-7.23 (m, 2H), 6.90-6.87 (m, 1H), 6.26 and 5.59 (2 large s, 2H), 4.89-4.85 and 3.91-3.8 (AB system, J=11 Hz, 2H), 3.76 (s, 3H), 3.48 (s, 3H).

Example 84

3-[7-(2-Chloro,6-methoxy-phenyl)-1-methyl-2-oxo-2,3-dihydro-1H-benzo[e][1,4]diazepin-5-yl]-benzamide Prepared from 3-[7-(2-chloro,6-methoxy-phenyl)-1-methyl-2-oxo-2,3-dihydro-1H-benzo[e][1,4]diazepin-5-yl]-benzonitrile Example 82 using the same conditions used to prepare Example 19. The title compound (48 mg) was obtained as a beige solid, yield=77%.

1H NMR (CDCl$_3$, 300 MHz): δ 8.12 (m, 1H), 7.97-7.95 (m, 1H), 7.89-7.87 (m, 1H), 7.52-7.42 (m, 2H), 7.28-7.23 (m, 3H), 7.09-7.06 (m, 1H), 6.88-6.85 (m, 1H), 6.31 and 5.61 (2 large s, 2H), 4.90-4.86 and 3.98-3.94 (AB system, J=11 Hz, 2H), 3.74 (s, 3H), 3.49 (s, 3H).

Example 87

3-(1-Methyl-2-oxo-7-phenyl-8-trifluoromethoxy-2,3-dihydro-1H-benzo[e][1,4]diazepin-5-yl)-benzamide Prepared from 3-(1-methyl-2-oxo-7-phenyl-8-trifluoromethoxy-2,3-dihydro-1H-benzo[e][1,4]diazepin-5-yl)-benzonitrile Example 86 using the same conditions used to prepare Example 19. The title compound (35 mg) was obtained as a white solid, yield=61%.

1H NMR (CDCl$_3$, 300 MHz): δ 8.15 (s, 1H), 7.94-7.92 (m, 1H), 7.80-7.82 (m, 1H), 7.53-7.48 (m, 1H), 7.41-7.32 (m, 7H), 6.23 and 5.74 (2 large s, 2H), 4.93-4.89 and 3.92-3.89 (AB system, J=11 Hz, 2H), 3.47 (s, 3H).

Example 91

3-[1-Methyl-2-oxo-7-(2-phenoxy-phenyl)-2,3-dihydro-1H-benzo[e][1,4]diazepin-5-yl]-benzamide Prepared from 3-[1-methyl-2-oxo-7-(2-phenoxy-phenyl)-2,3-dihydro-1H-benzo[e][1,4]diazepin-5-yl]-benzonitrile Example 88 using the same conditions used to prepare Example 19. The title compound (40 mg) was obtained as a beige solid, yield=77%.

1H NMR (CDCl$_3$, 400 MHz): δ 8.05 (s, 1H), 7.92-7.90 (m, 1H), 7.78-7.76 (m, 1H), 7.65-7.63 (m, 1H), 7.49-7.20 (m, 7H), 7.18-7.06 (m, 1H), 6.95-6.93 (m, 2H), 7.85-6.82 (m, 2H), 6.23 and 5.74 (2 large s, 2H), 4.93-4.89 and 3.92-3.89 (AB system, J=11 Hz, 2H), 3.47 (s, 3H).

Example 92

3-[7-(2,6-Dimethoxy-phenyl)-8-methoxy-1-methyl-2-oxo-2,3-dihydro-1H-benzo[e][1,4]diazepin-5-yl]-benzamide Prepared from 3-[7-(2,6-dimethoxy-phenyl)-8-methoxy-1-methyl-2-oxo-2,3-dihydro-1H-benzo[e][1,4]diazepin-5-yl]-benzonitrile Example 89 using the same conditions used to prepare Example 19. The title compound (40 mg) was obtained as a beige solid, yield=65%.

1H NMR (CDCl$_3$, 400 MHz): δ 8.07 (s, 1H), 7.88-7.86 (m, 1H), 7.78-7.76 (m, 1H), 7.41-7.39 (m, 1H), 7.25-7.22 (m, 1H), 7.02 (s, 1H), 6.78 (s, 1H), 6.56-6.51 (m, 2H), 6.24 and 5.35 (2 large s, 2H), 4.76-4.73 and 3.91-3.89 (AB system, J=11 Hz, 2H), 3.79 (s, 3H), 3.69 (s, 3H), 6.61 (s, 3H), 3.42 (s, 3H).

Example 93

3-[8-Methoxy-1-methyl-2-oxo-7-(2-phenoxy-phenyl)-2,3-dihydro-1H-benzo[e][1,4]diazepin-5-yl]-benzamide Prepared from 3-[8-Methoxy-1-methyl-2-oxo-7-(2-phenoxy-phenyl)-2,3-dihydro-1H-benzo[e][1,4]diazepin-5-yl]-benzonitrile Example 90 using the same conditions used to prepare Example 19. The title compound (70 mg) was obtained as a beige solid, yield=90%.

1H NMR (CDCl$_3$, 400 MHz): δ 8.02 (s, 1H), 7.85-7.83 (m, 1H), 7.59-7.57 (m, 1H), 7.28-7.18 (m, 5H), 7.09-7.05 (m, 2H), 6.98-6.95 (m, 1H), 6.87-6.85 (m, 1H), 6.80-6.78 (m, 2H), 6.69 (s, 1H), 6.18 and 5.62 (2 large s, 2H), 4.75-4.72 and 3.78-3.75 (AB system, J=11 Hz, 2H), 3.71 (s, 3H), 3.37 (s, 3H).

Preparation of Examples of General Formula I
(Scheme 9)

Example 66

5-(3-Hex-1-ynyl-phenyl)-8-methoxy-1-methyl-7-phenyl-1,3-dihydro-benzo[e][1,4]diazepin-2-one To 10 mL of degazed acetonitrile, 5-(3-bromo-phenyl)-8-methoxy-1-methyl-7-phenyl-1,3-dihydro-benzo[e][1,4]diazepin-2-one Example 62 (200 mg, 0.46 mmol), phenylacetylene (715 μL, 2.30 mmol), copper iodide (15 mg, 0.08 mmol), triphenylphosphine (30 mg, 0.11 mmol), PdCl$_2$ (10 mg, 0.06 mmol) and triethylamine (0.9 mL) were added. The mixture was stirred for 16 hours at 50° C. under nitrogen atmosphere. The working solution was evaporated under vacuum. The residue was partitioned from water and ethyl acetate and extracted two more times with ethyl acetate. The organic phase was dried over Na$_2$SO$_4$ and concentrated until dryness. The residue was purified by chromatography (eluant: Hexane/EtOAc: 1/1). The title compound was crystallised from ether/pentane to afford 134 mg of the title compound: beige solid, yield=90%.

1H NMR (CDCl3, 200 MHz): δ 7.67-7.21 (m, 10H), 6.84 (s, 1H), 4.85-4.80 and 3.92-3.88 (AB system, J=10.5 Hz, 2H), 3.92 (s, 3H), 3.47 (s, 3H), 2.38-2.34 (m, 2H), 1.60-1.42 (m, 4H), 0.96-0.89 (m, 3H).

Prepared from 3-[8-methoxy-7-(2-methoxy-phenyl)-2-oxo-2,3-dihydro-1H-benzo[e][1,4]diazepin-5-yl]-benzonitrile Example 10 using the same method described for Example 35 using benzyl bromide instead of hexyl bromide. The title compound (95 mg) was obtained as a yellow solid, (yield=90%).

Example 67

{3-[3-(8-Methoxy-1-methyl-2-oxo-7-phenyl-2,3-dihydro-1H-benzo[e][1,4]diazepin-5-yl)-phenyl]-prop-2-ynyl}-carbamic acid tert-butyl ester Prepared from 5-(3-bromo-phenyl)-8-methoxy-1-methyl-7-phenyl-1,3-dihydro-benzo[e][1,4]diazepin-2-one Example 62 using the same method described for Example 35 using propargyl Boc-amine instead of hex-1-yne. The title compound (51 mg) was obtained as a beige solid, (yield=22%).

TLC: (Hexane/AcOEt: 1/1): Rf: 0.17 1H NMR (CDCl3, 300 MHz): δ 7.69-7.28 (m, 9H), 7.20 (s, 1H), 6.86 (s, 1H), 4.86-4.82 and 3.89-3.868 (AB system, J=10.5 Hz, 2H), 4.82 (broad s, 1H), 4.14-4.13 (m, 2H), 3.94 (s, 3H), 3.49 (s, 3H), 1.47 (s, 9H).

Example 94

8-Methoxy-1-methyl-7-phenyl-5-[3-(4-phenyl-butyl)-phenyl]-1,3-dihydro-benzo[e][1,4]diazepin-2-one Prepared from 8-Methoxy-1-methyl-7-phenyl-5-[3-(4-phenyl-but-1-ynyl)-phenyl]-1,3-dihydro-benzo[e][1,4]diazepin-2-one The title compound (5 mg) was obtained as a beige solid, (yield=14%).

TLC: (H/AcOEt: 1/1): Rf: 0.3 1H NMR (CDCl3, 300 MHz): δ 7.54-7.13 (m, 15H), 6.85 (s, 1H), 4.85-4.81 and 3.89-3.86 (AB system, J=10.5 Hz, 2H), 3.93 (s, 3H), 3.48 (s, 3H), 2.65-2.60 (m, 4H), 1.67-1.55 (m, 4H).

Example 95

8-Methoxy-5-[3-(3-methoxy-prop-1-ynyl)-phenyl]-1-methyl-7-phenyl-1,3-dihydro-benzo[e][1,4]diazepin-2-one Prepared from 5-(3-Bromo-phenyl)-8-methoxy-1-methyl-7-phenyl-1,3-dihydro-benzo[e][1,4]diazepin-2-one The title compound (129 mg) was obtained as a beige solid, (yield=66%).

TLC: (H/AcOEt: 1/1): Rf: 0.2 1H NMR (CDCl3, 300 MHz): δ 7.75-7.72 (board s, 1H), 7.64-7.61 (m, 1H), 7.53-7.50 (m, 1H), 7.45-7.30 (m, 6H), 7.20 (s, 1H), 6.86 (s, 1H), 4.85-4.82 and 3.89-3.86 (AB system, J=10.5 Hz, 2H), 4.30 (s, 2H), 3.93 (s, 3H), 3.48 (s, 3H), 3.43 (s, 3H).

Example 96

{3-[4-(8-Methoxy-1-methyl-2-oxo-7-phenyl-2,3-dihydro-1H-benzo[e][1,4]diazepin-5-yl)-phenyl]-prop-2-ynyl}-carbamic acid tert-butyl ester Prepared from 5-(4-Bromo-phenyl)-8-methoxy-1-methyl-7-phenyl-1,3-dihydro-benzo[e][1,4]diazepin-2-one The title compound (127 mg) was obtained as a beige solid, (yield=75%).

TLC: (H/AcOEt: 1/1): Rf: 0.2 1H NMR (CDCl3, 300 MHz): δ 7.63-7.60 (m, 2H), 7.44-7.33 (m, 7H), 7.20 (s, 1H), 6.85 (s, 1H), 4.86-4.82 and 3.89-3.86 (AB system, J=10.5 Hz, 2H), 4.80 (board s, 1H), 4.17 (board s, 2H), 3.93 (s, 3H), 3.48 (s, 3H), 1.47 (s, 9H).

Example 97

8-Methoxy-1-methyl-7-phenyl-5-(4-phenylethynyl-phenyl)-1,3-dihydro-benzo[e][1,4]diazepin-2-one Prepared from 5-(4-Bromo-phenyl)-8-methoxy-1-methyl-7-phenyl-1,3-dihydro-benzo[e][1,4]diazepin-2-one The title compound (128 mg) was obtained as a brown solid, (yield=82%).

TLC: (H/AcOEt: 1/1): Rf: 0.3 1H NMR (CDCl3, 300 MHz): δ 7.70-7.53 (m, 6H), 7.46-7.35 (m, 9H), 7.24 (s, 1H), 6.86 (s, 1H), 4.87-4.84 and 3.91-3.88 (AB system, J=10.5 Hz, 2H), 3.93 (s, 3H), 3.49 (s, 3H).

Example 98

8-Methoxy-5-[4-(3-methoxy-prop-1-ynyl)-phenyl]-1-methyl-7-phenyl-1,3-dihydro-benzo[e][1,4]diazepin-2-one Prepared from 5-(4-Bromo-phenyl)-8-methoxy-1-methyl-7-phenyl-1,3-dihydro-benzo[e][1,4]diazepin-2-one The title compound (20 mg) was obtained as a brown solid, (yield=14%).

TLC: (H/AcOEt: 1/1): Rf: 0.3 1H NMR (CDCl3, 300 MHz): δ 7.63-7.60 (m, 2H), 7.48-7.36 (m, 7H), 7.21 (s, 1H), 6.85 (s, 1H), 4.86-4.82 and 3.89-3.86 (AB system, J=10.5 Hz, 2H), 4.33 (s, 2H), 3.92 (s, 3H), 3.48 (s, 3H).

Example 103

8-Methoxy-5-[3-(3-methoxy-propyl)-phenyl]-1-methyl-7-phenyl-1,3-dihydro-benzo[e][1,4]diazepin-2-one Prepared from 5-(3-Bromo-phenyl)-8-methoxy-1-methyl-7-phenyl-1,3-dihydro-benzo[e][1,4]diazepin-2-one The title compound (60 mg) was obtained as a white solid, (yield=50%).

TLC: (H/AcOEt: 1/1): Rf: 0.2 1H NMR (CDCl3, 300 MHz): δ 7.52 (s, 1H), 7.44-7.24 (m, 9H), 6.85 (s, 1H), 4.84-

4.81 and 3.89-3.86 (AB system, J=10.5 Hz, 2H), 3.93 (s, 3H), 3.48 (s, 3H), 3.39-3.35 (m, 2H), 3.30 (s, 3H), 2.73-2.68 (m, 2H), 1.91-1.86 (m, 2H).

Example 105

5-(4-Hex-1-ynyl-phenyl)-8-methoxy-1-methyl-7-phenyl-1,3-dihydro-benzo[e][1,4]diazepin-2-one Prepared from 5-(4-Bromo-phenyl)-8-methoxy-1-methyl-7-phenyl-1,3-dihydro-benzo[e][1,4]diazepin-2-one The title compound (104 mg) was obtained as a white solid, (yield=70%).

TLC: (H/AcOEt: 1/1): Rf: 0.3 1H NMR (CDCl3, 200 MHz): δ 7.60-7.46 (m, 2H), 7.42-7.21 (m, 8H), 6.84 (s, 1H), 4.85-4.80 and 3.87-3.83 (AB system, J=10.5 Hz, 2H), 3.92 (s, 3H), 3.47 (s, 3H), 2.51-2.38 (m, 2H), 1.57-1.43 (m, 4H), 1.04-0.91 (m, 3H).

Example 106

8-Methoxy-5-[4-(3-methoxy-propyl)-phenyl]-1-methyl-7-phenyl-1,3-dihydro-benzo[e][1,4]diazepin-2-one Prepared from 8-Methoxy-5-[4-(3-methoxy-prop-1-ynyl)-phenyl]-1-methyl-7-phenyl-1,3-dihydro-benzo[e][1,4]diazepin-2-one The title compound (7 mg) was obtained as a white solid, (yield=44%).

TLC: (H/AcOEt: 1/1): Rf: 0.2 1H NMR (CDCl3, 300 MHz): δ 7.60-7.46 (m, 2H), 7.44-7.20 (m, 8H), 6.85 (s, 1H), 4.84-4.80 and 3.89-3.86 (AB system, J=10.5 Hz, 2H), 3.93 (s, 3H), 3.53 (s, 3H), 3.40-3.34 (m, 6H), 2.75-2.70 (m, 2H), 1.95-1.87 (m, 2H).

Example 107

{3-[4-(8-Methoxy-1-methyl-2-oxo-7-phenyl-2,3-dihydro-1H-benzo[e][1,4]diazepin-5-yl)-phenyl]-propyl}-carbamic acid tert-butyl ester Prepared from {3-[4-(8-Methoxy-1-methyl-2-oxo-7-phenyl-2,3-dihydro-1H-benzo[e][1,4]diazepin-5-yl)-phenyl]-prop-2-ynyl}-carbamic acid tert-butyl ester The title compound (6 mg) was obtained as a beige solid, (yield=50%).

TLC: (H/AcOEt: 1/1): Rf: 0.2 1H NMR (CDCl3, 200 MHz): δ 7.59-7.55 (m, 2H), 7.42-7.16 (m, 8H), 6.84 (s, 1H), 4.83-4.77 and 3.89-3.83 (AB system, J=10.5 Hz, 2H), 3.91 (s, 3H), 3.46 (s, 3H), 3.16-3.13 (m, 2H), 2.70-2.62 (m, 2H), 1.84-1.77 (m, 2H).

Example B

Pharmacological Activity: Inhibition of Phosphodiesterases

Isolation of Phosphodiesterases from Smooth Muscle 3 g of tunica media from bovine aorta was cut in small piece and homogenized in a glass potter with 7 volumes/weight of buffer A containing protease inhibitors cocktails (20 mM Tris-HCl, 0.25 M saccharose, 2 mM magnesium acetate, 1 mM dithiothreitol, 5 mM EGTA, 2000 U/ml aprotinine, 10 mg/l leupeptine, 10 mg/l of soybean chemotrypsin inhibitor). The homogenate was centrifuged at 875000 g for 1 h and the surpernant was then transferred in DEAE-Sephacel (15×1.6 cm). The column was equilibrated beforehand with a buffer B (buffer A without saccharose, d'EGTA and protease inhibitors). The column was washed until no absorption was detected at 280 nm and then eluated with linear gradient of NaCl (0-0.5 M) in the buffer B. Fractions of 3 ml volume were collected and the enzymatic activities were assessed under the conditions described below in order to identify fractions containing PDE1, PDE3, PDE4 and PDE5 (Lugnier et al., Biochem. Phamacol., 35 (1986) 1746-1751). Fractions were aliquoted and stored at −80° C. until further use. PDE2 was prepared from bovine endothelial cells using the same procedure (Lugnier and Schini, Biochem. Pharmacol. 1990, 39; 75-84).

Protocol for the Measurement of Phosphodiesterase Activities

Cyclic nucleotide phosphodiesterase activity was determined by radioenzymatic assay using tritiated cyclic AMP or GMP (1 µM) as a substrate (Lugnier et el., 1986). The monophosphated adenosine or guanosine released by the hydrolysis of tritiated cyclic nucleotides was transformed into tritiated adenosine or guanosine by excess of nucleotidase. The obtained nucleoside was separated from nucleotides by anion exchange chromatography. Nucleoside radioactivity was determined by liquid scintillation. All enzymatic reactions were conducted in duplicates and under conditions to obtain less than 15% of substrate hydrolysis.

Measurement of PDE2 Inhibition.

The concentration of substance required to inhibit 50% of the enzymatic activity ($IC_{50}$) in the presence of 1 µM cyclic AMP was determined by non-linear regression analysis of the rate of hydrolysis (Prism, GraphPad).

Selectivity

The phosphodiesterase inhibitory activity of compounds was evaluated on other isoforms of phosphodiesterases such as PDE3, and PDE4 of vascular smooth muscle.

Obtained results were presented in Tables 1 and 2, showing the percentage of PDE inhibition by 10 µM of test compound or the inhibitory concentration at which the enzymatic activity is reduced by 50% (IC50).

TABLE 1

Inhibitory activity of representative compounds of formula (I) on PDE2.

| Examples | PDE2 percentage of inhibition at 10 µM or [$IC_{50}$ (µM)] |
|---|---|
| 1 | 83% [0.57] |
| 2 | 97% [0.6] |
| 3 | 100% |
| 4 | 97% [0.3] |
| 5 | 98% |
| 6 | 96% [1.4] |
| 7 | 91% [1.2] |
| 8 | 47% |
| 9 | 84% |
| 10 | 94% |
| 11 | 79% [2.2] |
| 12 | 40% |
| 13 | 91% |
| 14 | 92% |
| 15 | 98% |
| 16 | 100% [0.6] |
| 17 | 98% |
| 18 | 27% |
| 19 | 97% [0.05] |
| 20 | 99% [0.2] |

TABLE 1-continued

Inhibitory activity of representative compounds of formula (I) on PDE2.

| Examples | PDE2 percentage of inhibition at 10 μM or [IC$_{50}$ (μM)] |
|---|---|
| 21 | 98% [0.04] |
| 22 | 99% [0.026] |
| 23 | 95% [0.06] |
| 24 | 98% [0.1] |
| 25 | 97% [0.12] |
| 26 | 71% |
| 27 | 96% [1.1] |
| 28 | 97% |
| 29 | 95% |
| 30 | 95% |
| 31 | 99% [0.1] |
| 32 | 100% [0.03] |
| 33 | 99% |
| 34 | 98% |
| 35 | 39% |
| 36 | 94% [0.5] |
| 37 | 45% |
| 38 | 86% [4.0] |
| 39 | 72% |
| 40 | 68% |
| 41 | 34% |
| 42 | 1% |
| 43 | 92% |
| 44 | 88% |
| 45 | 48% |
| 46 | 78% |
| 47 | 59% |
| 48 | 97% |
| 49 | 99% |
| 50 | 95% [0.3] |
| 51 | 28% |
| 52 | 78% |
| 53 | 95% |
| 54 | 94% |
| 55 | 53% |
| 56 | 70% |
| 57 | 74% |
| 58 | 91% |
| 59 | 43% |
| 60 | 88% |
| 61 | 31% |
| 62 | 98% |
| 63 | 98% |
| 64 | 79% |
| 65 | 78% |
| 66 | 86% |
| 67 | 60% |
| 68 | 52% |
| 69 | 4% |
| 70 | 95% |
| 71 | 82% |
| 72 | 28% |
| 73 | 96% |
| 74 | 98% [0.3] |
| 75 | 99% [0.017] |
| 76 | 91% |
| 77 | 99% |
| 78 | 97% |
| 79 | 84% |
| 80 | — |
| 81 | 22% |
| 82 | 92% |
| 83 | 96% [0.02] |
| 84 | 98% [0.2] |
| 85 | 70% |
| 86 | 85% |
| 87 | 93% [0.8] |
| 88 | 89% |
| 89 | 99% |
| 90 | 98% |
| 91 | 96% [0.2] |
| 92 | 97% [0.02] |
| 93 | 98% [0.03] |
| 94 | 79% |
| 95 | 89% |
| 96 | 21% |
| 97 | 45% |
| 98 | 80% |
| 99 | 98% |
| 100 | 96% [0.1] |
| 101 | 99% |
| 102 | 48% |
| 103 | 96% [0.3] |
| 104 | 71% |
| 105 | 42% |
| 106 | 47% |
| 107 | 92% |
| 108 | 99% |
| 109 | 99% [0.006] |
| 110 | 99% |
| 111 | 99% |
| 112 | 99% |
| 113 | 94% |
| 114 | 72% |
| 115 | 96% [0.5] |

TABLE 2

Inhibitory activity of selected compounds of formula (I) on PDE2, PDE3 and PDE4

| | IC$_{50}$ (μM) or percentage Of inhibition at 10 μM | | |
|---|---|---|---|
| Examples | PDE2 | PDE3 | PDE4 |
| 19 | 97% [0.05] | 23% | 14% |
| 21 | 98% [0.04] | 9% | 18% |
| 22 | 99% [0.026] | 22% | 50% |
| 23 | 95% [0.06] | 25% | 20% |
| 31 | 99% [0.1] | 0% | 25% |
| 32 | 100% [0.03] | 0% | 27% |
| 75 | 99% [0.017] | 4% | 78% |
| 83 | 96% [0.02] | 34% | 43% |
| 92 | 97% [0.02] | 52% | 23% |
| 93 | 98% [0.03] | 72% | 56% |
| 100 | 96% [0.1] | 0% | 77% |
| 109 | 99% [0.006] | 37% | 90% [1] |
| 115 | 96% [0.5] | 3% | 42% |

Overall, most of tested compounds showed a marked inhibitory activity on PDE2. Preferred molecules showed a good profile of potency and selectivity towards PDE2, as these compounds show a very weak inhibitory activity on the other PDE isoforms, especially on the PDE3.

Example C

Behavioural Tests

Swim Test

This test is based on the induction of alternative behaviour in rodents subjected to an acute stress. In this model, the rat or mouse placed in a container filled with water show periods of increased swimming activity and periods of relative immobility. Clinically active anti-depressants have been found to delay the onset of the first phase of immobility and to reduce the total time of relative immobility.

Swiss mice were used. The animal was placed individually in the water where it remained for 6 minutes. The animal was given an accommodation period of 2 minutes. During the last 4 minutes observation period, the onset of the first period of immobility and the duration of the periods of immobility were recorded.

Treatment was administered 16 minutes prior to the test. Animals were randomly distributed in 4 groups. Control group received the vehicle whereas the other 3 groups received different single dose of test compound.

Results are illustrated in FIG. 1: Mean Duration of Phases of Immobility (s); N=10; p<0.005 (Dunnett's test).

Statistical analyses revealed a significant difference between groups regarding the period of total immobility (p=0.005). Mice treated with 0.3, 3 or 30 mg/kg of test compound showed significantly shorter time of relative immobility than control animals.

Light Dark Test

1. Purpose

The light dark (LD) test is used to evaluate the relative anxiety status of mice.

2. Background

The light dark paradigm in rodents is based on a conflict between the innate aversion to brightly illuminated areas and the spontaneous exploratory activity. If given a choice between a large brightly compartment versus a small dark compartment, animals spontaneously prefer the dark. Anxiolytic compounds have been found to increase the number of entries into the bright compartment and the total duration of time spent there. Anxiogenic compounds were observed to work in the opposite way.

3. Materials

Equipment

The apparatus consists of two polyvinylchloride boxes (19×19×15 cm) closed with plexiglas. One of these boxes is illuminated by a 100 W desk lamp placed 15 cm above and providing an illumination of about 4400 Lux, the other box being dark. An opaque plastic tunnel (5×7×10 cm) separates the dark box from the illuminated one.

Reagents

Test substance

Vehicle

4. Methods

Step 1—drug treatments:

Animals are randomly assigned to test compounds of the invention (test substances) and control groups. Each animal is treated with vehicle or test compounds one hour before the test at appropriate doses and using the oral route of administration.

Step 2—test implementation:

The animal is placed in the lit box, with the head directed towards the tunnel. The number of entries as well as the time spent in the lit box are recorded over a 5 minutes period after the first entry of the animal in the dark box.

The apparatus is cleaned between each animal using alcohol (70°).

5. Data Analysis and Results

All animals scored without entry into the lit box are excluded from the analysis.

A one-way analysis of variance (ANOVA) is used to test whether the mean of the number of entries into lit box or the mean of the time spent in the lit box differs among three or more groups. Where ANOVA indicates a significant difference (p≦0.05), Fisher's Protected Least Significant Difference is used to compare pairs of group means. Results are shown in FIGS. 2a, 2b, 3a and 3b. Compounds A and B are two of the preferred compounds of the invention.

Marble Burying Test

1. Purpose

The marble burying test (MB) is used to record the number of marbles buried by mice placed in a novel environment. It has some predictive value for anti-depressant and/or anxiolytic drugs.

2. Background

Mice, which are placed individually in a cage, bury glass marbles that are present in the cage. This test has been shown to be sensitive to benzodiazepines (BZD's) as these compounds reduce burying behaviour when compared to vehicle-treated control mice, without inducing changes in locomotor activity. Results have shown that in addition to BZD's, this test system is sensitive to the effects of selective serotonin reuptake inhibitors (SSRIs), serotonin noradrenaline reuptake inhibitors (SNRIs) and tricyclic antidepressants (TCAs).

3. Materials

Equipment

The apparatus consists of transparent polycarbonate cages (30 cm×18 cm×19 cm) containing a 5 cm layer of fine sawdust bedding and 20 glass marbles (diameter: 1.5 cm) spaced evenly along the walls of the cage.

Reagents

Test substance

Vehicle

4. Methods

Step 1—drug treatments:

Animals are randomly assigned to test substance (compound A of the invention) and control groups. Each animal is treated with vehicle or test compounds one hour before the test at appropriate doses and using the oral route of administration.

Step 2—test implementation:

Each animal is placed individually in the cages where it remains for a 20 min test session. On termination of the test session the animals are removed from the cage and the number of marbles at least two-thirds buried in the sawdust is recorded by an observer unaware of the treatment group.

5. Data Analysis and Results

A one-way analysis of variance (ANOVA) is used to test whether the mean number of marbles buried differs among three or more groups. Where ANOVA indicates a significant difference (p≦0.05), Fisher's Protected Least Significant Difference is used to compare pairs of group means.

Results are shown in FIG. 4.

Sprouting

Purpose:

Evaluation of antidepressant compounds with regards to their capability to induce neuronal sprouting in hippocampal cell cultures.

Background

Stress can lead to depression and hippocampal damage in animals. In line with these animal findings, patients suffering the PTSD (post traumatic stress disorder) have been shown to have hippocampal damage (and depression). Clinically active antidepressants have been found to induce hippocampal sprouting in cell cultures. Accordingly, a positive effect on sprouting would be a highly wanted aspect of the pharmacological profile of new antidepressants.

1. Primary Culture of Rat Hippocampal Neurons

A female rat of 19 days gestation was killed by cervical dislocation (Rats Wistar, Janvier, Le Genest-St-Isle, France), the fetuses were removed from the uterus. Their brains were removed and placed in ice-cold medium of Leibovitz (L15, Gibco, Invitrogen, Cergy-Pontoise). Meninges were carefully removed and hippocamps were dissected out. Hippocampal neurons were dissociated by trypsinization for 30 min at 37° C. (trypsin-EDTA, Gibco) in presence of DNAse I (Roche, Meylan, France). The reaction was stopped by addition of in medium of Eagle modified by Dulbecco (DMEM, Gibco) with 10% of fetal bovine serum (FBS, Gibco). The suspension was triturated with a 10-ml pipette and using a needle syringe 21G and centrifuged at 350×g for 10 min at room temperature. The pellet of dissociated cells was resuspended in L15 medium and was layered over a cushion of 3.5% solution of bovine serum albumin (BSA) in L15 medium. The tube was centrifuged 10 min at 180×g. The brake was trun off during the deceleration. The pellet was resuspended in L15 and centrifuged at 350×g. This final pellet was resuspended in culture medium consisting of Neurobasal (Gibco, ref 21103-049) supplemented with 2% B27 supplement (Gibco, ref. 17504-044), 2 mM L-Glutamine (Gibco). Viable cells were counted in a Neubauer cytometer using the trypan blue exclusion test (Sigma) and seeded on the basis of 30 000 cells per 35-mm Petri dishes (Nunc) precoated with poly-L-lysine.

Cells were allowed to adhere 2 h and maintained in a humidified incubator at 37° C. in 5% $CO_2$-95% air atmosphere. Culture medium was then added with tested compounds.

BDNF (Brain—Derived Neurotrophic Factor) (Tebu Peprotech) was tested at 50 ng/ml, a very active concentration, as a reference.

2. Evaluation of the Neurite Outgrowth

After 3 days of treatment, cultures were washed in phosphate-buffered saline (PBS, Gibco) and fixed in glutaraldehyde 2.5% in PBS.

40 neurons with neurites without branching were taken per condition with a camera (Coolpix 995, Nikon) fixed on microscope (Nikon, objective 20×) and the length measurement were made by analysis of pictures by software (Image-Pro Plus, France).

3. Data Analysis

Results are shown in FIG. 5.

A global analysis of the data was done using a one way analysis of variance (Anova). Where applicable, Fisher's PLSD test was used for multiple pairwise comparison. The level of significance was set at $p \leq 0.05$.

The invention claimed is:
1. A compound represented by formula (I):

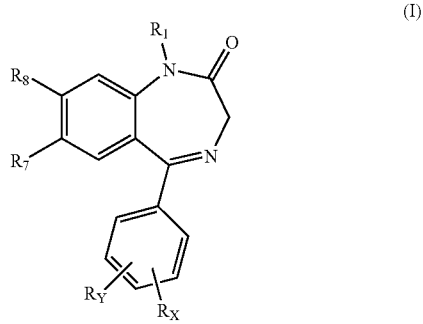

(I)

wherein:
$R_1$ represents a member selected from the group consisting of hydrogen, $(C_1-C_6)$ alkyl, aryl, $(C_1-C_6)$alkylaryl, aryl $(C_1-C_6)$alkyl group, $(C_3-C_6)$ alkenyl, and $(C_3-C_6)$ alkenylaryl,
$R_7$ represents a substituted or unsubstituted aryl or heteroaryl group, wherein said heteroaryl group contains from 4 to 18 carbon atoms and one or more heteroatoms selected from N, O and S, wherein $R_7$ is a substituted aryl group, it is mono- or bis-substituted by the following groups: $(C_1-C_6)$alkyl, $(C_3-C_6)$cycloalkyl, $(C_3-C_6)$cycloalkyloxy, $(C_1-C_6)$alkyloxy, $(C_3-C_6)$alkenyloxy, aryloxy, acyl, halogen, trifluoromethyl, difluoromethyl, cyano, nitro, hydroxy, carboxamide, amino, $(C_1-C_6)$ aminoalkyl, $(C_1-C_6)$aminodialkyl, $NCOR_{12}$ where $R_{12}$ is selected from the group consisting of $(C_1-C_6)$alkyl, $(C_1-C_6)$alkylaryl, aryl, and $—CONR_{13}R_{14}$ wherein $R_{13}$ and $R_{14}$, independently from each other, are selected from the group consisting of hydrogen, $(C_1-C_6)$alkyl, $(C_3-C_6)$alkenyl, alkylaryl, alkenylaryl, and aryl, and wherein $R_7$ is a substituted heteroaryl group, it is substituted with one or two substituents independently selected from the group consisting of halogen, amino, aminoacyl, $CONH_2$, $(C_1-C_6)$alkyl, aryloxy and $(C_1-C_6)$ alkyloxy,
$R_8$ represents hydrogen or an $OR_{10}$ group, wherein $R_{10}$ is a selected from the group consisting of hydrogen, $(C_1-C_6)$ alkyl, $(C_3-C_6)$cycloalkyl, $(C_3-C_6)$alkenyl, trifluoromethyl, difluoromethyl, $(C_3-C_6)$alkenylaryl, aryl, and a heterocyclic group, aromatic or not, having from 4 to 18 carbon atoms and 1 to 3 heteroatoms chosen from O, N and S,
when $R_{10}$ represents an aryl, it is mono- or bis-substituted by substituents selected from: hydrogen, $(C_1-C_6)$alkyl, $(C_3-C_6)$cycloalkyl, $(C_3-C_6)$cycloalkyloxy, $(C_1-C_6)$alkyloxy, $(C_3-C_6)$alkenyloxy, halogen, trifluoromethyl, difluoromethyl, cyano, nitro, hydroxy, carboxamide, amino, $(C_1-C_6)$aminoalkyl, $(C_1-C_6)$aminodialkyl $NCOR_{12}$ wherein $R_{12}$ is selected from the group consisting of $(C_1-C_6)$alkyl, $(C_1-C_6)$alkylaryl and aryl, and $—CONR_{13}R_{14}$ wherein $R_{13}$ and $R_{14}$, independently from each other, are selected from the group consisting of hydrogen, $(C_1-C_6)$alkyl, $(C_3-C_6)$alkenyl, alkylaryl, alkenylaryl, and aryl,
$R_X$ represents a member selected from the group consisting of hydrogen, halogen, methyl, methoxy, acetyl, trifluoromethyl, CN, COH and $CONH_2$,
$R_Y$ represents a member selected from the group consisting of hydrogen, halogen, $(C_1-C_6)$alkyl, $(C_3-C_6)$cycloalkyl, aryl, arylalkyl, $(C_3-C_6)$cycloalkyloxy, COH, $(C_1-C_6)$ alkyloxy, alkenyl, $(C_3-C_8)$alkenyloxy, alkynyl, alkynyloxy, acyl, trifluoromethyl, difluoromethyl, trifluoromethoxy, difluoromethoxy, cyano, nitro, hydroxy, carboxamide, amino, $(C_1-C_6)$aminoalkyl, $(C_1-C_6)$aminodialkyl, $NHCOR_{12}$ where $R_{12}$ is as defined above, and $—CONR_{13}R_{14}$ wherein $R_{13}$ and $R_{14}$ are as defined above,
with the proviso that, when $R_8$ is hydrogen, then one or $R_X$ and $R_Y$ is other than hydrogen,
or a pharmaceutically acceptable salt thereof.

2. The compound of formula (I) according to claim 1, wherein $R_8$ is hydrogen, alkoxy, or aryloxy.

3. The compound of formula (I) according to claim 1, wherein at least one of $R_X$ and $R_Y$ is other than hydrogen.

4. The compound of formula (I) according to claim 1, wherein $R_Y$ is an hydrogen atom and $R_X$ is other than hydrogen.

5. The compound of formula (I) according to claim 1, wherein the one of $R_X$ and $R_Y$, that is other than hydrogen, is on position 3 of the phenyl group represented in formula (I).

6. The compound of formula (I) according to claim 4, wherein $R_X$, is on position 3 of the phenyl group represented in formula (I).

7. The compound of formula (I) according to claim 1, wherein $R_X$ represents $CONH_2$, CN, or $COCH_3$, and is on position 3 or 4 of the phenyl group represented in formula (I).

8. The compound of formula (I) according to claim 1, wherein $R_Y$ is selected from the group consisting of hydrogen, halogen, $CF_3$, $(C_1-C_6)$aminoalkyl, $(C_1-C_6)$aminodialkyl, —$NHCOR_{12}$, —$CONH_2$, $(C_1-C_3$alkyloxy and $(C_1-C_6)$alkyl.

9. The compound of formula (I) according to claim 1, wherein $R_1$ represents hydrogen, alkyl, alkenyl, or arylalkyl.

10. The compound of formula (I) according to claim 1, wherein $R_7$ represents a furanyl group.

11. The compound of formula (I) according to claim 1, wherein $R_7$ represents an unsubstituted aryl group.

12. The compound of formula (I) according to claim 1, wherein $R_7$ represents a substituted aryl or heteroaryl group.

13. The compound of formula (I) according to claim 1, wherein $R_7$ represents an aryl or heteroaryl group substituted with one or two, substituents independently selected from the group consisting of halogen, amino, aminoacyl, $CONH_2$, $(C_1-C_6)$alkyl, aryloxy and $(C_1-C_6)$alkyloxy.

14. The compound of formula (I) according to claim 1, wherein $R_7$ is an aryl or heteroaryl group substituted with an alkoxy group.

15. The compound of formula (I) according to claim 1, wherein $R_7$ is a phenyl group substituted by at least one group on the ortho position.

16. The compound of formula (I) according to claim 1, wherein $R_7$ is a substituted phenyl group selected from the group consisting of 4-methoxy-phenyl, 4-fluoro-phenyl, 2-methoxy-phenyl, 2-chloro-phenyl, 4-chloro-phenyl, 3-chloro-phenyl, 3-methoxy-phenyl, 2,5-dimethoxy-phenyl, 2,6-dimethoxy-phenyl, 4-carbamoyl-phenyl, 4-cyanophenyl, 2,4-dimethoxy-phenyl, 4-carboxamide-phenyl, 4-acetyl-phenyl, 2-isopropoxy-phenyl, 2-phenoxy-phenyl, and 3,4-dimethoxy-phenyl groups.

17. A compound of formula (I) in accordance with claim 1, wherein said compound is selected from the group consisting of:

3-(8-Methoxy-1-methyl-2-oxo-7-phenyl-2,3-dihydro-1H-benzo[e][1,4]diazepin-5-yl)-benzonitrile;

3-[7-(4-Fluoro-phenyl)-8-methoxy-1-methyl-2-oxo-2,3-dihydro-1H-benzo[e][1,4]diazepin-5-yl]-benzonitrile;

3-[8-Methoxy-7-(2-methoxy-phenyl)-1-methyl-2-oxo-2,3-dihydro-1H-benzo[e][1,4]diazepin-5-yl]-benzonitrile;

3-[8-Methoxy-7-(4-methoxy-phenyl)-1-methyl-2-oxo-2,3-dihydro-1H-benzo[e][1,4]diazepin-5-yl]-benzonitrile;

3-[7-(2-Chloro-phenyl)-8-methoxy-1-methyl-2-oxo-2,3-dihydro-1H-1-benzo[e][1,4]diazepin-5-yl]-benzonitrile;

3-[7-(3-Chloro-phenyl)-8-methoxy-1-methyl-2-oxo-2,3-dihydro-1H-benzo[e][1,4]diazepin-5-yl]-benzonitrile;

3-[7-(4-Chloro-phenyl)-8-methoxy-1-methyl-2-oxo-2,3-dihydro-1H-benzo[e][1,4]diazepin-5-yl]-benzonitrile;

3-(7-Furan-2-yl-8-methoxy-1-methyl-2-oxo-2,3-dihydro-1H-benzo[e][1,4]diazepin-5-yl)-benzonitrile;

3-(1-Methyl-2-oxo-7-phenyl-2,3-dihydro-1H-benzo[e][1,4]diazepin-5-yl)-benzonitrile 3-[8-Methoxy-7-(2-methoxy-phenyl)-2-oxo-2,3-dihydro-1H-benzo[e][1,4]diazepin-5-yl]-benzonitrile;

3-(1-Methyl-2-oxo-7-phenyl-2,3-dihydro-1H-benzo[e][1,4]diazepin-5-yl)-benzonitrile;

3-[7-(2-Methoxy-phenyl)-1-methyl-2-oxo-2,3-dihydro-1H-benzo[e][1,4]diazepin-5-yl]-benzonitrile;

3-[7-(3-Methoxy-phenyl)-1-methyl-2-oxo-2,3-dihydro-1H-benzo[e][1,4]diazepin-5-yl]-benzonitrile;

3-[7-(4-Methoxy-phenyl)-1-methyl-2-oxo-2,3-dihydro-1H-benzo[e][1,4]diazepin-5-yl]-benzonitrile;

3-[7-(2,5-Dimethoxy-phenyl)-1-methyl-2-oxo-2,3-dihydro-1H-benzo[e][1,4]diazepin-5-yl]-benzonitrile;

3-[7-(2,6-Dimethoxy-phenyl)-1-methyl-2-oxo-2,3-dihydro-1H-benzo[e][1,4]diazepin-5-yl]-benzonitrile;

3-[7-(2,4-Dimethoxy-phenyl)-1-methyl-2-oxo-2,3-dihydro-1H-benzo[e][1,4]diazepin-5-yl]-benzonitrile;

8-Ethoxy-1-ethyl-5,7-diphenyl-1,3-dihydro-benzo[e][1,4]diazepin-2-one;

3-(8-Methoxy-1-methyl-2-oxo-7-phenyl-2,3-dihydro-1H-benzo[e][1,4]diazepin-5-yl)-benzamide;

3-[7-(4-fluoro-phenyl)-8-methoxy-1-methyl-2-oxo-2,3-dihydro-1H-1H-benzo[e][1,4]diazepin-5-yl]-benzamide;

3-[8-Methoxy-7-(2-methoxy-phenyl)-1-methyl-2-oxo-2,3-dihydro-1H-benzo[e][1,4]diazepin-5-yl]-benzamide;

3-[8-Methoxy-7-(4-methoxy-phenyl)-1-methyl-2-oxo-2,3-dihydro-1H-benzo[e][1,4]diazepin-5-yl]-benzamide;

3-[7-(2-Chloro-phenyl)-8-methoxy-1-methyl-2-oxo-2,3-dihydro-1H-benzo[e][1,4]diazepin-5-yl]-benzamide;

3-[7-(3-Chloro-phenyl)-8-methoxy-1-methyl-2-oxo-2,3-dihydro-1H-benzo[e][1,4]diazepin-5-yl]-benzamide;

3-[7-(4-Chloro-phenyl)-8-methoxy-1-methyl-2-oxo-2,3-dihydro-1H-benzo[e][1,4]diazepin-5-yl]-benzamide;

3-(7-Furan-2-yl-8-methoxy-1-methyl-2-oxo-2,3-dihydro-1H-benzo[e][1,4]diazepin-5-yl)-benzamide;

3-(1-methyl-2-oxo-7-phenyl-2,3-dihydro-1H-benzo[e][1,4]diazepin-5-yl)-benzamide;

3-[7-(2-methoxy-phenyl)-1-methyl-2-oxo-2,3-dihydro-1H-benzo[e][1,4]diazepin-5-yl]-benzamide;

3-[7-(3-methoxy-phenyl)-1-methyl-2-oxa-2,3-dihydro-1H-benzo[e][1,4]diazepin-5-yl]-benzamide;

3-[7-(4-methoxy-phenyl)-1-methyl-2-oxo-2,3-dihydro-1H-benzo[e][1,4]diazepin-5-yl]-benzamide;

3-[7-(2,5-Dimethoxy-phenyl)-1-methyl-2-oxo-2,3-dihydro-1H-benzo[e][1,4]diazepin-5-yl]-benzamide;

3-[7-(2,6-Dimethoxy-phenyl)-1-methyl-2-oxo-2,3-dihydro-1H-benzo[e][1,4]diazepin-5-yl]-benzamide;

3-[7-(2,4-Dimethoxy-phenyl)-1-methyl-2-oxo-2,3-dihydro-1H-benzo[e][1,4]diazepin-5-yl]-benzamide;

3-(8-Methoxy-7-(4-benzamide)-1-methyl-2-oxo-2,3-dihydro-1H-benzo[e][1,4]diazepin-5-yl)-benzamide;

3-[1-Hexyl-8-methoxy-7-(2-methoxy-phenyl)-2-oxo-2,3-dihydro-1H-benzo[e][1,4]diazepin-5-yl]-benzonitrile;

3-[8-Methoxy-7-(2-methoxy-phenyl)-2-oxo-2,3-dihydro-1H-benzo[e][1,4]diazepin-5-yl]-benzamide;

3-[8-Methoxy-7-6-methoxy-phenyl)-2-oxo-1-propyl-2,3-dihydro-1H-benzo[e][1,4]diazepin-5-yl]-benzonitrile;

3-[8-Methoxy-7-(2-methoxy-phenyl)-2-oxo-1-phenethyl-2,3-dihydro-1H-benzo[e][1,4]diazepin-5-yl]-benzonitrile;

3-[1-Benzyl-8-methoxy-7-(2-methoxy-phenyl)-2-oxo-2,3-dihydro-1H-benzo[e][1,4]diazepin-5-yl]-benzonitrile;

5-(3-Chloro-phenyl)-1-methyl-7-phenyl-1,3-dihydro-benzo[e][1,4]diazepin-2-one;

5-(2-Chloro-phenyl)-1-methyl-7-phenyl-1,3-dihydro-benzo[e][1,4]diazepin-2-one;

5-(4-Chloro-phenyl)-1-methyl-7-phenyl-1,3-dihydro-benzo[e][1,4]diazepin-2-one;

3-(8-Methoxy-1-methyl-2-oxo-7-(4-cyanophenyl)-2,3-dihydro-1H-benzo[e][1,4]diazepin-5-yl)-benzonitrile;
3-[1-Benzyl-8-methoxy-7-(2-methoxy-phenyl)-2-oxo-2,3-dihydro-1H-benzo[e][1,4]diazepin-5-yl]-benzamide;
3-[8-Methoxy-7-(2-methoxy-phenyl)-2-oxo-1-propyl-2,3-dihydro-1H-benzo[e][1,4]diazepin-5-yl]-benzamide;
3-[8-Methoxy-7-(2-methoxy-phenyl)-2-oxo-1-phenethyl-2,3-dihydro-1H-benzo[e][4]diazepin-5-yl]-benzamide;
3-[1-Hexyl-8-methoxy-7-(2-methoxy-phenyl)-2-oxo-2,3-dihydro-1H-benzo[e][1,4]diazepin-5-yl]-benzamide;
3-[7-(4-Acetyl-phenyl)-8-methoxy-1-methyl-2-oxo-2,3-dihydro-1H-benzo[e][1,4]diazepin-5-yl]-benzonitrile;
3-[7-(4-Acetyl-phenyl)-8-methoxy-1-methyl-2-oxo-2,3-dihydro-1H-benzo[e][1,4]diazepin-5-yl]-benzamide;
5-(4-Methoxy-phenyl)-1-methyl-7-phenyl-1,3-dihydro-benzo[e][1,4]diazepin-2-one;
5-(2-Methoxy-phenyl)-1-methyl-7-phenyl-1,3-dihydro-benzo[e][1,4]diazepin-2-one;
3-(7-Furan-2-yl-1-methyl-2-oxo-2,3-dihydro-1H-benzo[e][1,4]diazepin-5-yl)-benzonitrile;
3-[7-(3,4-Dimethoxy-phenyl)-1-methyl-2-oxo-2,3-dihydro-1H-benzo[e][1,4]diazepin-5-yl]-benzonitrile;
3-[7-(3,4-Dimethoxy-phenyl)-1-methyl-2-oxo-2,3-dihydro-1H-benzo[e][1,4]diazepin-5-yl]-benzamide;
5-(3,5-Dichloro-phenyl)-1-methyl-7-phenyl-1,3-dihydro-benzo[e][1,4]diazepin-2-one;
5-(3,4-Dichloro-phenyl)-1-methyl-7-phenyl-1,3-dihydro-benzo[e][1,4]diazepin-2-one;
5-(4-Fluoro-phenyl)-1-methyl-7-phenyl-1,3-dihydro-benzo[e][1,4]diazepin-2-one;
5-(3-Acetyl-phenyl)-1-methyl-7-phenyl-1,3-dihydro-benzo[e][1,4]diazepin-2-one;
1-Methyl-7-phenyl-5-(3-trifluoromethyl-phenyl)-1,3-dihydro-benzo[e][1,4]diazepin-2-one;
1-Methyl-5-(4-methyl-3-nitro-phenyl)-7-phenyl-1,3-dihydro-benzo[e][1,4]diazepin-2-one;
1-Methyl-7-phenyl-5-(4-trifluoromethoxy-phenyl)-1,3-dihydro-benzo[e][1,4]diazepin-2-one;
5-(3-Bromo-phenyl)-8-methoxy-1-methyl-7-phenyl-1,3-dihydro-benzo[e][1,4]diazepin-2-one;
3-[7-(2-Isopropoxy-phenyl)-8-methoxy-1-methyl-2-oxo-2,3-dihydro-1H-benzo[e][1,4]diazepin-5-yl]-benzonitrile;
5-(3,4-Dimethoxy-phenyl)-1-methyl-7-phenyl-1,3-dihydro-benzo[e][1,4]diazepin-2-one;
1-Methyl-5-(3-nitro-phenyl)-7-phenyl-1,3-dihydro-benzo[e][1,4]diazepin-2-one;
5-(3-Hex-1-ynyl-phenyl)-8-methoxy-1-methyl-7-phenyl-1,3-dihydro-benzo[e][1,4]diazepin-2-one;
{3-[3-(8-Methoxy-1-methyl-2-oxo-7-phenyl-2,3-dihydro-1H-benzo[e][1,4]diazepin-5-yl)-phenyl]-prop-2-ynyl}-carbamic acid tert-butyl ester;
5-(3-Amino-phenyl)-1-methyl-7-phenyl-1,3-dihydro-benzo[e][1,4]diazepin-2-one;
3-(1-Methyl-2-oxo-8-phenoxy-7-phenyl-2,3-dihydro-1H-benzo[e][1,4]diazepin-5-yl)-benzonitrile;
3-[7-(2-Methoxy-phenyl)-1-methyl-2-oxo-8-phenoxy-2,3-dihydro-1H-benzo[e][1,4]diazepin-5-yl]-benzonitrile;
3-[7-(2-Chloro-phenyl)-1-methyl-2-oxo-8-phenoxy-2,3-dihydro-1H-benzo[e][1,4]diazepin-5-yl]-benzonitrile;
3-(1-Methyl-2-oxo-8-phenoxy-7-phenyl-2,3-dihydro-1H-benzo[e][1,4]diazepin-5-yl)-benzamide;
3-[7-(2-Chloro-phenyl)-1-methyl-2-oxo-8-phenoxy-2,3-dihydro-1H-benzo[e][1,4]diazepin-5-yl]-benzamide;
3-[7-(2-Methoxy-phenyl)-1-methyl-2-oxo-8-phenoxy-2,3-dihydro-1H-benzo[e][1,4]diazepin-5-yl]-benzamide;
7-(2,6-Dimethoxy-phenyl)-5-(4-methoxy-phenyl)-1-methyl-1,3-dihydro-benzo[e][1,4]diazepin-2-one;
8-Methoxy-5-(4-methoxy-phenyl)-7-phenyl-1,3-dihydro-benzo[e][1,4]diazepin-5-one;
7-(2,6-Dimethoxy-phenyl)-1-methyl-5-(4-methyl-3-nitro-phenyl)-1,3-dihydro-benzo[e][1,4]diazepin-2-one;
3-[7-(2-Isopropoxy-phenyl)-8-methoxy-1-methyl-2-oxo-2,3-dihydro-1H-benzo[e][1,4]diazepin-5-yl]-benzamide;
5-(3-Methoxy-phenyl)-1-methyl-7-phenyl-1,3-dihydro-benzo[e][1,4]diazepin-2-one;
5-(3-Bromo-phenyl)-8-methoxy-7-phenyl-1,3-dihydro-benzo[e][1,4]diazepin-2-one;
3-[7-(2-Chloro-6-methoxy-phenyl)-2-methyl-2-oxo-2,3-dihydro-1H-benzo[e][1,4]diazepin-5-yl]-benzonitrile;
3-[7-(5-Chloro-2-methoxy-phenyl)-1-methyl-2-oxo-2,3-dihydro-1H-benzo[e][1,4]diazepin-5-yl]-benzonitrile;
3-[7-(2-Chloro-6-methoxy-phenyl)-1-methyl-2-oxo-2,3-dihydro-1H-benzo[e][1,4]diazepin-5-yl]-benzamide;
3-[7-(5-Chloro-2-methoxy-phenyl)-1-methyl-2-oxo-2,3-dihydro-1H-benzo[e][1,4]diazepin-5-yl]-benzamide;
3-(2-Oxo-7-phenyl-8-trifluoromethoxy-2,3-dihydro-1H-benzo[e][1,4]diazepin-5-yl)-benzonitrile;
3-(1-Methyl-2-oxo-7-phenyl-8-trifluoromethoxy-2,3-dihydro-1H-benzo[e][1,4]diazepin-5-yl)-benzonitrile;
3-(1-Methyl-2-oxo-7-phenyl-8-trifluoromethoxy-2,3-dihydro-1H-benzo[e][1,4]diazepin-5-yl)-benzamide;
3-[1-Methyl-2-oxo-7-(2-phenoxy-phenyl)-2,3-dihydro-1H-benzo[e][1,4]diazepin-5-yl]-benzonitrile;
3-[7-(2,6-Dimethoxy-phenyl)-8-methoxy-1-methyl-2-oxo-2,3-dihydro-1H-benzo[e][1,4]diazepin-5-yl]-benzonitrile;
3-[8-Methoxy-1-methyl-2-oxo-7-(2-phenoxy-phenyl)-2,3-dihydro-1H-benzo[e][1,4]diazepin-5-yl]-benzonitrile;
3-[1-Methyl-2-oxo-7-(2-phenoxy-phenyl)-2,3-dihydro-1H-benzo[e][1,4]diazepin-5-yl]-benzamide;
3-[7-(2,6-Dimethoxy-phenyl)-8-methoxy-1-methyl-2-oxo-2,3-dihydro-1H-benzo[e][1,4]diazepin-5-yl]-benzamide;
3-[8-Methoxy-1-methyl-2-oxo-7-(2-phenoxy-phenyl)-2,3-dihydro-1H-benzo[e][1,4]diazepin-5-yl]-benzamide;
8-Methoxy-1-methyl-7-phenyl-5-[3-(4-phenyl-butyl-phenyl]-1,3-dihydro-benzo[e][1,4]diazepin-2-one;
8-Methoxy-5-[3-(3-methoxy-prop-1-ynyl)-phenyl]-1-methyl-7-phenyl-1,3-dihydro-benzo[e][1,4]diazepin-2-one;
{3-[4-(8-Methoxy-1-methyl-2-oxo-7-phenyl-2,3-dihydro-1H-benzo[e][1,4]diazepin-5-yl)-phenyl]-prop-2-ynyl}carbamic acid tert-butyl ester;
8-Methoxy-1-methyl-7-phenyl-5-(4-phenylethynyl-phenyl)-1,3-dihydro-benzo[e][1,4]diazepin-2-one;
8-Methoxy-5-[4-(3-methoxy-prop-1-ynyl)-phenyl]-1-methyl-7-phenyl-1,3-dihydro-benzo[e][1,4]diazepin-2-one;
5-(3,4-Dichloro-phenyl)-7-(2,6-dimethoxy-phenyl)-1-methyl-1,3-dihydro-benzo[e][1,4]diazepin-2-one;
7-(2,6-Dimethoxy-phenyl)-5-(4-fluoro-phenyl)-1-methyl-1,3-dihydro-benzo[e][1,4]diazepin-2-one;
5-(3,4-Dimethoxy-phenyl)-7-(2,6-dimethoxy-phenyl)-1-methyl-1,3-dihydro-benzo[e][1,4]diazepin-2-one;
5-(2-Bromo-phenyl)-8-methoxy-7-phenyl-1,3-dihydro-benzo[e][1,4]diazepin-2-one;
8-Methoxy-5-[3-(3-methoxy-propyl)-phenyl]-1-methyl-7-phenyl-1,3-dihydro-benzo[e][1,4]diazepin-2-one;
5-(2-Bromo-phenyl)-8-methoxy-1-methyl-7-phenyl-1,3-dihydro-benzo[e][1,4]diazepin-2-one;

5-(4-Hex-1-ynyl-phenyl)-8-methoxy-1-methyl-7-phenyl-1,3-dihydro-benzo[e][1,4]diazepin-2-one;
8-Methoxy-5-[4-(3-methoxy-propyl)-phenyl]-1-methyl-7-phenyl-1,3-dihydro-benzo[e][1,4]diazepin-2-one;
{3-[4-(8-Methoxy-1-methyl-2-oxo-7-phenyl-2,3-dihydro-1H-benzo[e][1,4]diazepin-5-yl)-phenyl]-propyl}carbamic acid tert-butyl ester;
8-Methoxy-5-(4-methoxy-phenyl)-7-(2-methoxy-phenyl)-1-methyl-1,3-dihydro-benzo[e][1,4]diazepin-2-one;
7-(2,6-Dimethoxy-phenyl)-8-methoxy-5-(4-methoxy-phenyl)-1-methyl-1,3-dihydro-benzo[e][1,4]diazepin-2-one;
7-(2,5-Dimethoxy-phenyl)-8-methoxy-5-(4-methoxy-phenyl)-1-methyl-1,3-dihydro-benzo[e][1,4]diazepin-2-one;
7-(2-Fluoro-6-methoxy-phenyl)-8-methoxy-5-(4-methoxy-phenyl)-1-methyl-1,3-dihydro-benzo[e][1,4]diazepin-2-one;
8-Methoxy-5-(4-methoxy-phenyl)-1-methyl-7-(2-phenoxy-phenyl)-1,3-dihydro-benzo[e][1,4]diazepin-2-one;
5-(4-Bromo-phenyl)-8-methoxy-1-methyl-7-phenyl-1,3-dihydro-benzo[e][1,4]diazepin-2-one;
5-(4-Bromo-phenyl)-8-methoxy-7-phenyl-1,3-dihydro-benzo[e][1,4]diazepin-2-one; and
7-(2,6-Dimethoxy-phenyl)-1-methyl-5-m-tolyl-1,3-dihydro-benzo[e][1,4]diazepin-2-one.

18. A compound of formula (I) in accordance with claim 1, wherein said compound is selected from the group consisting of:
3-[7-(2,6-dimethoxy-phenyl)-1-methyl-2-oxo-2,3-dihydro-1H-benzo[e][1,4]diazepin-5-yl]-benzamide;
3-[7-(2,5-dimethoxy-phenyl)-1-methyl-2-oxo-2,3-dihydro-1H-benzo[e][1,4]diazepin-5-yl]-benzamide;
3-[8-methoxy-7-(4-methoxy-phenyl)-1-methyl-2-oxo-2,3-dihydro-1H-benzo[e][1,4]diazepin-5-yl]-benzamide;
3-[8-methoxy-7-(2-methoxy-phenyl)-1-methyl-2-oxo-2,3-dihydro-1H-benzo[e][1,4]diazepin-5-yl]-benzamide;
3-[7-(2-chloro-phenyl)-8-methoxy-1-methyl-2-oxo-2,3-dihydro-1H-benzo[e][1,4]diazepin-5-yl]-benzamide;
3-(8-methoxy-1-methyl-2-oxo-7-phenyl-2,3-dihydro-1H-benzo[e][1,4]diazepin-5-yl)-benzamide;
7-(2,6-Dimethoxy-phenyl)-5-(4-methoxy-phenyl)-1-methyl-1,3-dihydro-benzo[e][1,4]diazepin-2-one;
3-[7-(2-Chloro-6-methoxy-phenyl)-1-methyl-2-oxo-2,3-dihydro-1H-benzo[e][1,4]diazepin-5-yl]-benzamide;
3-[7-(2,6-Dimethoxy-phenyl)-8-methoxy-1-methyl-2-oxo-2,3-dihydro-1H-benzo[e][1,4]diazepin-5-yl]-benzamide;
3-[8-Methoxy-1-methyl-2-oxo-7-(2-phenoxy-phenyl)-2,3-dihydro-1H-benzo[e][1,4]diazepin-5-yl]-benzamide;
5-(2,4-Dichloro-phenyl)-7-(2,6-dimethoxy-phenyl)-1-methyl-1,3-dihydro-benzo[e][1,4]diazepin-2-one;
7-(2,6-Dimethoxy-phenyl)-1-methyl-5-m-tolyl-1,3-dihydro-benzo[e][1,4]diazepin-5-one; and
7-(2,6-Dimethoxy-phenyl)-8-methoxy-5-(4-methoxy-phenyl)-1-methyl-1,3-dihydro-benzo[e][1,4]diazepin-2-one.

19. A compound of formula (I) in accordance with claim 1, wherein said compound is selected from the group consisting of:
3-[7-(2,5-Dimethoxy-phenyl)-1-methyl-2-oxo-2,3-dihydro-1H-benzo[e][1,4]diazepin-5-yl]-benzamide;
3-[7-(2,6-Dimethoxy-phenyl)-1-methyl-2-oxo-2,3-dihydro-1H-benzo[e][1,4]diazepin-5-yl]-benzamide;
3-[7-(2,6-Dimethoxy-phenyl)-8-methoxy-1-methyl-2-oxo-2,3-dihydro-1H-benzo[e][1,4]diazepin-5-yl]-benzamide;
7-(2,6-Dimethoxy-phenyl)-5-(4-methoxy-phenyl)-1-methyl-1,3-dihydro-benzo[e][1,4]diazepin-2-one;
7-(2,6-Dimethoxy-phenyl)-5-(4-fluoro-phenyl)-1-methyl-1,3-dihydro-benzo[e][1,4]diazepin-2-one; and
7-(2,6-Dimethoxy-phenyl)-8-methoxy-5-(4-methoxy-phenyl)-1-methyl-1,3-dihydro-benzo[e][1,4]diazepin-2-one.

20. A pharmaceutical composition comprising at least one compound of formula (I) in accordance with claim 1, and a pharmaceutically acceptable vehicle or support.

* * * * *